United States Patent
Mellors et al.

(10) Patent No.: US 10,403,488 B2
(45) Date of Patent: Sep. 3, 2019

(54) SOLID PHASE EXTRACTION WITH CAPILLARY ELECTROPHORESIS

(71) Applicant: The University of North Carolina at Chapel Hill, Chapel Hill, NC (US)

(72) Inventors: John Scott Mellors, Carrboro, NC (US); William A. Black, Durham, NC (US); John Michael Ramsey, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/211,459

(22) Filed: Dec. 6, 2018

(65) Prior Publication Data
US 2019/0108992 A1 Apr. 11, 2019

Related U.S. Application Data

(62) Division of application No. 15/636,822, filed on Jun. 29, 2017, now Pat. No. 10,181,396, which is a
(Continued)

(51) Int. Cl.
*H01J 49/00* (2006.01)
*H01J 49/04* (2006.01)
(Continued)

(52) U.S. Cl.
CPC ...... *H01J 49/0459* (2013.01); *G01N 27/4473* (2013.01); *G01N 27/44743* (2013.01); *G01N 27/44791* (2013.01); *H01J 49/165* (2013.01)

(58) Field of Classification Search
CPC .. H01J 49/00; H01J 49/02; H01J 49/04; H01J 49/0404; H01J 49/0409; H01J 49/0413;
(Continued)

(56) References Cited

U.S. PATENT DOCUMENTS 5,872,010 A 2/1999 Karger et al.
5,958,203 A 9/1999 Parce et al.
(Continued)

FOREIGN PATENT DOCUMENTS

EP 2 184 602 A1 5/2010
JP 2000-310613 11/2000
(Continued)

OTHER PUBLICATIONS

Annesley "Ion Suppression in Mass Spectrometry" *Clinical Chemistry* 49(7):1041-1044 (2003).
(Continued)

*Primary Examiner* — Jason L McCormack
(74) *Attorney, Agent, or Firm* — Myers Bigel, P.A.

(57) ABSTRACT

Methods, systems and devices that provide fluid devices with at least one SPE bed adjacent (upstream of) a separation channel which may be in communication with an inlet of a Mass Spectrometer. The fluid device can be configured to operate using independently applied pressures to a BGE reservoir and a sample reservoir for pressure-driven injection that can inject a discrete sample plug into a separation channel that does not require voltage applied to the sample reservoir and can allow for in-channel focusing methods to be used. The methods, systems and devices are particularly suitable for use with a mass spectrometer but optical or other electronic detectors may also be used with the fluidic devices.

20 Claims, 26 Drawing Sheets

Related U.S. Application Data division of application No. 15/079,541, filed on Mar. 24, 2016, now Pat. No. 9,728,387.

(60) Provisional application No. 62/243,919, filed on Oct. 20, 2015.

(51) Int. Cl.
*G01N 27/447* (2006.01)
*H01J 49/16* (2006.01)

(58) Field of Classification Search
CPC ............. H01J 49/0422; H01J 49/0427; H01J 49/0431; H01J 49/0436; H01J 49/0445
USPC ........................................ 250/281, 282, 285
See application file for complete search history.

(56) References Cited

U.S. PATENT DOCUMENTS

| | | | |
|---|---|---|---|
| 6,074,827 | A | 6/2000 | Nelson et al. |
| 6,268,220 | B1 | 7/2001 | Heinecke |
| 6,375,817 | B1 | 4/2002 | Taylor et al. |
| 6,475,363 | B1 | 11/2002 | Ramsey |
| 6,833,068 | B2 | 12/2004 | Paul et al. |
| 7,391,020 | B2 | 6/2008 | Bousse et al. |
| 7,494,577 | B2 | 2/2009 | Williams et al. |
| 7,749,365 | B2 | 7/2010 | Nguyen et al. |
| 7,846,314 | B2 | 12/2010 | Gassmann |
| 7,927,476 | B2 | 4/2011 | Tian et al. |
| 8,759,753 | B1 | 6/2014 | Di Bussolo et al. |
| 9,006,648 | B2 | 4/2015 | Ramsey et al. |
| 9,139,426 | B2 | 9/2015 | Ramsey et al. |
| 9,255,905 | B1 | 2/2016 | Mellors et al. |
| 2001/0005489 | A1 | 6/2001 | Roach et al. |
| 2001/0035351 | A1 | 11/2001 | Simpson et al. |
| 2002/0112959 | A1 | 8/2002 | Xue et al. |
| 2002/0115293 | A1 | 8/2002 | Ghodsian |
| 2002/0189946 | A1 | 12/2002 | Wainright et al. |
| 2004/0088762 | A1 | 5/2004 | Oriedo et al. |
| 2004/0195099 | A1 | 10/2004 | Jacobson et al. |
| 2004/0224425 | A1 | 11/2004 | Gjerde et al. |
| 2005/0118599 | A1 | 6/2005 | Pawliszyn |
| 2006/0254915 | A1 | 11/2006 | Hirokawa et al. |
| 2007/0111329 | A1 | 5/2007 | Guzman |
| 2007/0134808 | A1 | 6/2007 | Sullivan |
| 2009/0253181 | A1 | 10/2009 | Vangbo et al. |
| 2010/0084271 | A1 | 4/2010 | Santiago et al. |
| 2011/0133077 | A1* | 6/2011 | Henion .................. G01N 1/405 250/288 |
| 2013/0327936 | A1* | 12/2013 | Ramsey .................. B05B 5/025 250/282 |
| 2014/0238856 | A1 | 8/2014 | Ramsey et al. |
| 2014/0272958 | A1 | 9/2014 | Ramsey et al. |
| 2014/0360877 | A1 | 12/2014 | Ramsey et al. |
| 2015/0099642 | A1 | 4/2015 | Barany et al. |

FOREIGN PATENT DOCUMENTS

| | | |
|---|---|---|
| WO | WO 98/04909 A1 | 2/1998 |
| WO | WO 01/69226 A1 | 9/2001 |
| WO | WO 2012/040098 A2 | 3/2012 |
| WO | WO 2012/125318 A2 | 9/2012 |

OTHER PUBLICATIONS

Apffel et al. "Enhanced sensitivity for peptide mapping with electrospray liquid chromatography-mass spectrometry in the presence of signal suppression due to trifluoroacetic acid-containing mobile phases" *Journal of Chromatography A* 712:177-190 (1995).

Au et al. "3D-printed microfluidic automation" *Lab on a Chip, Royal Society of Chemistry* 15:1934-1941 (2015).

Batz et al. "Chemical Vapor Deposition of Aminopropyl Silanes in Microfluidic Channels for Highly Efficient Microchip Capillary Electrophoresis-Electrospray Ionization-Mass Spectrometry" *Analytical Chemistry* 86:3493-3500 (2014).

Black et al. "Utilizing Microchip Capillary Electrophoresis Electrospray Ionization for Hydrogen Exchange Mass Spectrometry" *Analytical Chemistry* 87:6280-6287 (2015).

Breadmore et al. "Recent advances in enhancing the sensitivity of electrophoresis and electrochromatography in capillaries and microchips (2008-2010)" *Electrophoresis* 32:127-148 (2011).

Breadmore et al. "Recent advances in enhancing the sensitivity of electrophoresis and electrochromatography in capillaries and microchips (2010-2012)" *Electrophoresis* 34:29-54 (2013).

Broyles et al. "Sample Filtration, Concentration, and Separation Integrated on Microfluidic Devices" *Analytical Chemistry* 75(11):2761-2767 (2003).

Busnel et al. "High Capacity Capillary Electrophoresis-Electrospray Ionization Mass Spectrometry: Coupling a Porous Sheathless Interface with Transient-Isotachophoresis" *Analytical Chemistry* 82(22):9476-9483 (2010).

Chambers et al. "Monolithic Integration of Two-Dimensional Liquid Chromatography-Capillary Electrophoresis and Electrospray Ionization on a Microfluidic Device" *Analytical Chemistry* 83:842-849 (2011).

Cho et al. "Bias-free pneumatic sample injection in microchip electrophorese" *Journal of Chromatography A* 1063:253-256 (2005).

Dahlin et al. "Poly(dimethylsiloxane)-Based Microchip for Two-Dimensional Solid-Phase Extraction-Capillary Electrophoresis with an Integrated Electrospray Emitter Tip" *Analytical Chemistry* 77(16):5356-5363 (2005).

Dennis et al. "Development of a Photothermal Absorbance Detector for Use with Microfluidic Devices" *Analytical Chemistry* 82(10):4063-4071 (2010).

De Oliveira et al. "20 Years of Fatty Acid Analysis by Capillary Electrophoresis" *Molecules* 19:14094-14113 (2014).

Ermakov et al. "Computer Simulations of Electrokinetic Injection Techniques in Microfluidic Devices" *Analytical Chemistry* 72(15):3512-3517 (2000).

Fenn et al. "Electrospray Ionization for Mass Spectrometry of Large Biomolecules" *Science* 246:64-71 (1989).

Foote et al. "Preconcentration of Proteins on Microfluidic Devices Using Porous Silica Membranes" *Analytical Chemistry* 77(1):57-63 (2005).

Gilar et al. "Mixed-mode chromatography for fractionation of peptides, phosphopeptides, and sialylated glycopeptides" *Journal of Chromatography A* 1191:162-170 (2008).

Gong et al. "Study of injection bias in a simple hydrodynamic injection in microchip CE" *Electrophoresis* 28:1564-1571 (2007).

Guetschow et al. "Subsecond Electrophoretic Separations from Droplet Samples for Screening of Enzyme Modulators" *Analytical Chemistry* 86:10373-10379 (2014).

Hernandez et al. "Analysis of opioid peptides by on-line SPE-CE-ESI-MS" *Electrophoresis* 28:3957-3965 (2007).

Hua et al. "On-chip solid phase extraction and enzyme digestion using cationic PolyE-323 Coatings and porous polymer monoliths coupled to electrospray mass spectrometry" *Journal of Chromatography A* 1218:4039-4044 (2011).

Ibanez et al. "Metabolomics, peptidomics and proteomics applications of capillary electrophoresis-mass spectrometry in Foodomics: A review" *Analytica Chimica Acta* 802:1-13 (2013).

International Search Report and the Written Opinion of the International Searching Authority corresponding to International Patent Application No. PCT/US2016/052801 (15 pages) (dated Jan. 12, 2017).

Jacobson et al. "Microchip Capillary Electrophoresis with an Integrated Postcolumn Reactor" *Analytical Chemistry* 66(20):3472-3476 (1994).

Jemere et al. "An integrated solid-phase extraction system for sub-picomolar detection" *Electrophoresis* 23:3537-3544 (2002).

Jorgenson et al., Free-Zone Electrophoresis in Glass Capillaries, *Clinical Chemistry*, 1981, pp. 1551-1553, vol. 27, No. 9.

Kang et al. "Polymer monolith-integrated multilayer poly(dimethylsiloxane) microchip for online microextraction and elextrophoresis" *Electrophoresis* 31:3028-3034 (2010).

(56) References Cited

OTHER PUBLICATIONS

Kašička et al. "Isotachophoretic Electrodesorption of Proteins From an Affinity Adsorbent on a Microscale" *Journal of Chromatography* 273:117-128 (1983).
Kitagawa et al. "Recent applications of on-line sample preconcentration techniques in capillary electrophoresis" *Journal of Chromatography A* 1335:43-60 (2014).
Lazar et al. "Subattomole-Sensitivity Microchip Nanoelectrospray Source with Time-of-Flight Mass Spectrometry Detection" *Analytical Chemistry* 71:3627-3631 (1999).
Lazar et al. "Novel microfabricated device for electrokinetically induced pressure flow and electrospray ionization mass spectrometry" *Journal of Chromatography A* 892:195-201 (2000).
Lazar et al. "On-Chip Proteolytic Digestion and Analysis Using 'Wrong-Way-Round' Electrospray Time-of-Flight Mass Spectrometry" *Analytical Chemistry* 73:1733-1739 (2001).
Lee et al. "Pressure-Driven Sample Injection with Quantitative Liquid Dispensing for On-Chip Electrophoresis" *Analytical Sciences* 20:483-487 (2004).
Lee et al. "Control-free Air Vent System for Ultra-low Volume Sample Injection on a Microfabricated Device" *Analytical Sciences* 21:465-468 (2005).
Li et al. "Separation and Identification of Peptides from Gel-Isolated Membrane Proteins Using a Microfabricated Device for Combined Capillary Electrophoresis/Nanoelectrospray Mass Spectrometry" *Analytical Chemistry* 72(3):599-609 (2000).
Li et al. "A novel mixed-mode solid phase extraction coupled with LC-MS/MS for the re-evaluation of free 3-nitrotyrosine in human plasma as an oxidative stress biomarker" *Talanta* 140:45-51 (2015).
Long et al. "Integrated multilayer microfluidic device with a nanoporous membrane interconnect for online coupling of solid-phase extraction to microchip electrophoresis" *Lab on a Chip, The Royal Society of Chemistry* 7:1819-1824 (2007).
Mallet et al. "A study of ion suppression effects in electrospray ionization from mobile phase additives and solid-phase extracts" *Rapid Communications in Mass Spectrometry* 18:49-58 (2004).
Marchiarullo et al. "Towards an integrated microfluidic device for spaceflight clinical diagnostics Microchip-based solid-phase extraction of hydroxyl radical markers" *Journal of Chromatography A* 1200:198-203 (2008).
Medina-Casanellas et al. "Transient isotachophoresis in on-line solid phase extraction capillary electrophoresis time-of-flight-mass spectrometry for peptide analysis in human plasma" *Electrophoresis* 32:1750-1759 (2011).
Mellors et al. "Fully Integrated Glass Microfluidic Device for Performing High-Efficiency Capillary Electrophoresis and Electrospray Ionization Mass Spectrometry" *Analytical Chemistry* 80(18):6881-6887 (2008).
Mellors et al. "Integrated Microfluidic Device for Automated Single Cell Analysis Using Electrophoretic Separation and Electrospray Ionization Mass Spectrometry" *Analytical Chemistry* 82(3):967-973 (2010).
Mellors et al. "Hybrid Capillary/Microfluidic System for Comprehensive Online Liquid Chromatography-Capillary Electrophoresis-Electrospray Ionization-Mass Spectrometry" *Analytical Chemistry* 85:4100-4106 (2013).
Nge et al. "Ion-permeable membrane for on-chip preconcentration and separation of cancer marker proteins" *Electrophoresis* 32:1133-1140 (2011).
Nge et al. "Microfluidic chips with reversed-phase monoliths for solid phase extraction and on-chip labeling" *J. Chromatogr. A* 1261:129-135 (2012).
Nge et al. "Integrated Affinity and Electrophoresis Systems for Multiplexed Biomarker Analysis, Clinical Applications of Capillary Electrophoresis Methods and Protocols" *Methods in Molecular Biology* pp. 189-201, Chapter 18, HumanaPress (2013).
Nie et al. "An automated integrated platform for rapid and sensitive multiplexed protein profiling using human saliva samples" *Lab on a Chip, The Royal Society of Chemistry* 14:1087-1098 (2014).
Nuchtavorn et al. "Recent applications of microchip electrophoresis to biomedical analysis" *Journal of Pharmaceutical and Biomedical Analysis* 113:72-96 (2015).
Oblath et al. "A microfluidic chip integrating DNA extraction and real-time PCR for the detection of bacteria in saliva" *Lab on a Chip, The Royal Society of Chemistry* 13:1325-1332 (2013).
Oleschuk et al. "Trapping of Bead-Based Reagents within Microfluidic Systems: On-Chip Solid-Phase Extraction and Electrochromatography" *Analytical Chemistry* 72:585-590 (2000).
Osbourn et al. "On-line preconcentration methods for capillary electrophoresis" *Electrophoresis* 21:2768-2779 (2000).
Pascali et al. "Recent advances in the application of CE to Forensic sciences, an update over years 2009-2011" *Electrophoresis* 33:117-126 (2012).
Pontillo et al. "CE-MS-based proteomics in biomarker discovery and clinical application" *Proteomics Clin. Appl.* 9:322-334 (2015).
Puig et al. "Sorbent preconcentration procedures coupled to capillary electrophoresis for environmental and biological applications" *Analytica Chimica Acta* 616:1-18 (2008).
Ramautar et al. "Developments in coupled solid-phase extraction-capillary electrophoresis 2009-2011" *Electrophoresis* 33:243-250 (2012).
Ramautar et al. "Developments in coupled solid-phase extraction-capillary electrophoresis 2011-2013" *Electrophoresis* 35:128-137 (2014).
Ramsey et al. "Generating Electrospray from Microchip Devices Using Electroosmotic Pumping" *Analytical Chemistry* 69(6):1174-1178 (1997).
Redman et al. "Integrated Microfluidic Capillary Electrophoresis-Electrospray Ionization Devices with Online MS Detection for the Separation and Characterization of Intact Monoclonal Antibody Variants" *Analytical Chemistry* 87:2264-2272 (2015).
Robledo et al. "Review of the CE-MS platform as a powerful alternative to conventional couplings in bio-omics and target-based applications" *Electrophoresis* 35:2292-2308 (2014).
Rogeberg et al. "On-line solid phase extraction-liquid chromatography, with emphasis on modern bioanalysis and miniaturized systems" *Journal of Pharmaceutical and Biomedical Analysis* 87:120-129 (2014).
Saito et al. "Instrumentation design for hydrodynamic sample injection in microchip electrophoresis: A review" *Electrophoresis* 33:2614-2623 (2012).
Smejkal et al. "Microfluidic isotachophoresis: A review" *Electrophoresis* 34:1493-1509 (2013).
Tempels et al. "On-line coupling of SPE and DE-MS for peptide analysis" *Electrophoresis*, 28:1319-1326 (2007).
Timerbaev "Capillary electrophoresis of inorganic ions: An update" *Electrophoresis* 25:4008-4031 (2004).
Tomlinson "Enhanced Performance Membrane Preconcentration-Capillary Electrophoresis-Mass Spectrometry (mPC-DE-MS) in Conjunction with Transient Isotachophoresis for Analysis of Peptide Mixtures" *J. High Resol. Chromatogr.* 18:384-386 (1995).
Wang et al. "Multifunctional protein processing chip with integrated digestion, solid-phase extraction, separation and electrospray" *Electrophoresis* 31:3703-3710 (2010).
Wang et al. "Capillary Electrophoresis-Mass Spectrometry in Metabolomics: The Potential for Driving Drug Discovery and Development" *Current Drug Metabolism* 14(7):807-813 (2013).
Waterval et al. "Qualitative analysis of pharmaceutically active peptides using on-capillary analyte preconcentration transient isotachophoresis" *Electrophoresis* 21:2851-2858 (2000).
Waters "An Overview of the Principles of $MS^E$, The Engine that Drives MS Performance" [White Paper] (8 pages) (2011).
Xue et al. "Integrated Multichannel Microchip Electrospray Ionization Mass Spectrometry: Analysis of Peptides from On-chip Tryptic Digestion of Melittin" *Rapid Communications in Mass Spectrometry* 2:1253-1256 (1997).
Xue et al. "Multichannel Microchip Electrospray Mass Spectrometry" *Anal. Chem.* 69:426-430 (1997).
Yang et al. "Membrane Preconcentration CE, A new approach to preconcentrating samples before separation" *Analytical Chemistry News & Features* 71:183A-189A (1999).

(56) References Cited

OTHER PUBLICATIONS

Zhang et al. "Microfabricated Devices for Capillary Electrophoresis-Electrospray Mass Spectrometry" *Analytical Chemistry* 71(15):3258-3264 (1999).

* cited by examiner

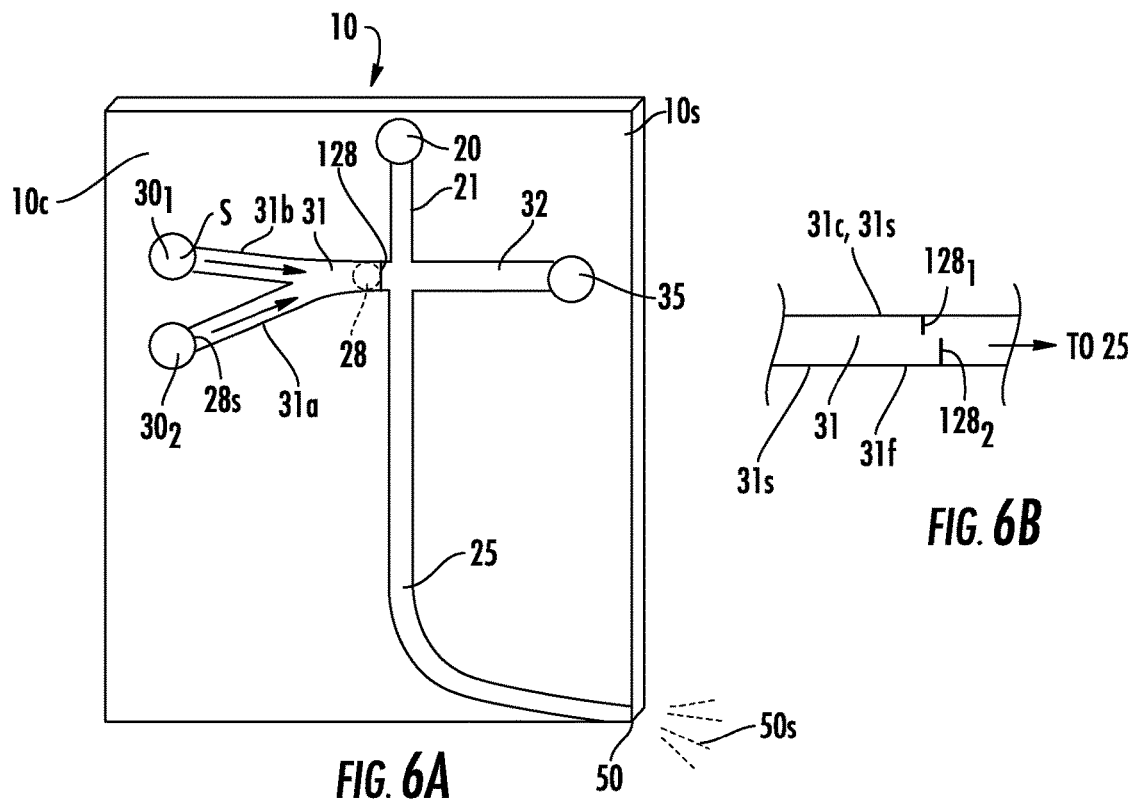
FIG. 6A
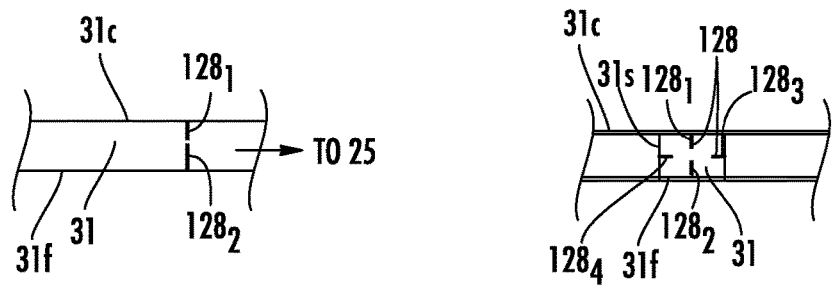
FIG. 6B
FIG. 6C    FIG. 6D
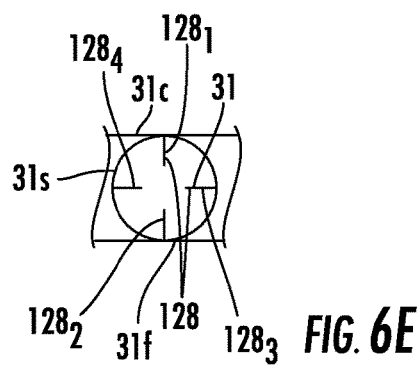
FIG. 6E
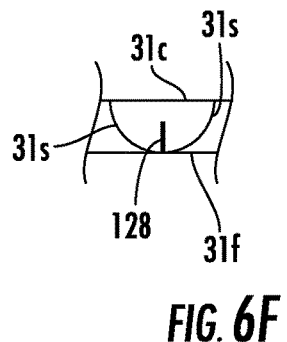
FIG. 6F

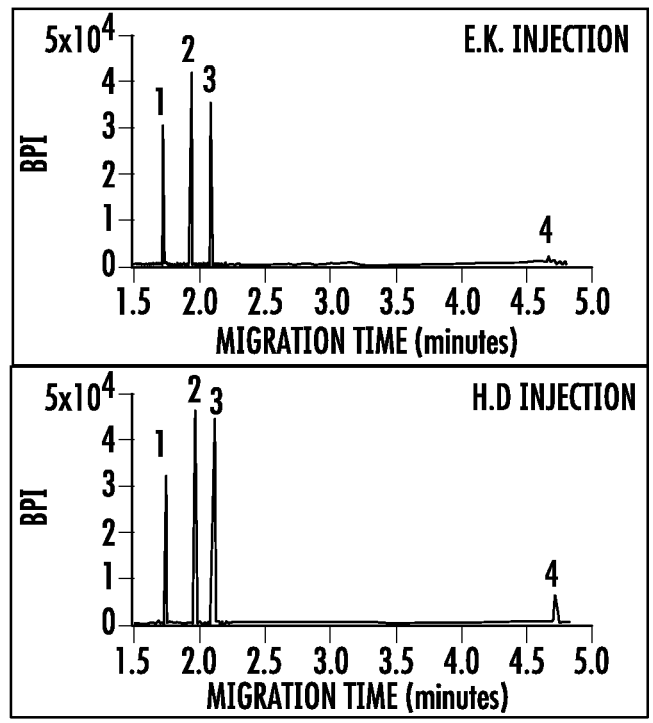
FIG. 13A
FIG. 13B
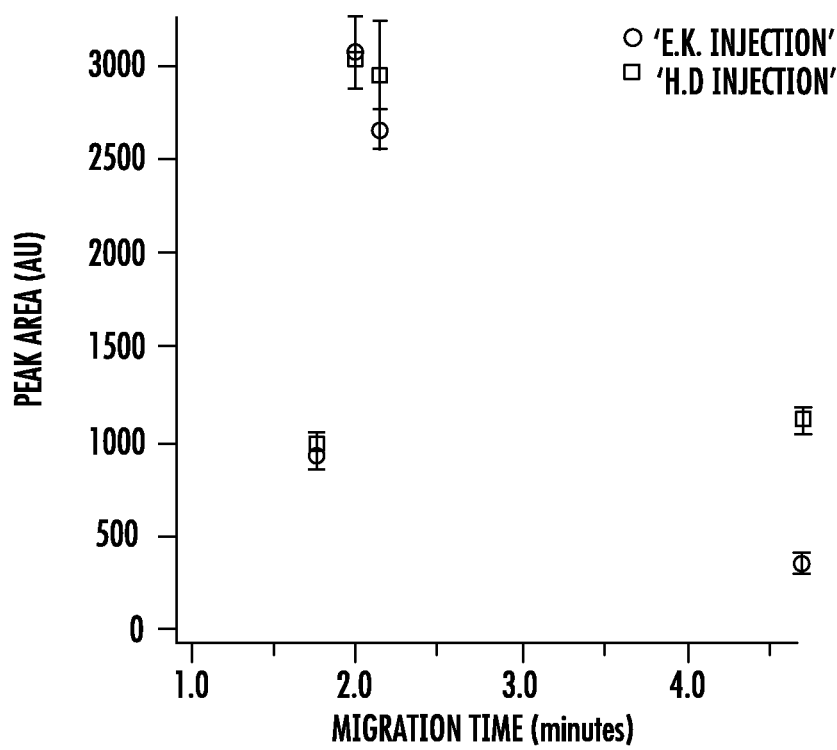
FIG. 14

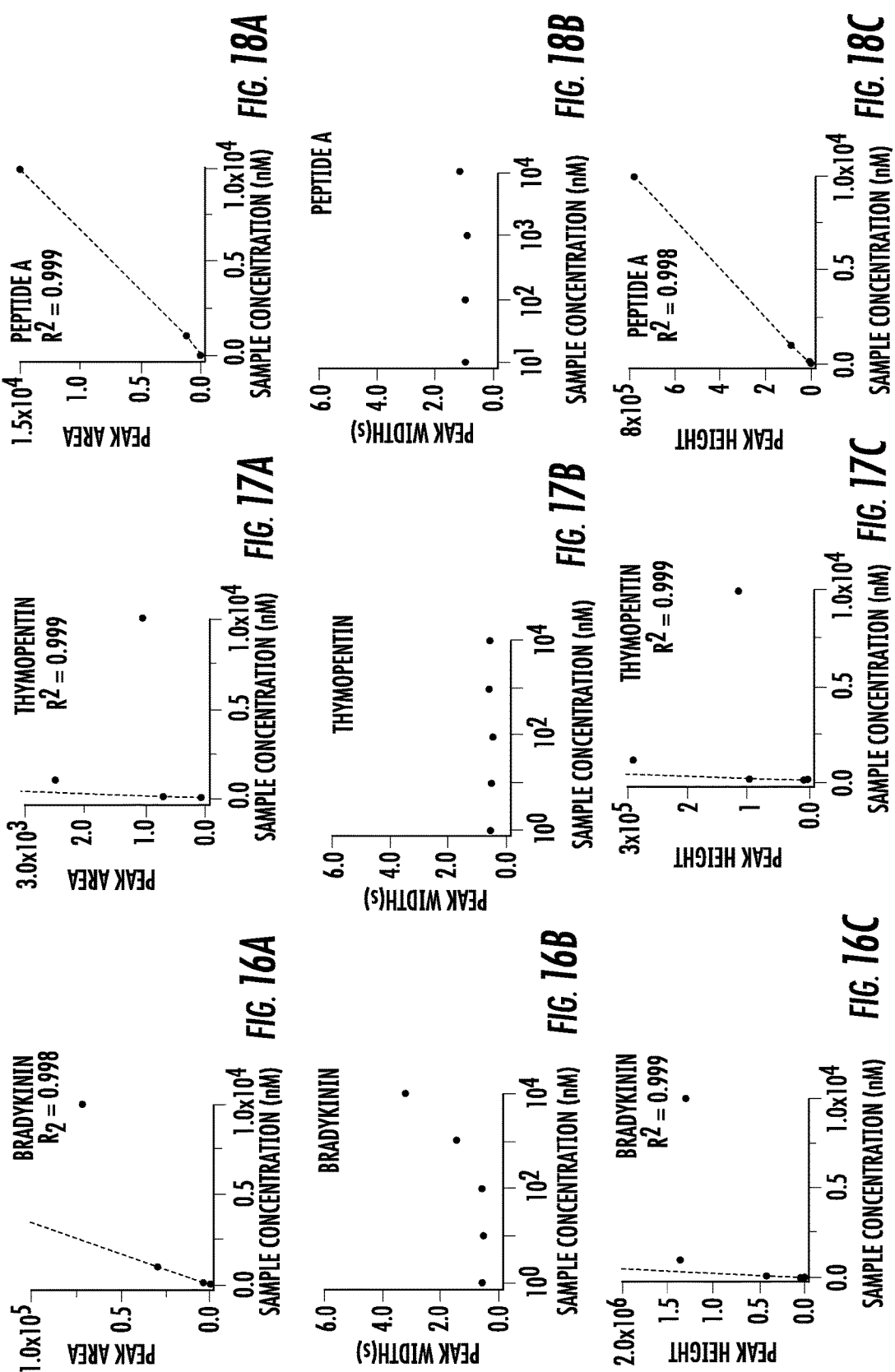

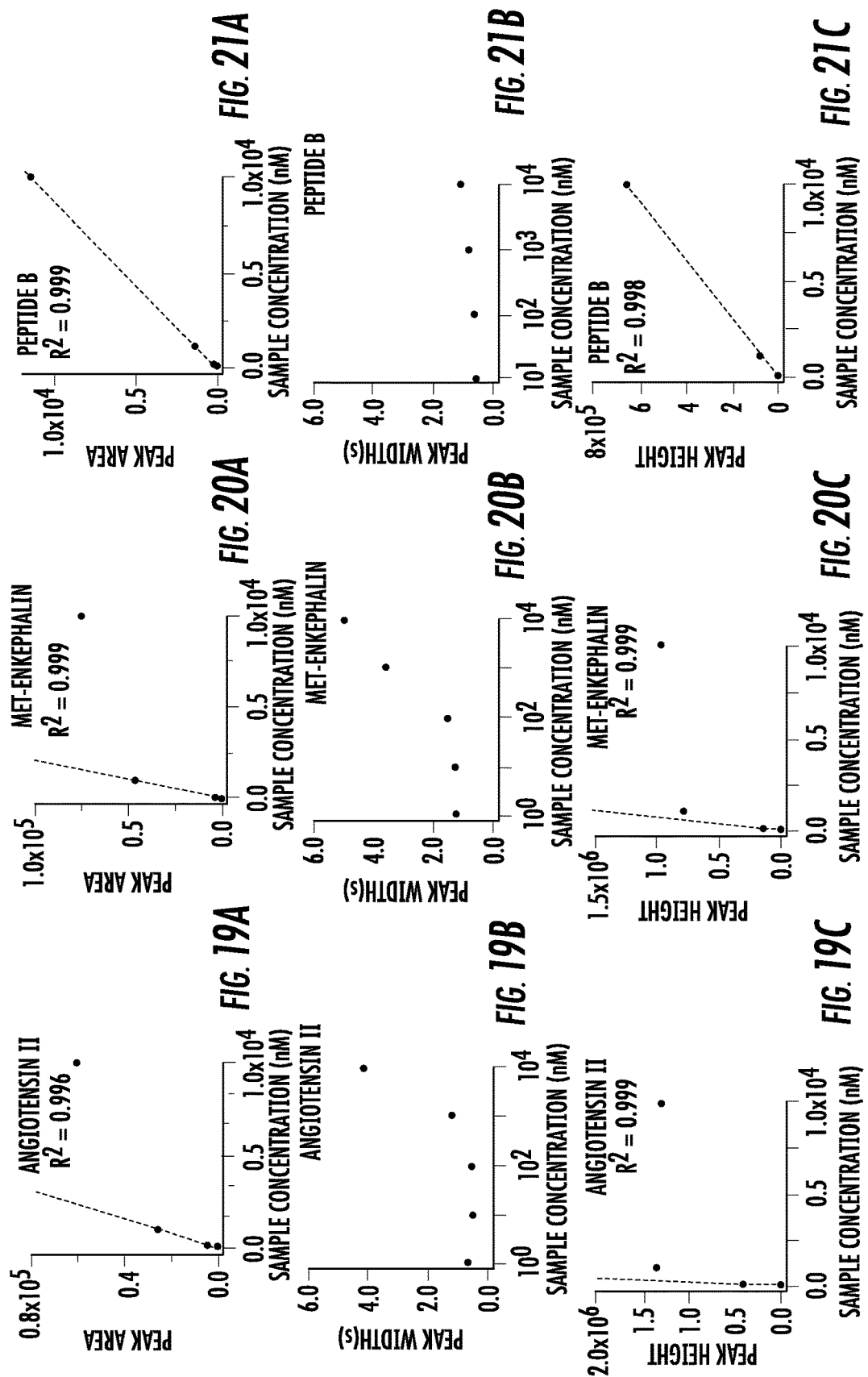

SOLID PHASE EXTRACTION WITH CAPILLARY ELECTROPHORESIS

RELATED APPLICATIONS

This application is a divisional of U.S. patent application Ser. No. 15/636,822, filed Jun. 29, 2017, which is a divisional of U.S. patent application Ser. No. 15/079,541, filed Mar. 24, 2016, which claims the benefit of and priority to U.S. Provisional Application Ser. No. 62/243,919, filed Oct. 20, 2015, the contents of which are hereby incorporated by reference as if recited in full herein.

FIELD OF THE INVENTION

This invention is related to sample processing that may be particularly suitable for electrospray ionization and/or sample processing systems that interface with mass spectrometers.

BACKGROUND OF THE INVENTION

Electrospray ionization ("ESI") is an important technique for the analysis of biological materials contained in solution by mass spectrometry. See, e.g., Cole, R. B. *Electrospray Ionization Mass Spectrometry: Fundamentals, Instrumentation & Applications*; John Wiley and Sons, Inc.: New York, 1997. Electrospray ionization was developed in the late 1980s and was popularized by the work of Fenn. See, e.g., Fenn J B, Mann M, Meng C K, Wong S F & Whitehouse C M (1989), *Electrospray ionization for mass-spectrometry of large biomolecules, Science* 246, 64-71. Simplistically, electrospray ionization involves the use of electric fields to disperse a sample solution into charged droplets. Through subsequent evaporation of the droplets, analyte ions contained in the droplet are either field emitted from the droplet surface or the ions are desolvated resulting in gas phase analyte ions. The source of the liquid exposed to the electric field and to be dispersed is ideally one of small areal extent as the size of the electrospray emitter directly influences the size of droplets produced. Smaller droplets desolvate more rapidly and have fewer molecules present per droplet leading to greater ionization efficiencies. These ions can be characterized by a mass analyzer to determine the mass-to-charge ratio. Further analyte structural information can be obtained by employing tandem mass spectrometry techniques.

Separation of analytes prior to electrospray ionization is important for minimizing ionization suppression and MS spectral complexity. Microfluidic capillary electrophoresis with integrated electrospray ionization has been demonstrated as a fast and efficient method of coupling a liquid phase chemical separation with mass spectroscopy detection. See, e.g., Anal. Chem. 2008, 50, 6881-6887; and Anal. Chem. 2015, 87, 2264-2272. Conventional microfluidic methods that employ electrokinetic flow of sample into the separation channel are subject to injection bias and cannot effectively be used for some on-device sample focusing methods. Further, the injection of a well-defined band of sample into the separation channel of the microfluidic device can be important to achieving an efficient separation.

Most of the efforts to integrate sample processing with CE can be classified as either electrophoretic or chromatographic based. Electrophoretic based techniques, including sample stacking, sweeping, pH induced stacking, and transient isotachophoresis (tITP), can be simple to implement and can require little instrumentation development. Unfortunately, these techniques cannot typically load a sample volume larger than the volume of the capillary which limits the achievable concentration and sensitivity improvement. Furthermore, electrophoretic methods often concentrate matrix components equally to the analytes of interest, which can reduce separation performance. Finally, these methods can be limited to a narrow scope of analyte and buffer conditions, and may not be as widely applicable as other sample processing techniques.

On the other hand, chromatographic-based techniques, such as solid phase extraction (SPE), are typically more versatile than electrophoretic-based methods and can offer higher pre-concentration values based on the ability to load multiple capillary volumes onto the chromatographic sorbent. See, e.g., Ramautar et al. *Electrophoresis* 2014, 35, 128-137, the contents of which are hereby incorporated by reference herein. However, these methods present their own shortcomings. The presence of the SPE sorbent in the separation capillary can lead to clogging and disruption of the electroosmotic flow (EOF), reducing separation performance. Furthermore, in this scenario, matrix components enter the separation capillary, which can lead to wall interactions and further diminish the separation performance. On-line coupling, where the SPE sorbent is separate from the CE capillary but connected via a flow stream with tubing and valves, is the most common method for combining SPE with CE. The decoupling of the SPE sorbent from the CE capillary can inhibit or prevent clogging and EOF disruption. Additionally, the inclusion of valves between the SPE sorbent and the CE capillary can direct the matrix components to waste and prevent them from entering the CE capillary. Unfortunately, on-line coupling of SPE and CE often requires complex instrumentation. Furthermore, the transfer of the sample band from the SPE sorbent to the CE capillary typically introduces band broadening, limiting the resulting separation performance. Additionally, dead volume present in the on-line system can dilute the concentrated analyte band, reducing the amount of pre-concentration that can be achieved. Coupling sample processing with CE without sacrificing the separation performance can be a very challenging task.

SUMMARY OF EMBODIMENTS OF THE INVENTION

Embodiments of the invention are directed to microfluidic sample processing systems and methods that integrate sample processing and employ on-line solid phase extraction (SPE) with microchip CE-ESI and/or microchip CE-detector systems.

Embodiments of the invention provide fluidic systems and methods that can integrate sample processing with on-line SPE using fluidic devices.

Embodiments of the invention provide SPE-CE-MS and/or SPE-CE-detector systems and methods that can be configured to eliminate or reduce band broadening imparted on the sample during the transfer between the SPE bed and CE capillary using transient isotachophoresis (tITP) to refocus an analyte band prior to separation. The tITP can act as a non-linear electrophoretic focusing technique where the sample is sandwiched between a leading fast moving electrolyte (LE) and a trailing slower moving electrolyte (TE). Sample analytes will focus into discreet zones based upon their electrophoretic mobilities. By utilizing this technique, band broadening imparted onto the sample during the SPE elution and transfer step can be reduced, resulting in a narrow injection plug allowing for a high performance separation. Sample pre-concentration factors can be more than two orders of magnitude without any reduction in separation performance.

In some particular embodiments, CE-ESI-MS and/or CE-optical detector systems can employ fluidic devices with simple, pressure-driven injection methods that can independently be applied to a plurality of different fluid reservoirs.

In some embodiments, pressure-driven sample loading and/or injection methods can also be used with on-device sample focusing methods such as transient isotachophoresis.

Embodiments of the invention are directed to methods of sample processing. The methods include providing a fluidic device with at least one microfluidic or nanofluidic separation channel in fluid communication with a background electrolyte (BGE) reservoir, and a nanofluidic or microfluidic sample channel in fluid communication with the separation channel. The sample channel includes at least one solid phase extraction (SPE) bed. The method also includes flowing a sample through the sample channel, across the at least one SPE bed, and into the separation channel then electrophoretically separating an analyte component from the sample in the separation channel and performing at least one of: (a) electrospraying the analyte component from at least one emitter in fluid communication with the separation channel toward at least one of a collection device or an inlet of a mass spectrometer; and (b) detecting a signal corresponding to the analyte component in, or emerging from, the separation channel.

The method can include pre-concentrating the sample prior to the electrophoretic separation.

The sample can be an ionized sample.

The pre-concentrating can include flowing the ionized sample in the separation channel in a first direction following a leading electrolyte with a first mobility, and in advance of a trailing electrolyte with a second mobility lower than the first mobility, so that if the sample comprises multiple components, a component of the sample having a highest mobility flows directly behind the leading electrolyte, and a component of the sample having a lowest mobility flows directly in advance of the trailing electrolyte, in the first direction.

The sample can be flowed across the at least one SPE bed and into the separation channel without directing the sample through a valve.

The electrophoretically separating the analyte component can include applying an electric field to the fluidic device so that at least a component of the electric field is parallel to an axial direction of a portion of the separation channel.

The applying the electric field can include applying an electrical potential difference between a first position in the BGE reservoir and a second position downstream from the first position. The second position can be located in the separation channel or in a pump channel or in a reservoir in fluid communication with one or both of the separation or the pump channel of the fluidic device.

The method can include flowing an ion-pairing agent across the at least one SPE bed in advance of, or together with, the sample; rinsing the ion pairing agent from the sample channel into a waste channel in fluid communication with the sample channel; and after rinsing the ion pairing agent from the sample channel, flowing an elution fluid in the sample channel before or during the electrophoretic separation.

The ion-pairing agent can include trifluoroacetic acid (TFA).

The method can include, after flowing the sample through the sample channel and across the at least one SPE bed, flowing an elution fluid through the sample channel and across the at least one SPE bed.

The method can include, prior to flowing the sample across the at least one SPE bed, pre-conditioning the SPE bed by flowing a pre-conditioning fluid across the at least one SPE bed and into a waste reservoir of the fluidic device.

The method can include, prior to flowing the sample through the sample channel, forming the at least one SPE bed in the sample channel by flowing a SPE material into the sample channel.

The SPE bed has a length, measured along a flow direction defined by the sample channel, that can be between 100 µm and 1000 µm, and a volume that can be between about 50 pL to about 10 nL.

The method can include using a blocking member to at least partially occlude the sample channel. The blocking member can be positioned adjacent to an end of the at least one SPE bed that is closest to the separation channel.

The method can include flowing the sample through the sample channel by pressurizing sealed headspaces of the BGE reservoir, a waste reservoir, and a sample reservoir comprising the sample. The BGE reservoir, the waste reservoir, and the sample reservoir can each be in fluid communication with the separation channel. The sample can be flowed through the sample channel without applying a voltage to the sample reservoir, to the BGE reservoir, or to the waste reservoir and/or with no electric potential gradient in any of the sample channel, the BGE channel and the waste channel.

The method can include applying hydrodynamic pressure to cause the sample to flow through the sample channel, across the at least one SPE bed, and into the separation channel.

The applying hydrodynamic pressure, where used, can include (a) first, concurrently applying pressures of between 0.1 pounds per square inch (psi) and 50 psi to each of a sealed headspace of a waste reservoir of the fluidic device and a sealed headspace of a sample reservoir of the fluidic device. A pressure applied to the sealed headspace of the waste reservoir is less than a pressure applied to the sealed headspace of the sample reservoir. The method then includes: (b) second, concurrently applying pressures to a sealed headspace of the BGE reservoir and to the sealed headspace of the sample reservoir; and (c) third, reducing the pressure applied to the sealed headspace of the sample reservoir and applying a pressure of between 0.1 psi and 50 psi to the sealed headspace of the BGE reservoir so that the pressure applied to the sealed headspace of the BGE reservoir is greater than the pressure applied to the sealed headspace of the sample reservoir to flush the sample from the sample channel into the separation channel.

The electrophoretically separating the analyte component from the sample can include reducing the pressure applied to the sealed headspace of the BGE reservoir and applying an electrical potential difference between a first position in the BGE reservoir and a second position downstream from the first position, when the sample is in the separation channel.

The electrophoretically separating the analyte component from the sample can include removing a pressure applied to a sealed headspace of the BGE reservoir while applying and electrical potential difference between a first location in the BGE reservoir and a second position downstream from the first position.

The second/(b) step can be carried out so that the concurrent pressures applied to the sealed headspaces of the BGE reservoir and the sample reservoir are each between 0.5 psi and 50 psi, and the third/(c) step can be carried out so that no pressure is applied to the sealed headspace of the sample reservoir and the pressure applied to the sealed headspace of the BGE reservoir to flush the sample is between 0.1 psi and 10 psi.

The fluidic device can include: a first pressure supply tube in communication with a first pressurized gas source and connected to a sealed headspace of the BGE reservoir through a first valve; a second pressure supply tube in communication with the first pressurized gas source or a second pressurized gas source and connected, through a second valve, to a sealed headspace of a sample reservoir in fluid communication with the sample channel; and a third pressure supply tube in fluid communication with one of the first pressurized gas source, the second pressurized gas source, and a pressure-reducing device, and connected to a sealed headspace of a waste reservoir through a third valve. The waste reservoir can be in fluid communication with a waste channel (which may optionally be across from the sample channel), and in fluid communication with the separation channel. The method can further include: electronically opening and closing the first, second and third valves in a defined sequence to flow the sample through the sample channel, across the at least one SPE bed, and into the separation channel.

The method can further include: capturing ions of the analyte component in a mass spectrometer; detecting electronic signals corresponding to the captured ions; and generating mass spectral information corresponding to the analyte component based on the electronic signals.

Still other embodiments are directed to microfluidic analysis systems. The systems include: a microfluidic device comprising at least one separation channel in fluid communication with a background electrolyte (BGE) reservoir, a sample channel in fluid communication with a sample reservoir and the separation channel and including at least one solid phase extraction (SPE) bed, and a waste reservoir in fluid communication with the separation channel. The systems also include: a first gas supply tube that connects a first pressurized gas supply to a sealed headspace of the BGE reservoir through a first valve; a second gas supply tube that connects a second pressurized gas supply to a sealed headspace of the sample reservoir through a second valve; and a third gas supply tube that connects a third pressurized gas supply or a pressure-reducing device to a sealed headspace of the waste reservoir through a third valve. The waste reservoir is in fluid communication with a waste channel that fluidly connects the waste reservoir to the separation channel. The systems also include: an electrode extending into the BGE reservoir so that when fluid is present in the BGE reservoir, the electrode contacts the fluid; and a controller in electrical communication with a voltage source and with the first, second and third valves. The controller is configured so that during operation of the system, the controller directs the first, second and third valves to open and close to flow a sample through the sample channel, across the at least one SPE bed and into the separation channel, and electrophoretically separate an analyte component in the separation channel, without applying an electrokinetic voltage and/or a voltage gradient across the sample channel and/or SPE bed.

The sample channel can include at least one blocking member positioned adjacent to an end of the at least one SPE bed that is closest to the separation channel to retain SPE material within the SPE bed.

The SPE bed has a length, measured along a flow direction defined by the sample channel, that can be between 100 μm and 1000 μm, and a volume that can be between about 50 pL to about 10 nL.

The sample channel can be valveless so that the SPE bed is in uninterrupted fluid communication with the separation channel.

Some embodiments are directed to mass spectrometry systems that include a mass spectrometer and a microfluidic device onboard or in communication with the mass spectrometer. The microfluidic device includes at least one separation channel in fluid communication with a background electrolyte (BGE) reservoir, a sample channel in fluid communication with the separation channel, a sample reservoir in fluid communication with the sample channel, a waste channel in fluid communication with the separation channel, a waste reservoir in fluid communication with the waste channel, and at least one electrospray ionization (ESI) emitter in fluid communication with the separation channel. The sample channel includes at least one solid phase extraction (SPE) bed. The system further includes: a first conduit in communication with a first valve coupled to the BGE reservoir; an electrode extending into the BGE reservoir so that when fluid is present in the BGE reservoir, the electrode is in electrical communication with the fluid; a second conduit in communication with a second valve coupled to the sample reservoir; a third conduit in communication with a third valve coupled to the waste reservoir; at least one voltage source electrically connected to the electrode; a first gas source in fluid communication with the first and second conduits; a second gas source or a pressure-reducing device in fluid communication with the third conduit; and a controller in electrical communication with the first gas source, the second gas source or pressure-reducing device, and the at least one voltage source. The controller is configured so that during operation of the system, the controller: (i) applies a pressure to a headspace of the waste reservoir through the third conduit and concurrently applies a pressure to a headspace of the sample reservoir through the second conduit such that the pressure applied to the headspace of the waste reservoir is less than the pressure applied to the headspace of the sample reservoir; (ii) concurrently applies pressures to the headspaces of the sample reservoir and the BGE reservoir without applying a voltage to fluid in the sample reservoir or to fluid in the BGE reservoir; then (iii) reduces the pressure applied to the headspace of the sample reservoir so that the pressure then applied to the BGE reservoir is greater than the pressure applied to the sample reservoir to transport the sample and fluid from the BGE reservoir into the at least one separation channel; then (iv) applies an electric field along the separation channel using the at least one voltage source to electrophoretically separate an analyte component from the sample; and then (v) perform electrospray ionization of the analyte component using the at least one ESI emitter to direct ions of the analyte component toward a collection device or an inlet of the mass spectrometer The sample channel can include at least one blocking member positioned adjacent to an end portion of the at least one SPE bed that is closest to the separation channel.

The SPE bed has a length, measured along a flow direction of the sample channel toward the separation channel, that can be between 100 μm and 1000 μm, a volume that can be between about 50 pL and about 10 nL, and can have a leading end positioned a distance of between 10 μm and 5 cm upstream from the separation channel.

The sample channel can be valveless so that the SPE bed is in uninterrupted fluid communication with the separation channel.

Still other embodiments are directed to fluidic devices that include: at least one microfluidic or nanofluidic separation channel in fluid communication with a background electrolyte (BGE) reservoir; at least one nanofluidic or microfluidic sample channel in fluid communication with a respective one of the at least one microfluidic or nanofluidic separation channel; at least one solid phase extraction (SPE) bed in a corresponding one of the at least one nanofluidic or microfluidic sample channels, positioned adjacent to a respective one of the at least one microfluidic or nanofluidic separation channels, so that a leading end of the at least one SPE bed is positioned between 10 µm and 5 cm from the separation channel; and at least one nanofluidic or microfluidic waste channel that extends from a respective one of the at least one separation channel and is positioned across from a respective one of the at least one sample channel.

The device can include at least one blocking member positioned adjacent to an end of the at least one SPE bed that is closest to a respective one of the at least one separation channels so that it at least partially occludes a respective one of the at least one sample channels.

The leading end of the at least one SPE bed can be positioned at a distance of between 50 µm and 500 µm from the corresponding one of the at least one separation channels.

A width of the at least one SPE bed can be greater than a depth of the at least one SPE bed. The width being measured in a plane defined by the device and in a direction orthogonal to a flow direction defined by the at least one sample channel within the plane. The depth being measured in a direction orthogonal to the plane and to the flow direction.

The at least one SPE bed has a length, measured along the flow direction, that can be between 100 µm and 1000 µm, and a volume that can be between about 50 pL and about 10 nL.

The device can include at least one electrospray ionization emitter in fluid communication with the at least one separation channel.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 6A is a schematic illustration of a fluidic device according to embodiments of the present invention.

FIGS. 6B and 6C are schematic, enlarged partial cutaway views of sample flow channels with SPE bed blocking members according to embodiments of the present invention.

FIGS. 6D, 6E and 6F are schematic, enlarged cross-sectional views of exemplary sample flow channels with blocking members according to embodiments of the present invention.

FIG. 12A is an electropherogram of a CE-ESI of 5 µM sample. FIG. 12B is an electropherogram of an SPE-CE-ESI of 50 nM sample. FIG. 12C is an electropherogram of an SPE-tITP-CE-ESI of 50 nM sample. A and B correspond to unidentified trace components.

FIGS. 13A and 13B are electropherograms of a four peptide mix. FIG. 13A was generated using electrokinetic (EK) injection and FIG. 13B was generated using hydrodynamic injection according to embodiments of the present invention.

FIG. 14 is a graph of peak area ratio versus CE (capillary electrophoresis) migration time from the gated injection relative to peak areas for EK and hydrodynamic driven injections.

FIGS. 16A-16C are plots of peak area, width and height versus sample concentration (nM) for SPE-tITP-CE-ESI analysis of Bradykinin according to embodiments of the present invention.

FIGS. 17A-17C are plots of peak area, width and height versus sample concentration (nM) for SPE-tITP-CE-ESI analysis of Thymopentin according to embodiments of the present invention.

FIGS. 18A-18C are plots of peak area, width and height versus sample concentration (nM) for SPE-tITP-CE-ESI analysis of peptide A according to embodiments of the present invention.

FIGS. 19A-19C are plots of peak area, width and height versus sample concentration (nM) for SPE-tITP-CE-ESI analysis of Angiotensin II according to embodiments of the present invention.

FIGS. 20A-20C are plots of peak area, width and height versus sample concentration (nM) for SPE-tITP-CE-ESI analysis of Met-Enkephalin according to embodiments of the present invention.

FIGS. 21A-21C are plots of peak area, width and height versus sample concentration (nM) for SPE-tITP-CE-ESI analysis of Peptide B according to embodiments of the present invention.

DESCRIPTION OF EMBODIMENTS OF THE INVENTION

Figure 1A:
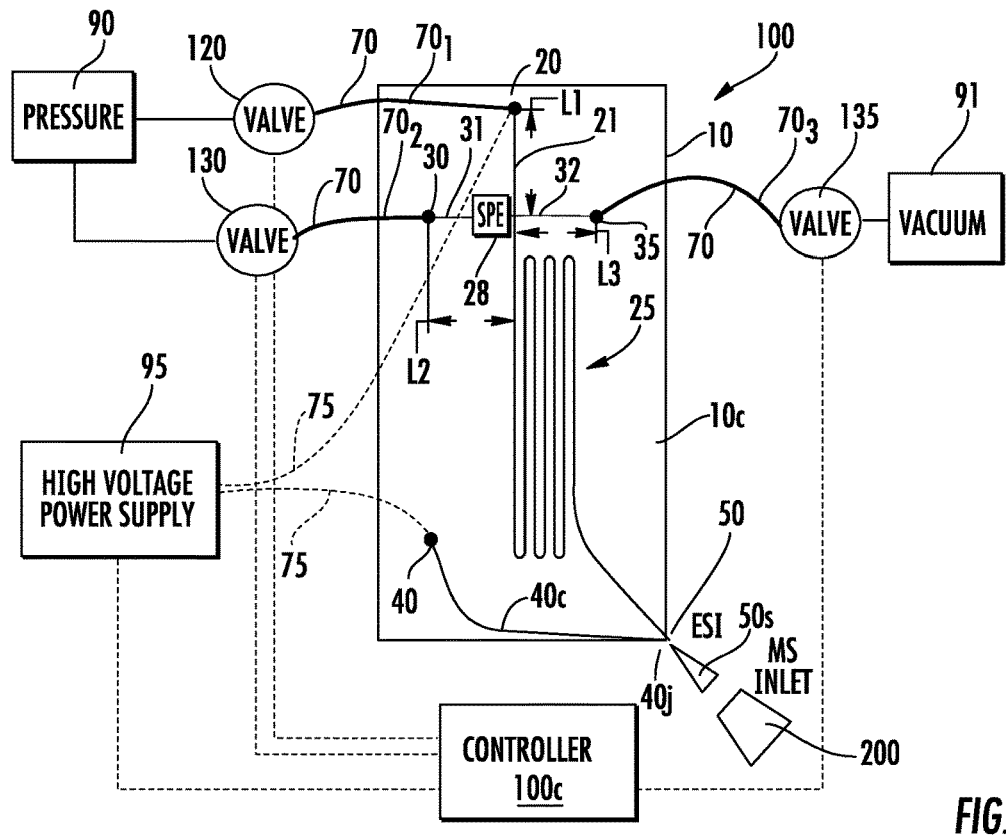
FIG. 1A is a schematic illustration of a fluidic analysis system according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. The abbreviations "FIG. and "FIG." for the word "Figure" can be used interchangeably in the text and figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. Well-known functions or constructions may not be described in detail for brevity and/or clarity.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The term "about" means that the stated number can vary from that value by +/−20%.

The term "analyte" refers to a molecule or substance undergoing analysis, typically, at least for mass spectrometry analysis, having an ion or ions of interest in a mass-to-charge (m/z) range of interest. The analyte can comprise biomolecules such as polymers, peptides, proteins and the like. Embodiments of the invention are particularly suitable for analyzing intact monoclonal antibodies. Embodiments of the invention are particularly suitable for analyzing metabolites.

The term "pre-concentration" refers to analytes at increased concentration relative to a concentration at introduction to a fluidic analysis device or system so that a sample with the analytes is processed, typically prior to introduction into a separation channel, to contain analytes at higher concentrations relative to concentration(s) when introduced to the system, device, or process, i.e., as introduced to a sample channel or reservoir upstream of the SPE bed and/or separation channel. The term "pre-concentrating" refers to processes, typically on-chip processes, that achieve the pre-concentration. The term "focusing" refers to performing the pre-concentrating using electrokinetic techniques.

The term "microchip" refers to a substantially planar, thin, and, in some embodiments, rigid fluidic device. The term "thin" refers to a thickness dimension that is less than about 10 mm, typically about 1 mm or less. The microchip typically has a width and length that is less than about 6 inches and a thickness that is less than about 5 mm, typically between about 2000 µm to about 250 µm.

The terms "integrated" and "integral" and derivatives thereof means that the component and/or process or action is incorporated into or carried out by a fluidic device. For example, an integrated SPE-tITP-CE-ESI microfluidic device has an onboard SPE bed, a CE channel, at least one an ESI emitter can perform tITP.

The term "in-line coupling" refers to the inclusion of a solid phase extraction (SPE) sorbent(s) proximate or adjacent an entry to the CE capillary (also called a separation channel), typically via a side or cross-channel at a head or ingress end portion of the CE capillary.

The term "SPE bed" refers to a segment of a fluid channel that holds a volume of SPE material (i.e., sorbent) in a suitable density so that sample flows through the bed prior to entering the separation channel.

The term "high voltage" refers to voltage in the kV range, typically between about 1-100 kV, more typically between about 1-20 kV. ESI processes can employ potentials of a few kVs, typically between about 1 kV to about 5 kV, for example. Other voltages may be appropriate.

The term "microfluidic" refers to fluid flow channels that have sub-millimeter or smaller size width and/or depth (e.g., the term includes nanometer size channels) and includes channels with width and/or depth dimensions in a size range of about tens to hundreds of microns.

The term "hydrodynamic driven injections" refers to pressure controllably applied to one or more fluid channels to transport a target sample for analysis to a separation channel without requiring voltage.

All of the document references (patents, patent applications and articles) are hereby incorporated by reference as if recited in full herein.

In typical free zone capillary electrophoresis (CE) experiments, a sample plug is injected into a column, and an applied electric field causes sample components to separate according to differences in their mobilities. The mobility of a molecule is the sum of its electrophoretic mobility and the electroosmotic mobility, and any driven flow, if present, of the separation column.

The term "plug" with respect to "sample" refers to a quantity of a sample collected/localized within a spatial region, such as within a spatial region of a carrier fluid. The plug can be a physical band or segment with defined leading and trailing ends so that there is a distinct clearance between successive plugs or bands.

The term "separated sample" refers to the electrophoretically separated sample and/or components of a sample mixture (i.e., spatially separated along the axial extent of the separation channel) and may or not be separated into individual components. Components will be separated based upon their effective electrophoretic mobilities and separation of components will depend on the difference in effective mobilities. The separated sample can be detected by observing the spatial separation in the separation channel and/or by observing their arrival times at the electrospray emitter or detector. Effective electrophoretic mobility is defined as the observed velocity in the separation channel divided by the electric field strength in the separation channel and will include the actual electrophoretic mobility and the vector sum of any other effect imparting velocity to the component including, but not limited to, electroosmotic or pressure driven transport. The "sample" can comprise a collection of one or more different components (i.e., an analyte and surrounding matrix material). The sample is introduced into the fluidic device. During separation, an "analyte component (s)" of the sample can be separated for analysis from other components.

The analyte in a sample can be any analyte of interest including, for example, various mixtures including synthetic and biological macromolecules, nanoparticles, small molecules, DNA, nucleic acids/polynucleic acids, peptides, proteins and the like. The sample can include one or more polar metabolites such as amino acids or charged molecules, molecules, peptides, and proteins. The sample may also or alternatively include molecules extracted from biofluids, blood, serum, urine, dried blood, cell growth media, lysed cells, beverages or food; or environmental samples such as water or soil.

Low pH refers to acidic levels (below 7) and high pH refers to basic levels (above 7).

The term "low organic" refers to levels at or below 25% by volume and "high organic" refers to levels above 25% by volume.

With respect to certain processing conditions associated with SPE, low salt content refers to between 0-0.1 M salt content, while high salt content can refer to above 0.1, such as above 0.1 M to about 1 M salt content.

Referring to FIG. 1A, an exemplary analysis system 100 with a fluidic device 10 at a controller 100c is shown. The controller 100c can include at least one processor that can be configured to direct the system 100 to operate with a sequence of operations, such as a sequence of voltage and/or pressure inputs to components of the fluidic device 10. The fluidic device 10 can be a microchip 10c. The fluidic device 10 can include at least one separation channel 25 (which can also be interchangeably referred to as a capillary channel) and at least one solid phase extraction (SPE) bed 28 in fluid communication with the separation channel 25.

The SPE bed 28 can reside in a side channel 31 that connects to an upstream, upper end portion or ingress end portion 25u of the separation channel 25. The side channel 31 can be orthogonal to the separation channel 35 or may reside at other angles (see, e.g., FIG. 4D). The SPE bed 28 can reside between the separation channel 25 and a reservoir 30. The reservoir 30 can be configured to supply defined fluids, such as a sample fluid for analysis, to the SPE bed 28, which flows over or through the SPE bed 28, then to the separation channel 25. The SPE bed 28 can be pre-packed or formed prior to an analysis, such as provided in a device ready for use, or may be packed in situ prior to and/or as part of an analysis. The fluidic channel 31 holding at least one SPE bed 28 can include at least one blocking member 128, such as a weir 128, or membrane. In some embodiments, the blocking member 128 can be other fluid permeable, which may be particularly suitable for embodiments where the blocking member 128 extends totally across the sample inlet channel 31. The blocking member 128 is configured to allow fluid, such as a liquid or gas sample S to flow through or over the SPE bed 28 while inhibiting SPE material from the bed 28 from entering the separation channel 25. The term "weir" refers to structures with an obstruction across a width or partial width of the sample inlet channel 31. In some embodiments, the blocking member 128 resides between the end of the SPE bed 28e and the separation channel 25, typically adjacent the separation channel, such as, for example, within about 10 µm to under 5 cm, typically between 10 µm to about 500 µm, and more typically between about 50 µm to about 500 µm from the separation channel 25.

As shown in FIG. 6A, the side channel 31 (which can also be referred to interchangeably as "a sample inlet channel") can be configured to have separate segments that merge into the sample inlet channel with the at least one blocking member 128. If so, separate reservoirs $30_1$, $30_2$ may connect to a different branch $31a$, $31b$. The branches $31a$, $31b$ can fluidly merge into the channel 31. One reservoir $30_1$ can comprise the sample S and another $30_2$ can hold SPE material $28s$ and/or other fluids for processing (e.g., wash or solvent and the like). Each branch/reservoir pair $30_1/31b$, $30_2/31a$ can serially flowably introduce material to the inlet side channel 31.

The blocking member 128 can extend down from the ceiling $31c$ ($128_1$, FIG. 6B) or up from the floor $31f$ (FIGS. 2B, 6F) and/or extend inwardly from sidewalls $31s$ (FIGS. 6D, 6E). The at least one blocking member 128 can be a plurality of blocking members $128_1$, $128_2$ (up to $128n$, where n=1 to 10) extending from two of the ceiling $31c$, floor $31f$ or sidewalls $31s$ ($128_1$, $128_2$, FIG. 6B, $128_1$-$128_4$, FIGS. 6E, 6D). The at least one blocking member 128 can have a height that is less than a depth dimension of the channel 31, typically between about 30-70% of the depth dimension. For example, for a channel 31 with a depth dimension of 100 µm, the height of the blocking member 128 can be between 30 and 70 µm, such as about 30 µm, about 40 µm, about 50 µm, about 60 µm, and about 70 µm. As shown in FIG. 6B, where two or more blocking members $128_1$, $128_2$ are used for a respective bed 28, the two can be offset yet closely spaced apart (typically between about 1-20 µm) from each other. In other embodiments, at least two of the blocking members $128_1$, $128_2$ can be directly aligned from each other as shown in FIG. 6C.

FIGS. 6D-6F illustrate examples of sample channel geometries which may be formed by etching, milling, molding and the like. The number and placement of the at least one blocking member 128 are by way of illustration only.

As shown in FIG. 6A, the fluidic device 10 comprises a planar rigid, semi-rigid or flexible (polymeric) ceiling $10c$ that is sealably attached to a substrate $10s$ holding the fluid channels 21, 25, 31, 32, typically in multiple sets, to seal the fluid channels. The blocking member(s) 128 can be integrally formed in the sample inlet channel 31 or be attached as a separate component, where more than one are used combinations of integral and separate components can be used.

The SPE bed 28 can comprise any suitable solid phase extraction material and/or sorbent including mixtures of different materials. The SPE bed 28 can comprise, for example, small particles having a diameter and/or a maximal height/width or length dimension that is less, typically at least 30% less, than the width/depth of the fluidic channel 31 holding the bed 28. The SPE bed 28 can comprise 5 µm diameter porous Oasis HLB particles. Other particle types suitable for SPE beds 28 include, but are not limited to, reverse phase, ion exchange, immuno sorbent, HILIC, normal phase and mixed mode. An example of mixed mode is Water's Oasis HLB particles. A few examples of each type (to be clear this is not an exhaustive list) are provided below.
Revered Phase—C4, C8, C18, Phenyl
HILIC—bare silica
Ion Exchange—Titanium Dioxide for phosphopeptides,
Affinity—antibody, lectins for glycopeptides, Nickle-His tag In some embodiments, the SPE material for the SPE bed 28 can include a retentive reversed-phase material and/or a mixed mode stationary phase, such as a combined reversed-phase retention with ion exchange retention. See, e.g., Gilar et al., *Journal of Chromatography A* 2008, 1191, 162-170; and Li et al., *Talanta* 2015, 140, 45-51. The contents of these documents are hereby incorporated by reference as if recited in full herein.

The SPE bed 28 can have any suitable size, density and volume. In some embodiments, the length of the SPE bed 28 can be between 1 µm and 1 cm, typically between 100 µm and 1000 µm, such as about 100 µm, about 200 µm, about 300 µm, about 400 µm, about 500 µm, about 600 µm, about 700 µm, about 800 µm, about 900 µm and about 1000 µm long. The length of the SPE bed 28 can be less than the fluidic channel 31 in which it resides, typically between 2-1000× less. The SPE bed 28 typically resides closer to separation channel 25 than the reservoir 30. The leading end (the end closest the separation channel 25) of the SPE bed 28 can reside within about 10 µm to under 5 cm, typically between 10 µm to about 500 µm, and more typically between about 50 µm to about 500 µm from the entry or boundary of the separation channel 25. The width of the fluid channel 31 holding the SPE bed 28 can be greater than the depth, typically 2-200× greater. The volume of a (packed) SPE bed 28 can be between about 50 pL to about 10 nL, such as about 425 pL, in some embodiments.

The SPE bed 28 can be packed in the sample channel 31 prior to analysis of a sample S. An SPE slurry can be flowably introduced into the sample channel 31. The term "slurry" refers to a viscous solution of SPE material. The viscosity of the SPE slurry is greater than the viscosity of other liquids used for the analysis.

In some embodiments, a low concentration of an ion-pairing agent such as Trifluoroacetic acid (TFA) can be introduced into the fluid channel 31 and the SPE bed 28 to retain a sample S. Where TFA is used, it can be provided in a concentration between about 0.01% to about 1% by volume. This agent can be introduced before and/or with the introduction of a sample into the channel 31. The TFA can be removed (e.g., washed into the waste channel 32 and/or waste reservoir 35) prior to elution for introducing the sample as a sample plug in the separation channel. Any Ion-Pairing agent current used in chromatography may be used for SPE with this device, depending on the chemistry of the SPE sorbent and the identity of the sample. Ion-exchange chromatography systems have previously been utilized in HPLC analysis of ionic samples including phase partition chromatography using ion-pair reagents. The ionic samples form an ion-pair with ion-pair reagents in the mobile phase to become electrically neutral. The increase in hydrophobic character of the ion-pair results in a greater affinity for the reverse stationary phase and leads to sample resolution.

Acidic Sample

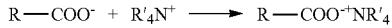

Basic Sample

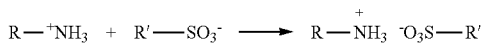

See, e.g., the below webpage with different examples of ion-pairing agents: http://www.teichemicals.com/eshop/en/us/category_index/00418/#innerlink_10_1_1, the contents of which are hereby incorporated by reference as if recited in full herein.

The ion-pairing agent can be pre-loaded into the fluid channel 31 (or onto the material of the SPE bed 28) or added in situ during or just prior to an analysis, for example.

Still referring to FIG. 1A, the system 100 can include a voltage supply 95, which may be a high voltage supply. As shown, the system 100 can also include at least one pressurized gas source 90 in communication with the BGE reservoir 20 and the side reservoir 30 via supply lines/conduits 70 and respective valves 120, 130. The BGE reservoir 20 can feed a BGE channel 21 that is connected to the separation channel 25.

As shown, the system 100 can include a pressure reducing device 91 in communication with a waste reservoir 35 which may also be connected via a respective valve 135. The pressure-reducing device 91 can have an active or passive configuration, i.e., can comprise a vacuum, a pump, an evacuated reservoir, or any other enclosed volume at a pressure less than the pressure applied to the BGE reservoir 20 and/or the side reservoir 30, typically less than ambient pressure, that will reduce the pressure in the headspace of the waste reservoir 35 once connected.

While shown as a separate device 91, the pressure reducing device 91 can be configured with a supply line 70 to connect the waste reservoir 35 to the first pressurized gas source 90 and pressure can be controlled to provide the desired input. Also, the pressure reducing device 91 is not required to be a vacuum and may operate at different pressures to provide the desired operational sequence as will be discussed further below.

The waste reservoir 35 can be in fluid communication with the separation channel 25. The waste reservoir 35 can reside in a second side channel 32. The waste channel 32 can reside across from the side channel 31 with the SPE bed 28. The waste channel 32 can be laterally in line with the side channel 31 (i.e., FIG. 4A) or can be longitudinally offset from the side channel 31 (i.e., FIG. 4C).

The background electrolyte (BGE) reservoir 20 can reside at a top above the separation channel 25. The BGE reservoir 20 can reside directly adjacent the separation channel or may have a BGE flow channel 21 that merges into the separation channel 25 to position the BGE reservoir 20 a distance away from the sample channel 31 and the sample waste channel 32.

In the embodiment shown in FIG. 1A, the fluidic device 10 has cross channels defined by the sample channel 31 and the sample waste channel 32, which can reside on opposing sides of the separation channel 25 and may optionally be orthogonal to and extend across to intersect the separation channel 25.

In some embodiments, defined pressures can be supplied by the pressurized gas supply 90 and/or 91 to the respective gas supply lines 70 which are sealably attached to respective reservoirs 20, 30, 35, typically conduits or lengths of tubing 70 from at least one pressurized gas source 90. The pressurized gas of the gas supply 90 for providing pressure-driven injection can comprise air and/or noble gases such as helium or nitrogen or other inert gases. FIG. 1A illustrates discrete valves 120, 130, 135 for the gas supply lines $70_2$, $70_1$, $70_3$ respectively. Any or all of valves 120, 130, 135 can be three-way valves.

It is also noted that while the system 100 is shown with three reservoirs 20, 30, 35, less or more reservoirs and, indeed, side channels, may be used.

FIG. 1A also illustrates that the fluidic device 10 can include a pump 40 and at least one electrospray ionization (ESI) emitter 50 that can spray a separated sample 50s for analysis. The pump 40 can include a channel 40c that extends to a junction 40j adjacent the ESI emitter 50. The electrospray 50s from the at least one emitter 50 can be provided to a collection device 202 (FIG. 7A) for subsequent analysis and/or toward an entrance aperture/inlet of a mass spectrometer 200 with a detector (FIG. 1A). The pump can optionally comprise an electroosmotic (EO) pump.

Figure 1B:
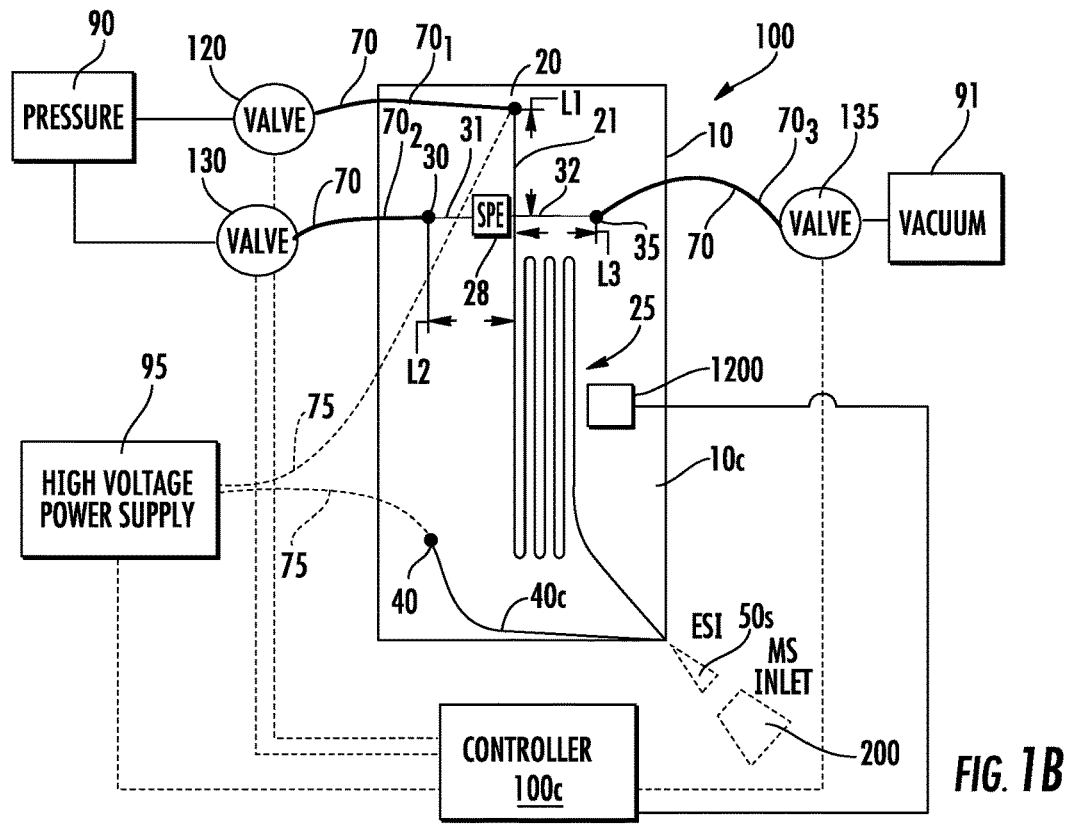
FIG. 1B is a schematic illustration of another embodiment of a fluidic analysis system according to embodiments of the present invention.

FIG. 1B illustrates that the analysis system 100 can include the fluidic device 10 with the at least one SPE bed 28 and may also include at least one detector 1200 to obtain signal from the sample in the separation channel 25. The fluidic device 10 may be configured without the at least one ESI emitter 50 and may be used without requiring the input to the mass spectrometer 200. The detector 1200 can be an electronic detector such as an optical detector and/or a conductance detector (i.e., comprising an ammeter), for example. Where used, the optical detector 1200 can comprise an avalanche photodiode and laser, or photomultiplier and convention light source such as a blackbody source or discharge source, or any combination of the above as is well known to those of skill in the art. The detector 1200 can obtain signal for qualitative and/or quantitative data of a sample in the separation channel 25. In some embodiments, the analysis system 100 can include both the at least one detector 1200 and the at least one ESI emitter 50 for input to the inlet/entrance aperture of the mass spectrometer 200. In some embodiments, both mass spectrometer detection and optical detection by the detector 1200 can be carried out simultaneously, i.e., signal from the ESI emitter 50 the inlet of the mass spectrometer 200 can be obtained while signal from the detector 1200 is obtained for a respective sample, for example.

The separation channel 25 is shown in FIGS. 1A and 1B as having a serpentine shape but other configurations may be used. For example, the geometry of the separation channel 25 can be straight or curved, and the cross-sectional profiles of the channels do not all have to be the same. For further discussion of exemplary microfluidic devices, see, e.g., U.S. patent application Ser. Nos. 14/001,549 and 14/368,971, the contents of which are hereby incorporated by reference herein.

The fluidic (sample) channel 31 holding the SPE bed 28 can have a width and/or depth that is between 40 nm and 1000 μm, more typically between about 1 μm and about 100

μm, such as a channel depth and width of about 10 μm (depth) and 70 μm (width), respectively. As used herein, the "width" of channel 31 is measured in the plane of device 10 (i.e., in the plane defined by the microfluidic chip) and in a direction that is perpendicular to an axis of channel 31, where fluid flow occurs through channel 31 in a direction parallel to the axis. As used herein, the "depth" of channel 31 is measured in a direction perpendicular to the plane of device 10 and to the direction along which the width is measured. The fluidic channels 21, 31 and 32 can all have the same depth or may have different depths. The fluidic channels 21, 31 and 32 can have the same width or different widths. The separation channel 25 can have any suitable length, typically between 1 cm to 100 cm, more typically between about 20-30 cm, such as about 23 cm.

As shown in FIGS. 1A and 1B, for example, the sample channel 31 is valveless so that the SPE bed 28 remains in fluid communication with the separation channel 25 continuously, i.e., the fluid device 10 does not require any valve to isolate the SPE bed 28 from the separation channel 25. Stated differently, the at least one SPE bed 28 is held in the sample channel 31 and in the sample flow path without requiring any valve to isolate the SPE bed 28 during in-line operation.

The BGE reservoir 20 can be at the top of the separation channel 25 (directly or via the BGE channel 21). The BGE channel 21 can have a length "$L_1$" (FIGS. 1A, 1B) extending from the BGE reservoir 20 to the SPE bed channel 31 (which can also be called the "sample channel" as the sample is introduced into this channel to contact the SPE bed 28 prior to entering the separation channel 25) and/or the channel 31 and waste channel 32 cross/intersection with the separation channel 25. The length "$L_1$" can be any suitable length, such as, for example, between 1-200 mm long. The SPE bed channel 31 can have a length "$L_2$" (FIGS. 1A, 1B) and the waste channel 32 can have a length "$L_3$" (FIGS. 1A, 1B). Also, the lengths $L_1$, $L_2$, $L_3$ of one or more of the channels 21, 31, 32, can be any suitable length such as about 1 mm, about 5 mm, about 10 mm, about 20 mm, about 30 mm, about 40 mm, about 50 mm, about 60 mm, about 70 mm, about 80 mm, about 90 mm, or about 100 mm, in some embodiments, but other lengths can be used. In general, the "length" of a channel (such as the lengths $L_1$, $L_2$, and $L_3$ referenced above) is measured along an axis of the channel in a plane of device 10 (i.e., in the plane defined by the microfluidic chip), where fluid flow occurs through the channel in a direction parallel to the axis. Where used, the injection cross configuration may be such that channels 21, 31 and 32 have substantially the same length or different lengths, but typically lengths that are much less than the length of the separation channel 25. The sample and sample waste channels 31, 32, can be longer or shorter than the BGE channel 21 and may, for example, be between 1 mm and 5 cm, typically between about 1-100 mm long. In some embodiments, the sample and sample waste channels 31, 32 are between about 1-20 mm, such as about 8 mm in length.

One or both of the reservoirs 20, 30 can be in fluid communication with one or more external fluid sources to provide fluid thereto during analysis and/or one or both of the reservoirs 20, 30 may be pre-loaded prior to active analysis.

Still referring to FIG. 1A, in some embodiments, a fluid junction 40j can be used to connect the separation/transfer channel 25 and respective pump channel 40c. The fluid junctions can be nanojunctions with the associated nanojunction channels having nanometer-sized depths. The pump channel 40c and/or separation channel 25 can have microm-eter-sized widths. The junctions 40j can have, for example, a depth of about 50 nm and a width of about 50 μm. The depth of the channel may be dictated by the ionic strength of the buffers used in the experiment/analysis and the corresponding Debye lengths. Nanochannel depth should be on the order of the Debye length or smaller.

Figure 2A:
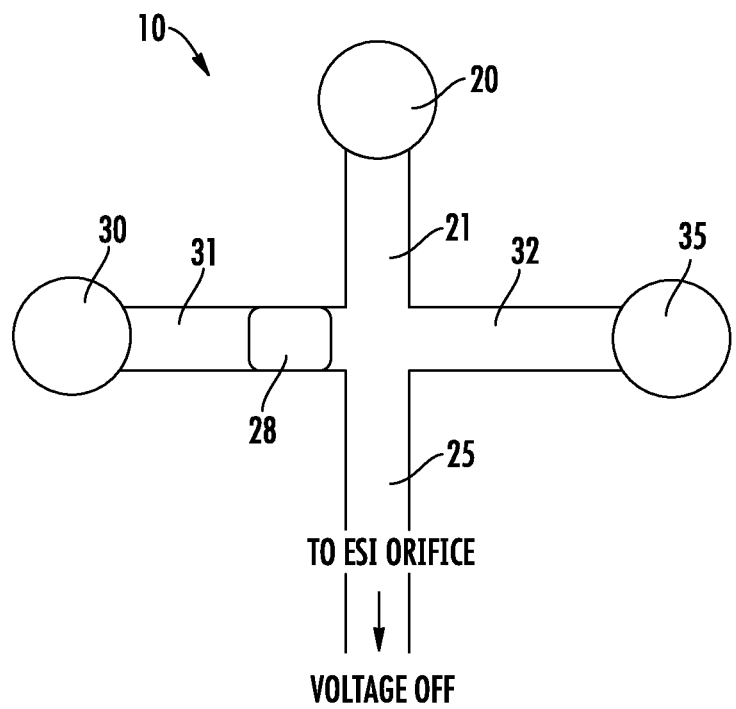
FIGS. 2A-2H are schematic illustrations of a sequence of events for a microfluidic device used to inject sample into a separation channel according to embodiments of the present invention.
Figure 2B:
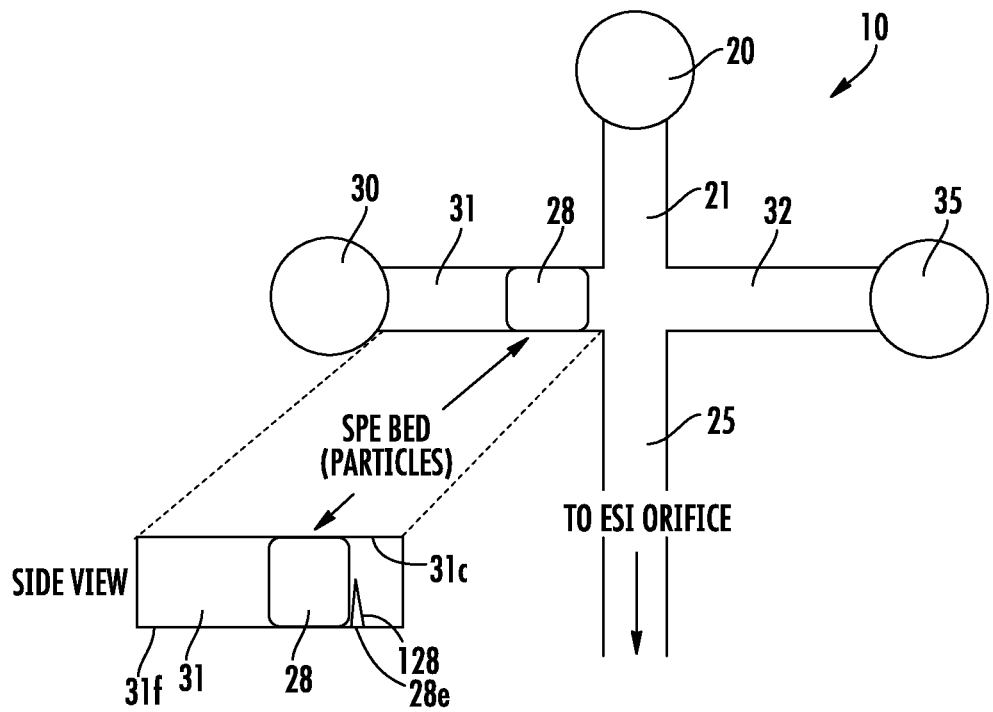

FIGS. 2A-2H and 3A-3F, illustrate an exemplary sequence of operations that can be carried out according to some embodiments of the present invention. FIGS. 2A and 2B show that a fluidic device 10 can be provided and a SPE bed 28 can be loaded or pre-loaded for use. FIG. 2B shows the fluidic channel 31 with the SPE bed 28.

Figure 2C:
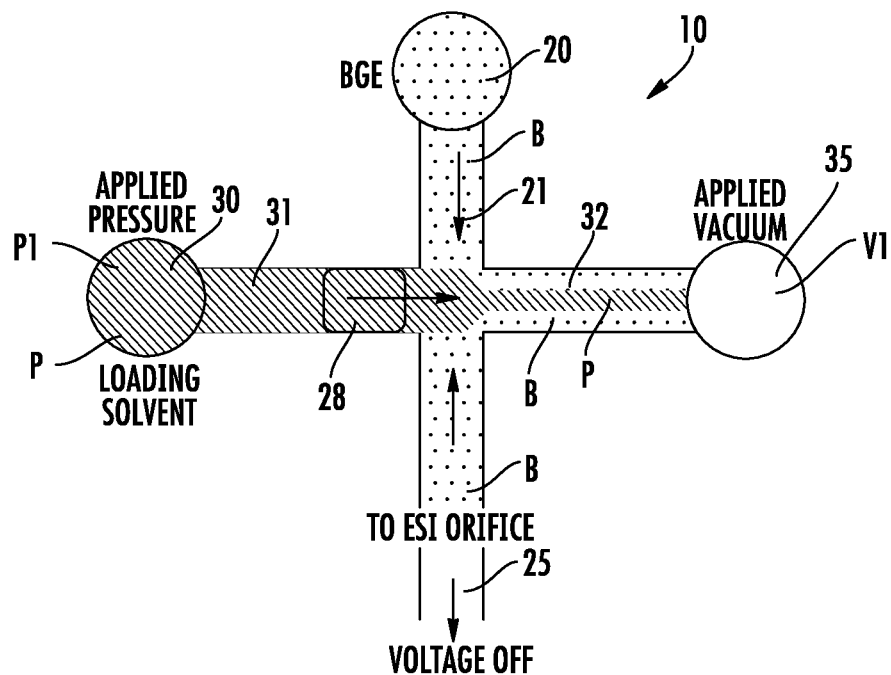
Figure 3A:
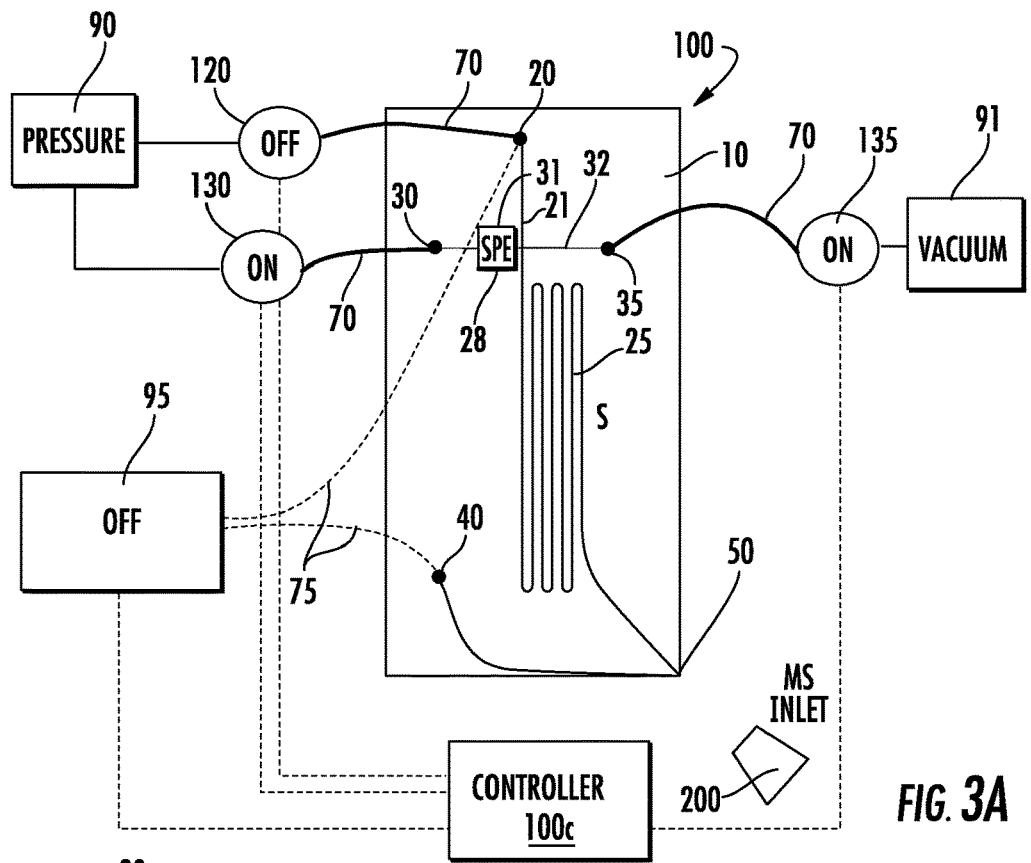
FIGS. 3A-3F are schematic illustrations of the fluidic analysis system shown in FIG. 1A, illustrating exemplary operative states of pressure and voltage inputs according to embodiments of the present invention.

FIGS. 2C and 3A illustrate a pre-conditioning of the SPE bed 28 can be carried out. FIG. 2C shows a pre-conditioning fluid P such as a solvent from the reservoir 30. FIGS. 2C and 3A illustrate a pressure driving input P1 applied to the reservoir 30 while a pressure reducing device applies a reduced pressure such as a vacuum V1 to the waste reservoir 35 and voltage is OFF. FIG. 3A illustrates the valves 130 and 135 are ON while valve 120 is OFF and the voltage is OFF (i.e., not applied to inputs 20 or 40). While the pressure is shown as OFF for valve 120/pressure input to reservoir 20, a pressure may be applied but not sufficient to interfere with the operational inputs. The pre-conditioning fluid P from the reservoir 30 flows across/through the SPE bed 28 and into the waste channel 32, then to the waste reservoir 35. BGE solution B can flow from the BGE reservoir 20. The flow direction of the pre-conditioning fluid P and BGE fluid B are indicated by the flow direction arrows in FIG. 2C.

The term "pre-condition" refers to exposing the SPE bed 28 to any solvent or liquid mixture of an appropriate organic content, pH, and/or salt content. The pre-conditioning agent or mixture may change based on the chemistry of the SPE sorbent and the identity of the sample S. The pre-conditioning material can be a defined liquid that can: optionally a) wet the SPE bed (although this is less of a concern with the microchip if the bed has been wetted during the chip filling step) and/or b) condition the SPE bed 28 to be in a desired current solvent condition that is suitable/appropriate for binding the target sample S. For example, in reversed phase SPE, loading can occur under low organic conditions. Therefore, the pre-conditioning step can be used to ensure that the SPE bed 28 is wetted or exposed to low organic solvent. As another example, loading using a HILIC stationary phase occurs under high organic conditions. Loading with ion-exchange may occur under low salt, while elution occurs at high salt. In some embodiments, pH can also affect loading and elution.

Figure 2D:
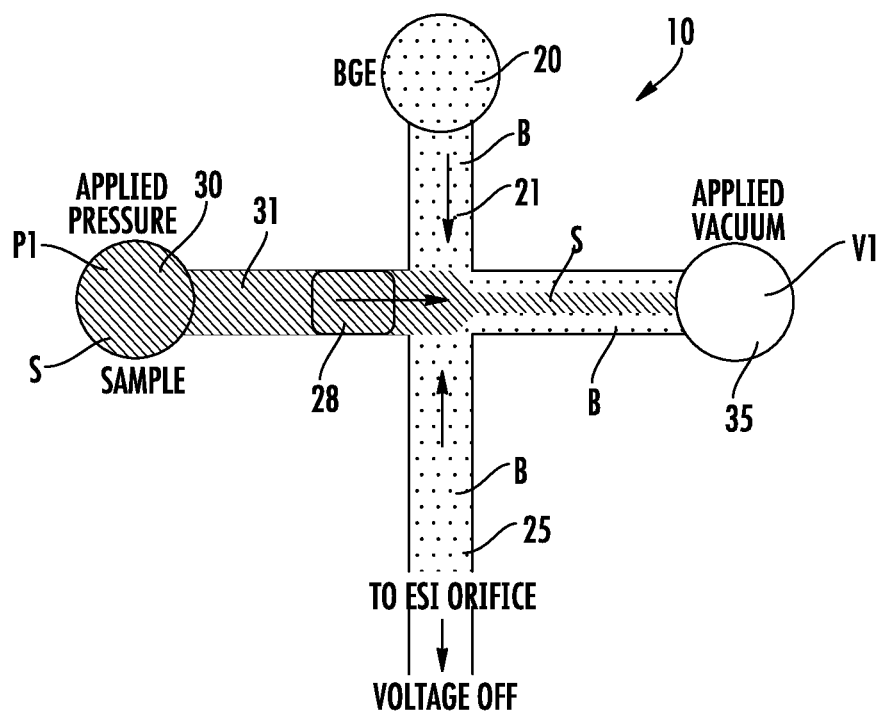
Figure 2E:
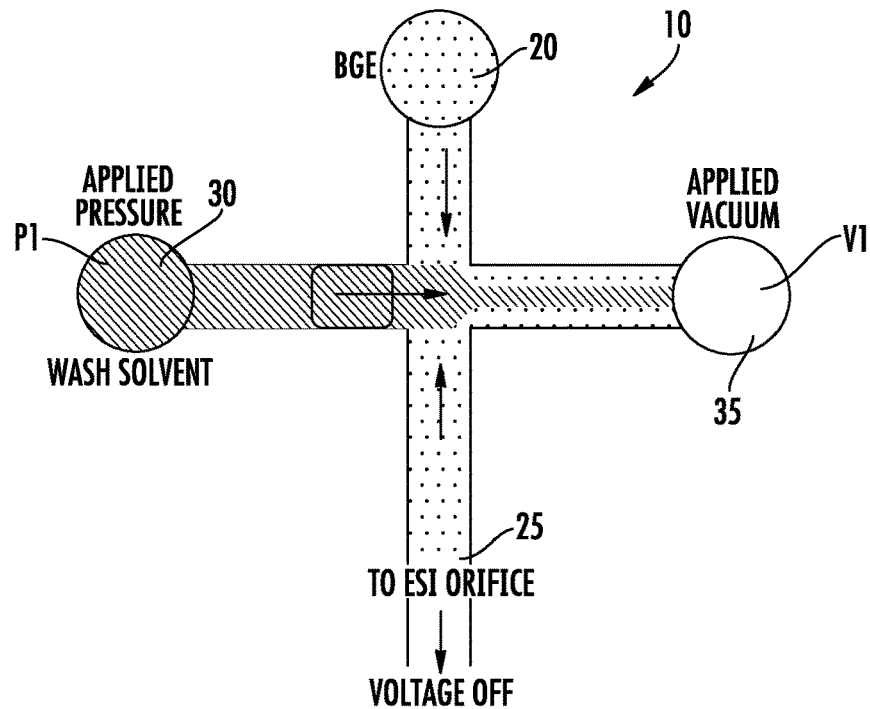
Figure 3B:
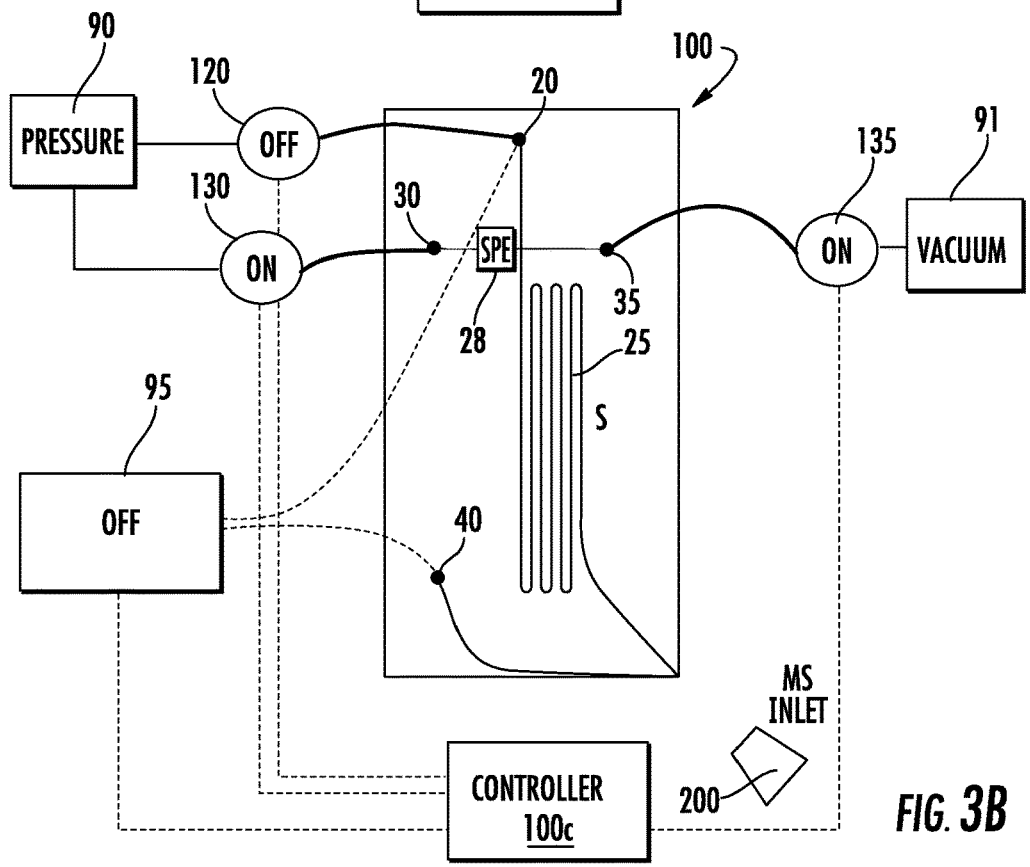
Figure 3C:
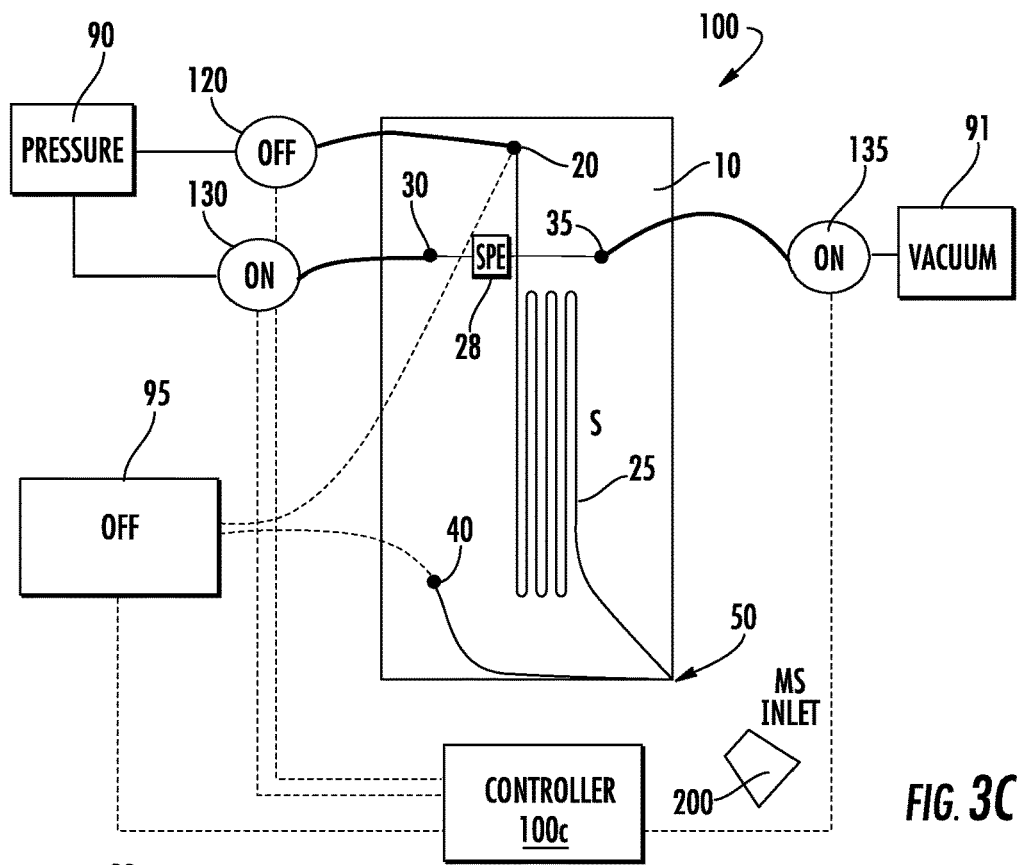

FIGS. 2D and 3B illustrate a sample loading step where sample S is introduced via reservoir 30 into the fluidic channel 31 with the SPE bed 28. While the device 10 shows the sample S introduced via the same reservoir 30 as the pre-conditioning material, a separate reservoir can be used (not shown). The sample loading can be carried out using only pressure inputs such as an applied pressure P1 and a reduced pressure such as a vacuum V1, with voltage OFF. FIG. 3I illustrates the valves 130 and 135 are ON while valve 120 is OFF (closed to supply line 70 into reservoir 20) and the voltage is OFF (i.e., not applied to inputs 20 or 40). FIGS. 2E and 3C illustrate an optional wash step where pressure P1 is applied to the reservoir 30 (or another reservoir in fluid communication with channel 31) and a lower pressure, typically a vacuum V1, is applied to the waste reservoir 35, with voltage OFF, to introduce a wash solvent to the fluidic channel 31 across the SPE bed 28 and into the waste reservoir 35. FIG. 3C illustrates the valves 130 and 135 are ON while valve 120 is OFF and the voltage is OFF (i.e., not applied to inputs 20 or 40).

The wash fluid, like the pre-conditioning material, can vary based on the chemistry of the SPE sorbent and the identity of the analyte(s). The purpose of the wash fluid is to displace the salt and any unbound species without unduly affecting the retention of the analyte(s) of interest. As an example, in reversed phase SPE, loading and binding occurs under low organic content conditions. Therefore, a low organic solution can be used to wash the sample S. In many cases, the wash solvent and the loading solvent can be the same. As with the pre-conditioning material/solvent, the washing fluid can change based on different mechanisms, HILIC, ion-exchange, and the like as is well known to those of skill in the art.

Figure 2F:
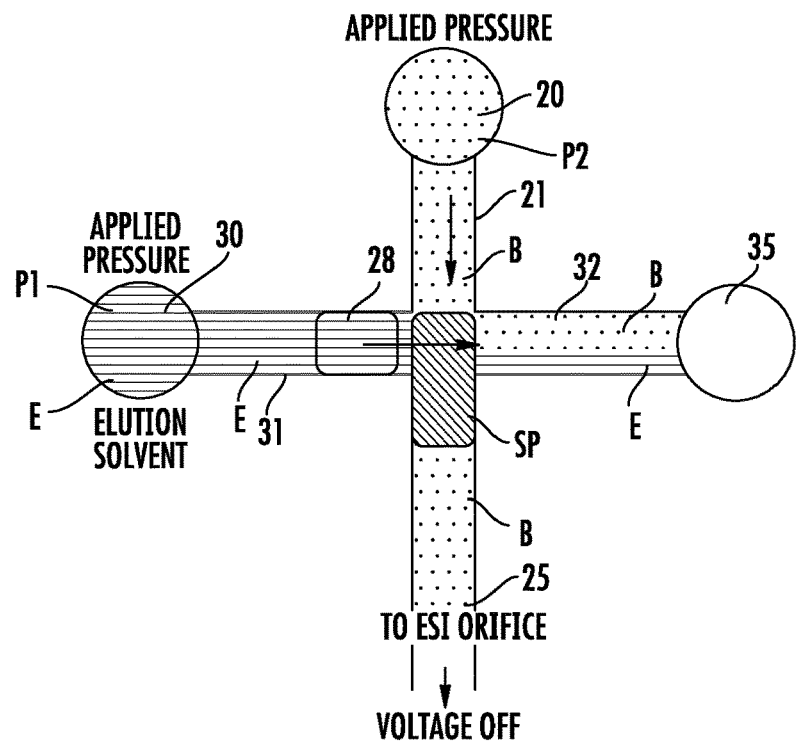
Figure 3D:
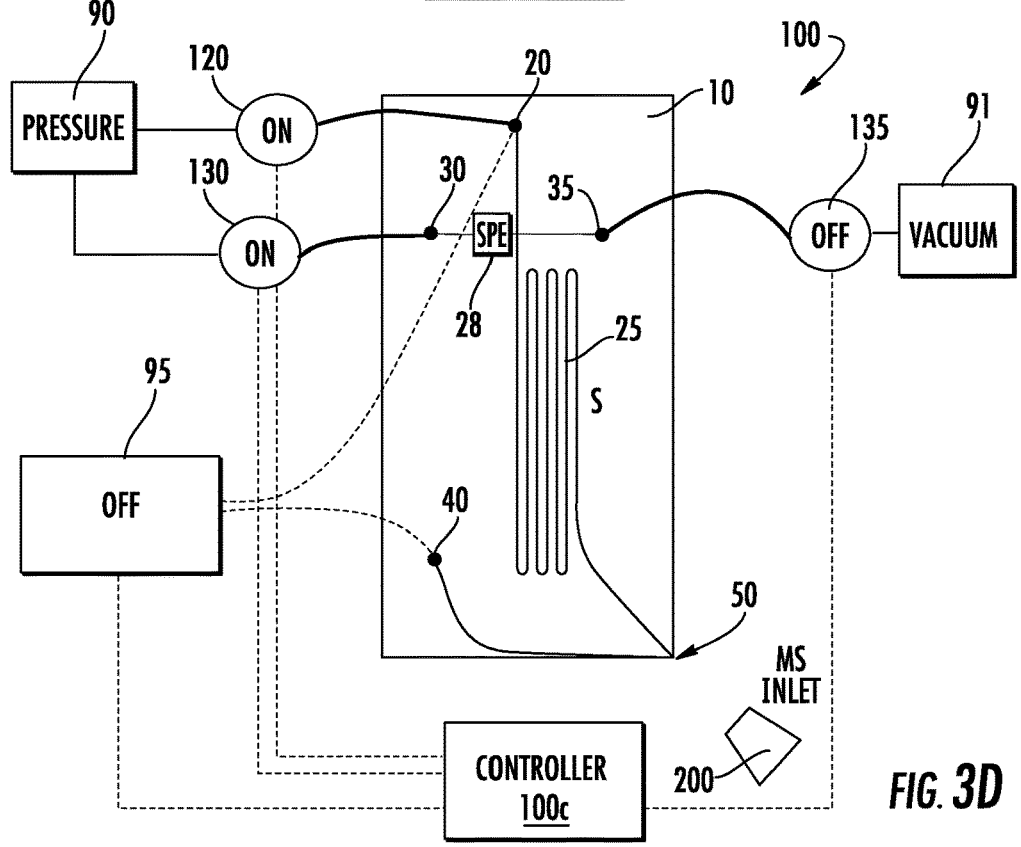

FIGS. 2F and 3D illustrate an elution operation that can be carried out after the washing and/or sample loading step to distribute a sample plug Sp into the separation channel 25. Pressure P1 is applied to the reservoir 30 with an elution fluid E while pressure P2 is also applied to the BGE reservoir 20 and no reduced pressure such as a vacuum is required to be applied to the waste reservoir 35 (i.e., no vacuum is applied but a positive pressure may be applied to help keep the sample plug Sp in the separation channel 25). FIG. 3D illustrates the valves 120 and 130 are ON while valve 135 is OFF and the voltage is OFF (i.e., not applied to inputs 20 or 40). The elution fluid E forces the sample plug Sp into the separation channel 25 and may flow into the waste channel 32 as indicated by FIG. 2F.

The elution material E can comprise high or low organic content. As used above, the term "low organic content" refers to an elution material in which organic analyte substances collectively comprise 25% or less of the volume of the elution material, and "high organic content" refers to an elution material in which organic analyte substances collectively comprise more than 25% by volume of the elution material.

The elution material E can comprise high or low salt content. As discussed above, with respect to certain processing conditions associated with SPE, low salt content refers to an elution material in which a concentration of dissolved salts is between 0-0.1 M, while high salt content refers to an elution material in which a concentration of dissolved salts is above 0.1 M, such as above 0.1 M to about 1 M.

The elution material E can have high or low pH. As used herein, low pH refers to acidic pH levels (below 7), and high pH refers to basic pH levels (above 7).

The elution material E can comprise a combination of salts, and organic analyte substances, and the organic content and salt content can each be high or low, independent of the other. Further, the elution material can have a high or low pH, independent of the salt and organic content.

In affinity chromatography/affinity SPE, the elution material may be an agent that disrupts the affinity binding, such as an analog of the sample with a higher binding affinity for the sorbent material. The elution and/or tITP material can be introduced via the BGE reservoir and channel 20/21 and/or via the sample channel 31 and a reservoir in fluid communication therewith.

Figure 2G:
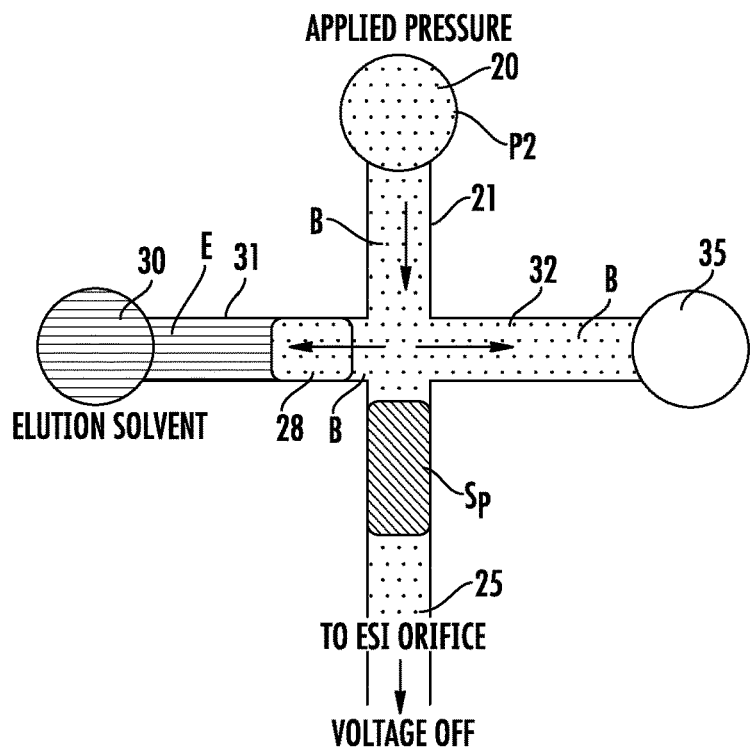
Figure 3E:
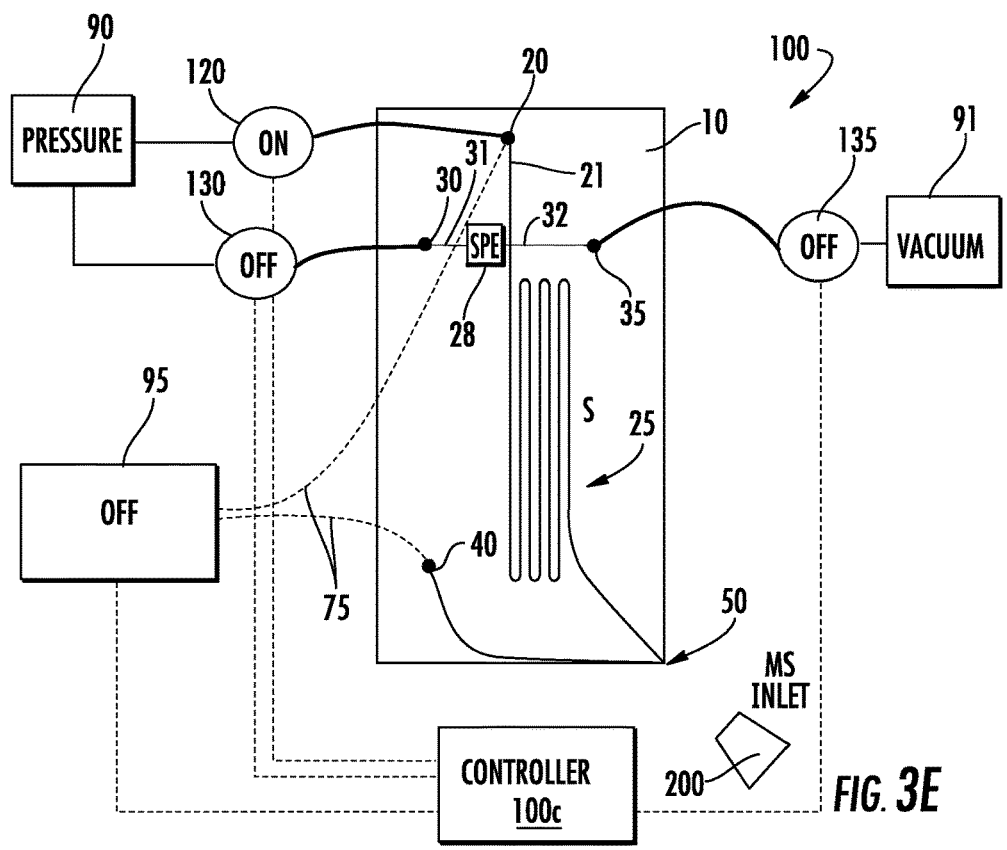

FIGS. 2G and 3E illustrate an optional clearing operation that can be used according to embodiments of the present invention. Pressure input P1 can be reduced or removed while pressure input P2 is applied to the BGE reservoir 20, with voltage OFF. Pressure input to the waste reservoir 35 can also be reduced or removed so that BGE fluid flows down to push the sample plug Sp past the fluidic channel 31 with the SPE bed 28. The BGE fluid can push the elution fluid E to exit the SPE bed 28 toward the reservoir 30. FIG. 3E illustrates the valve 120 is ON while valves 130 and 135 are OFF and the voltage is OFF (i.e., not applied to inputs 20 or 40).

Figure 2H:
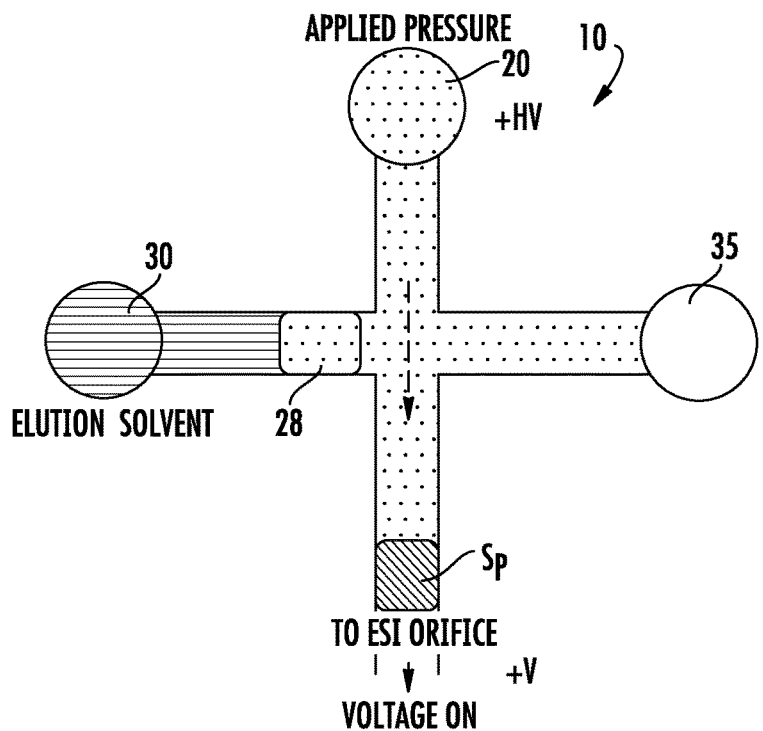
Figure 3F:
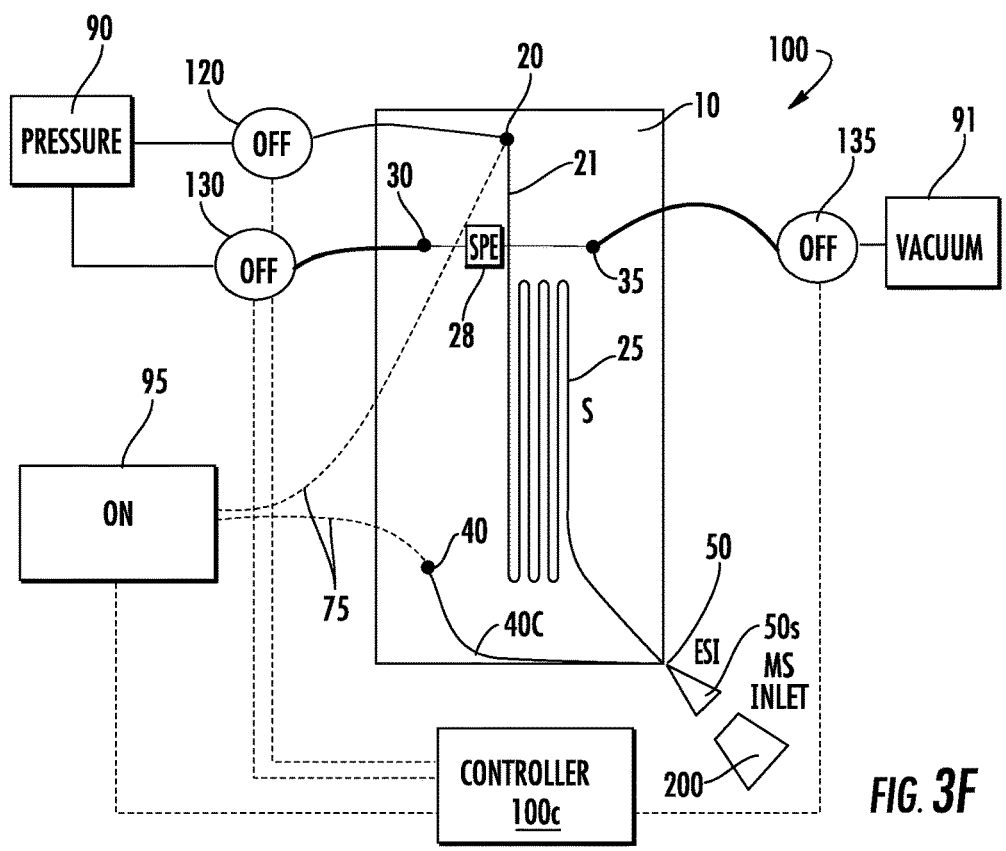

FIGS. 2H and 3F illustrate that a subsequent transport/separation between successive sample plugs Sp can be carried out by applying voltage to the BGE reservoir 20 and to the ESI orifice without applying pressure to reservoir 30 or 35. The applied voltage can be high voltage at reservoir 20 and a positive voltage at the ESI orifice (e.g., at EO pump input 40) to drive the sample plug Sp to the ESI emitter orifice 50. FIG. 3F illustrates the valves 120, 130 and 135 are OFF and the voltage is ON (i.e., applied to inputs 20 or 40). As discussed above, the term "high voltage" refers to voltage in the kV range, typically between about 1-100 kV, more typically between about 1-20 kV. ESI processes can employ potentials of a few kVs, typically between about 1 kV to about 5 kV, for example. Other voltages may be appropriate.

Generally stated, in some embodiments of the present invention, pressure (alone) can be used to inject samples of a microfluidic device 10 for microchip capillary electrophoresis (CE). The pressure-drive method has advantages over other microfluidic injection methods such as voltage-driven loading methods, in that it can use a simple channel geometry, but is capable of generating desired sample plug Sp sizes (FIGS. 2F, 2G, 2H) by simply adjusting the time the pressure is applied and/or the amount of pressure applied to the reservoirs 20, 30. The pressure-drive operation is also typically free of eletrokinetic injection bias and no voltage is required to be applied to the sample reservoir 30.

In some embodiments, the pressure applied concurrently to the BGE reservoir 20 and the sample reservoir 30 for the injection (FIGS. 2F, 3D) is between 1 and 30 psi for between 1-5 seconds, more typically between 1 and 12 psi. Then, for the clearing of the tail end of the sample (FIGS. 2G, 3E), the pressure P2 in the BGE reservoir 20 can be held the same or reduced by 10-80% and the pressure in the reservoir 30 can be reduced more than the reduction in the pressure of the BGE reservoir 20, e.g., typically so that it is less than 0.1 psi, e.g., zero or at ambient or atmospheric pressure or below ambient or atmospheric pressure (e.g., under vacuum). The term "reduced" with respect to pressure can also include removing the applied pressure altogether.

The clearing pressure on the BGE reservoir 20 (alone) can be held for a time that is less than the injection time where pressure is applied to both reservoirs 20, 30 (FIGS. 2F, 3D). The clearing time for the pressure applied only to the BGE reservoir 20 can be 2 seconds or less, 1 second or less or 0.5 seconds, for example.

However, while pressure-driven loading and injection may be particularly useful, embodiments of the invention can include electrokinetic (EK) gate methods using a sequence of different voltages applied to the microfluidic device 10 for sample loading and/or injection.

In some embodiments, pressure-driven methods can be particularly suitable for performing online sample concentration methods such as transient isotachophoresis (tITP), because sample plugs Sp with significantly different properties (electrical conductivity, pH, or viscosity) compared to the background electrolyte (BGE) can be injected. Salt or other electrolyte material in the sample/sample reservoir 30 can be used for tITP. The pressure-driven operation can position a well-defined band of sample (sample plug Sp) into the separation channel 25 of the microfluidic device using only pressure-driven flow and can also be used for online sample focusing methods that are not possible by other microfluidic injection methods.

Figure 7A:
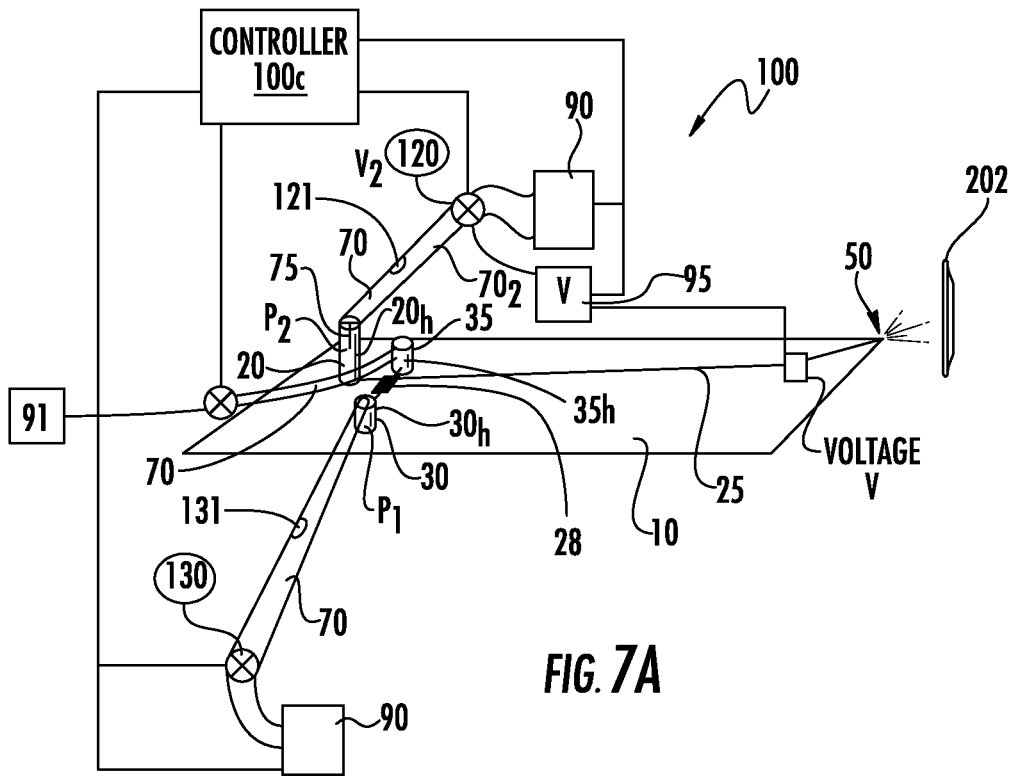
FIG. 7A is a schematic illustration of a microfluidic system according to embodiments of the present invention.

Referring to FIGS. 1 and 7A, head pressure can be applied to two different fluid reservoirs 20, 30 and/or 35 on or in communication with the microfluidic device 10, typically using off-device (e.g., off-chip) on/off valves 120, 130, 135. The term "head pressure" refers to the gas pressure in a sealed headspace of the reservoir above the liquid. The head pressure of the BGE reservoir 20 is labeled P2 and the head pressure of the sample reservoir 30 is labeled N. A controller 100c can be in communication with the valves 120, 130, 135 to independently control when the pressures P1, P2 and V1 are applied at the respective reservoirs 20, 30, 35. Thus, for sample loading no voltage is required to be applied to either the BGE reservoir 20 or the sample reservoir 30 (FIGS. 2D, 2F, 2G, for example).

The microfluidic channels 25, 31, 32 within the device 10 can, in some embodiments, be configured to form a simple injection cross.

Figure 4A:
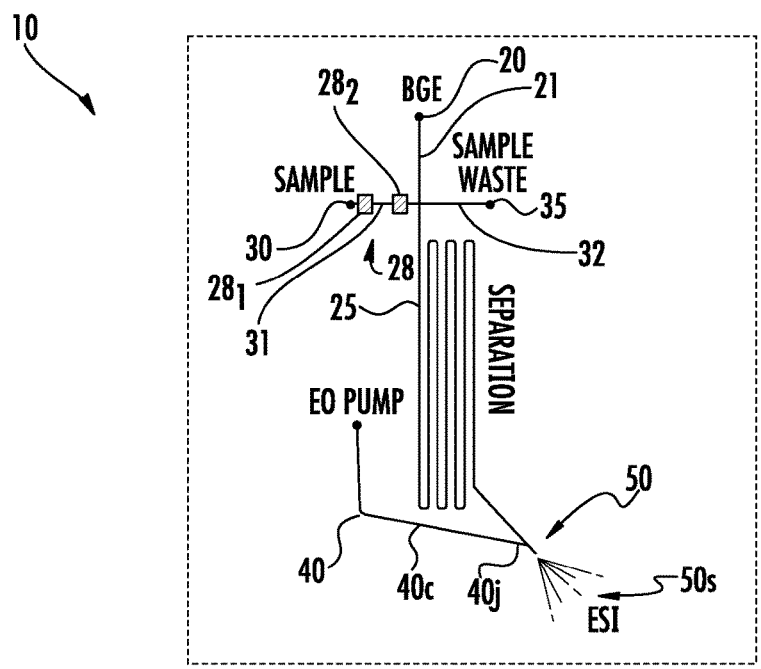
FIGS. 4A-4F are schematic illustrations of fluidic devices according to embodiments of the present invention.
Figures 4B, 4C, 4D:
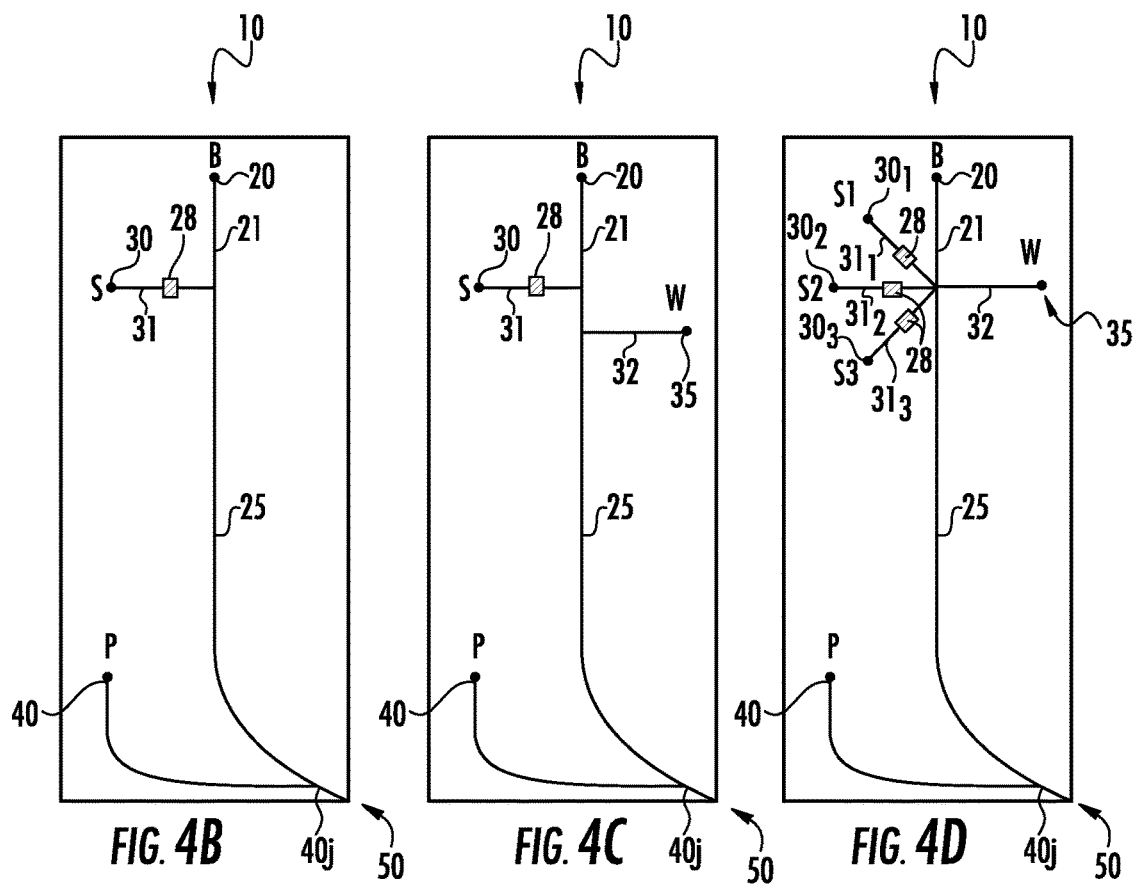

In some embodiments, the sample waste channel 32 may be excluded as shown in FIG. 4B, for example. Thus, the use of a "tee" intersection of the sample channel 31 (in lieu of the cross channel configuration) to the separation channel 25 may be used and may be implemented using a relatively precise pressure on the BGE reservoir 20 to hold that fluid stationary for injection/sample loading, at least where EK drive is not employed.

Referring to FIGS. 2F, 3D, pressure is concurrently applied to the sample reservoir 30 (P1) and the BGE reservoir 20 (P2) to drive sample S from the sample reservoir 30 (shown by the directional arrows) into the separation channel 25 from the sample channel 31, and typically the sample waste channel 32, but not the BGE channel 21. When a plug of a sample Sp in the separation channel 25 reaches a desired length (typically downstream of both the BGE reservoir 20 and the sample reservoir 30), as shown in FIGS. 2G, 3E, pressure is decreased or released from the sample reservoir 30, but pressure is kept on at the BGE reservoir 20. As shown by the arrows, flow from the BGE channel 21 clears sample in the sample and waste channels 31, 32, leaving a defined plug of sample Sp (trailing end is separated from any adjacent sample in the cross channels 31, 32) in the primary fluid transport (e.g., separation) channel 25. This pressure drive/injection is carried out without requiring any voltage input to the sample reservoir 30. At this point, as shown in FIGS. 2H, 3E, the pressure is released from the BGE reservoir 20 and voltage is applied between the BGE reservoir 20 and the separation channel 25 at a downstream location, typically an end portion or terminus of the separation channel 25 such as at EO input 40 to perform an electrophoretic separation.

The voltage applied to the BGE reservoir 20 can be a high voltage HV, although lower voltages may be used in some embodiments. The voltage V applied downstream can be a lower voltage than the voltage applied to the BGE reservoir 20. The lower voltage V can be any suitable EK driving voltage and may be between 10%-50% of the BGE reservoir voltage. Voltage can vary and typically ranges from about +1 kV to +30 kV and the lower voltage might range from 0 to +4 kV. But, the voltages and polarity can vary for different applications. For example, the polarity of the separation could be reversed so that the high voltage input shown in FIG. 2H is negative, or closer to zero (0) and the opposing voltage (shown in FIG. 2H as the "+V" input) could be higher or even negative depending on the relative length of the microfluidic channels, the charge of the analytes, and the polarity of the ESI process. Embodiments of the application refer to voltages that are referenced to a common ground or reference voltage with a value designated as "0" volts ("V").

In some embodiments, each of the sample reservoir 30, the BGE reservoir 20, and the waste reservoir 35 can be maintained at a common electrical potential as the sample is flowed through the sample channel using only pressure-driven operation so as to not apply an electrokinetic voltage, since these reservoirs are at the same electrical potential in the absence of an external field. The sample can be introduced into the separation channel 25 without applying an electrokinetic voltage and/or voltage gradient across the sample channel 31 and/or SPE bed 28.

The sample can be flowed through the sample channel 31 without applying a voltage to the sample reservoir 30, to the BGE reservoir 20, or to the waste reservoir 35 and/or with no electric potential gradient in any of the sample channel 31, the BGE channel 21 and the waste channel 32.

The pressures applied to the headspaces of the reservoirs 20, 30 can be low pressures, typically between 0.1 psi and 50 psi, more typically between 0.5 and 30 psi, or between about 0.5 and about 12 psi or 10 psi (0.69 bars). The pressures can be about 0.5 psi, about 1 psi, about 1.5 psi, about 2 psi, about 2.5 psi, about 3 psi, about 3.5 psi, about 4 psi, about 4.5 psi, about 5 psi, about 5.5 psi, about 6 psi, about 6.5 psi, about 7 psi, about 8 psi, about 8.5 psi, about 9 psi, about 9.5 psi, about 10 psi, about 10.5 psi, about 11 psi, about 11.5 psi, about 12 psi.

The reduced pressure such as a vacuum pressure applied to the waste reservoir 35 can be between about 1 psi and about 15 psi, typically between about 10 psi and 15 psi, such as 10 psi, 11 psi, 12 psi, 13 psi, 14 psi and 15 psi.

As noted above, tITP has been previously described as an online sample focusing method for capillary electrophoresis. This phenomenon works when the sample contains a relatively large concentration of an electrolyte (termed the leading electrolyte) that has higher electrophoretic mobility than the analyte ions. As is well known, the leading electrolyte is typically added to the sample solution. The leading electrolyte concentration should be significantly greater (such as at least 5× or 10× greater) than the electrolyte concentration in the background electrolyte to provide a sufficient minimum conductivity difference between the background electrolyte and the leading electrolyte. This is the situation that exists for the pressure-driven injection of samples with high concentration of sodium chloride or other defined electrolyte. For example, for a pH 2.2 background electrolyte with a hydronium concentration of approximately 6 mM, a 15 mM leading electrolyte is too low, but concentrations at or above 50 mM are sufficient for tITP to be observed.

To take advantage of the sample focusing effects of tITP one can inject a larger band of this sample relative to other sample processing/analysis methods and may use a suitable sample formulation with the large concentration of the electrolyte. Where used, the pressure-driven injection methods allow increased if not total or complete freedom in altering the size of the sample band, simply by changing the head pressure and/or the duration of the applied pressure for the sample loading step. The BGE reservoir 20 can include liquid electrolyte comprising sodium and/or salt in sufficient amount for tITP introduced through channel 21. The liquid electrolyte may optionally additionally or alternatively be introduced via another reservoir and channel, such as, via sample channel 31 or another side channel. This tITP can be carried out before the separation shown in FIGS. 2H, 3F to reduce band broadening that may otherwise be introduced during the transfer of the analyte sample from the SPE bed 28 to the separation channel 25.

FIGS. 4A-4F and 6A are non-limiting examples of microfluidic devices 10 that can be operated as described above. FIG. 4A illustrates the fluidic channel 31 can include a plurality of spatially separated SPE beds 28, shown as first and second SPE beds $28_1$, $28_2$. Where more than one SPE bed 28 is used they can comprise the same or different sorbents and have the same or different volumes and/or lengths.

FIG. 4B illustrates the microfluidic device 10 does not require a waste channel 32 or waste reservoir 35. FIG. 4C illustrates the waste channel 32 offset a longitudinal distance from the sample channel 31 across the separation channel 25. FIG. 4D illustrates the device 10 can have a plurality of sample reservoirs 30, shown by way of example as three, $30_1$, $30_2$, $30_3$, all or some of which can have the SPE bed 28, but more or less than three may be used. The reservoirs 30 can feed a common or different sample channels 31, shown as having different sample channels $31_1$, $31_2$, $31_3$ all for a single separation channel 25, and at least one BGE reservoir 20 (shown as a single BGE reservoir 20 and reservoir channel 21). The sample reservoirs 30 can be controlled to sequentially or serially be pressure-driven (or, in some embodiments, EK driven) to inject respective sample plugs across the SPE bed 28 and into the separation channel 25. The devices 10 can also optionally have an EO pump 40.

Figure 4E:
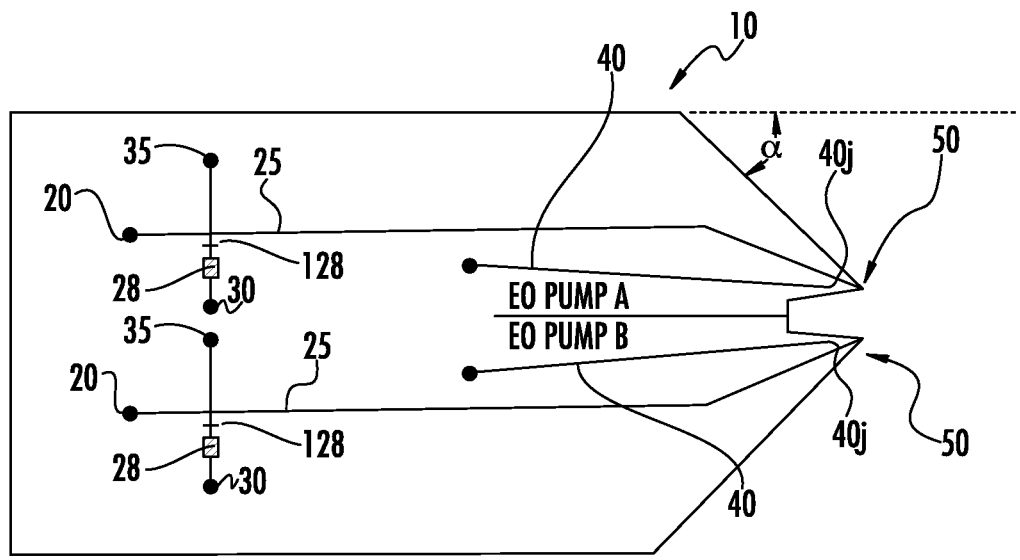

FIG. 4E illustrates a microfluidic device 10 that can have a plurality of separation channels 25, shown as two adjacent channels, but more than two may be included on a single device 10. The separation channels 25 can feed a common or separate emitters 50. Thus, the microfluidic device 10 can include more than one separation channel 25 and associated BGE reservoir 20, reservoir 30, SPE bed 28, waste reservoir 35 and channels 31, 32. One or more of the individual channels 21, 25, 31, 32 might be configured to have lateral dimensions of about 1-100 µm, e.g., about 75 µm, with lateral spaced apart dimensions of about 1-100 mm, in some particular embodiments.

Figure 4F:
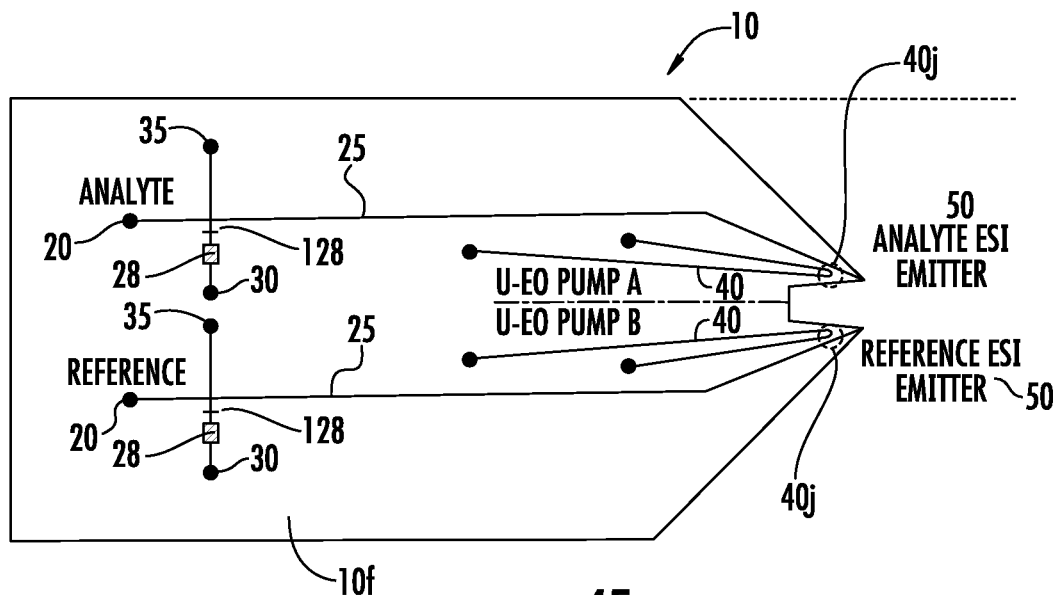

As shown in FIG. 4F, one or more reference channels for a reference spray may be included on/in the microfluidic device 10. Where used, the reference material for the reference spray from a respective ESI emitter 50 can provide one or more ions for internal calibration. In some embodiments, the reference material provides a single defined ion for internal calibration. In other embodiments, the reference material can include multiple ions over a desired range, typically that are over substantially an entire m/z range of interest, to improve the mass accuracy.

Figure 5A:
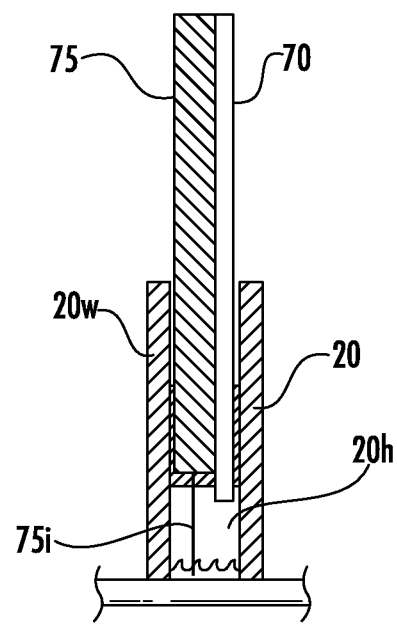
FIG. 5A is a schematic illustration of an example of a gas-tight connection with a pressurized supply line for the background electrolyte (BGE) reservoir according to embodiments of the present invention.

FIG. 5A is a schematic illustration of a BGE reservoir 20 having a gas-tight fitting holding a pressure supply line 70 and a (typically high) voltage line 75 with a high voltage input 75$i$ (shown as a platinum wire) that extends inside the sealed reservoir 20 so as to be able to make contact with the fluid, e.g., liquid, in the reservoir 20. The term "gas-tight" means that the seal on the reservoir 20, 30 does not unduly leak when operated so as to be able to provide the desired pressure to the headspace 20$h$, 30$h$, 35$h$ for pressure-driven injection.

Figure 5B:
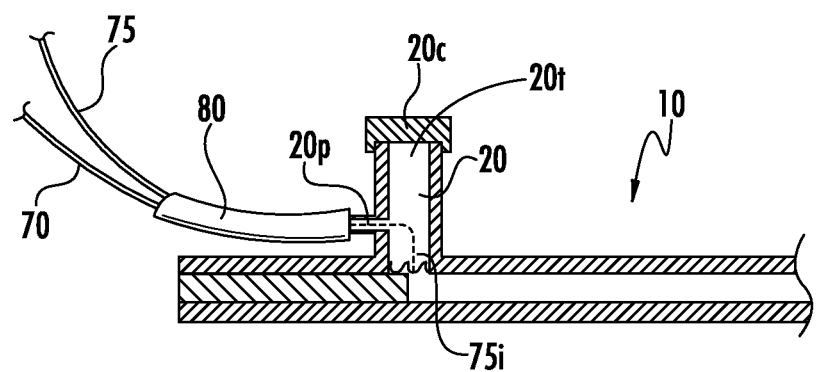
FIG. 5B is a schematic illustration of another example of a gas-tight connection with a pressurized supply line for the background electrolyte (BGE) reservoir according to embodiments of the present invention.

The pressure supply line 70 can be provided with tubing with an open pressurized gas path extending into the sealed headspace 20$h$. For an example of an 8 mm inner diameter reservoir wall 20$w$, the pressure supply line can be tubing less than this size, e.g., ¼ inch to about ¹⁄₁₆ inch outer diameter. However, larger size conduits can be used when stepped down in size for the supply into the reservoir head space under the sealed connection. The sealed (e.g., gastight) connection of a respective pressurized gas supply line 70 to either reservoir 20, 30 (and/or waste reservoir 35) can be provided via epoxy, O-ring, metal or elastomeric gaskets, grease fittings, and/or other suitable configurations. FIG. 5B illustrates that the pressured gas supply line 70 can be held adjacent the high voltage cable 75 in a common sleeve 80. It is further noted that the high voltage cable 75 can be held routed into the headspace while held inside the gas supply tubing.

FIG. 5B also illustrates that the top of the reservoir 20$t$ can be sealed with a cap 20$c$ and a side port 20$p$ can be used to attach the pressurized gas supply line 70 to the reservoir 20. The same arrangement can be used for the sample reservoir 30 and/or waste reservoir 35 (not shown). In some embodiments, the gas supply line 70 can be attached over the outer wall of the wall 20$w$ of the reservoir 20 instead of extending inside the reservoir 20 for gas-tight or sealed connection. Other connection configurations may be used.

Figure 7B:
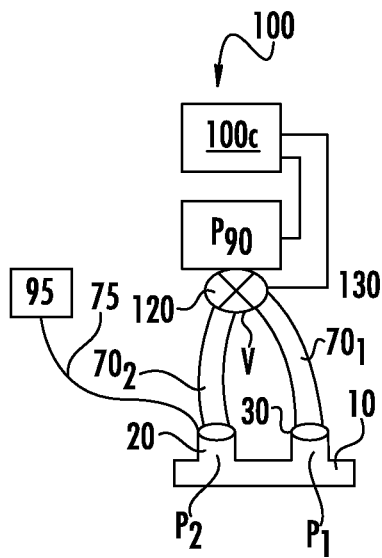
FIG. 7B is a schematic illustration of another embodiment of a microfluidic system according to embodiments of the present invention.

FIG. 7A illustrates an example of a microfluidic system 100 which includes a controller 100$c$ used to control operation of the pressure supply to the reservoirs 20, 30 to carry out a pressure-driven injection. The system 100 can include first and second pressurized gas supply lines or conduits 70, shown as $70_1$, $70_2$, each in fluid communication with at least one valve 120, 130. The system 100 can include a three-way valve (FIG. 7B) that closes and opens each supply line of the valves 120, 130. However, in preferred embodiments, separate valves 120, 130, 135 are used for each supply line $70_1$, $70_2$ (and $70_3$). One or all of the valves 120, 130, 135 can be a three-way valve (e.g., three way operation, open/close to source, open/close to head space and open/close to atmosphere) for a respective supply line 70 which can allow for the rapid venting of pressurized gas from a respective supply line. Thus, in operation, one or both of the valves 120, 130, 135 can be operated to vent the head pressure in the reservoir 20, 30, to atmosphere, which may help precisely control the injection process. One or both of the gas supply lines 70 and/or reservoirs 20, 30, 35 can also or alternatively include vents 121, 131 (FIG. 7A) that can be electronically opened and closed, for rapid venting to atmosphere to decrease pressure in a respective headspace 20$h$, 30$h$. The term "rapid" with respect to the venting or pressure reduction (e.g., venting to atmosphere) in a respective pressure supply line 70 refers to a drop in pressure of the corresponding headspace 20$h$, 30$h$, 35$h$ of a respective reservoir 20, 30 and 35 to at least atmospheric pressure within 0.1-3 seconds, more typically within about 2 seconds or within about 1 second. The rapid venting can be based on a control signal from the controller 100$c$ that (a) directs the valve 120 or 130 or 135 to open to atmosphere (where a three-way valve is used) or (b) opens a vent separate from the valve 120, 130, 135 and closes the valve 120, 130, 135. The rapid pressure reduction (e.g., venting) can be measured by a pressure sensor in the supply line or reservoir to indicate the rapid drop in head pressure from an operative pressure to atmospheric pressure within a 0.1-2 second time period. In some embodiments, the rapid venting can be carried out in between about 0.1 seconds and 1.5 seconds, such as about 0.1 seconds, about 0.2 seconds, about 0.3 seconds, about 0.4 seconds, about 0.5 seconds, about 0.6 seconds, about 0.7 seconds, about 0.8 seconds, about 0.9 seconds, about 1 second, about 1.1 seconds, about 1.2 seconds, about 1.25 seconds, about 1.5 seconds, about 2 seconds, and about 2.5 seconds.

The first and second pressurized gas supply lines $70_1$, $70_2$ can each be in communication with a common pressurized gas source 90 or each may have its own pressurized gas source. The system 100 can include a power supply 95 for the high voltage input to the microfluidic device 10. The power supply 95 can be attached to the cable 75.

The controller 100c can direct the timing sequence of the differentially applied pressure to the microfluidic device. The controller 100c can be in communication with the valves 120, 130, 135 the at least one pressure source 90 (and a pressure reducing device 91, where used) and the power supply 95. The term "controller" is used broadly to include a single or multiple processors or application specific integrated circuit (ASIC) held on or in communication with a single device, e.g., the microfluidic device 10, and/or computer, laptop, notebook, smartphone and the like, or distributed in different devices using wires or wireless connections including local area networks or wide area networks, e.g., the internet, including any server system.

Figure 8:
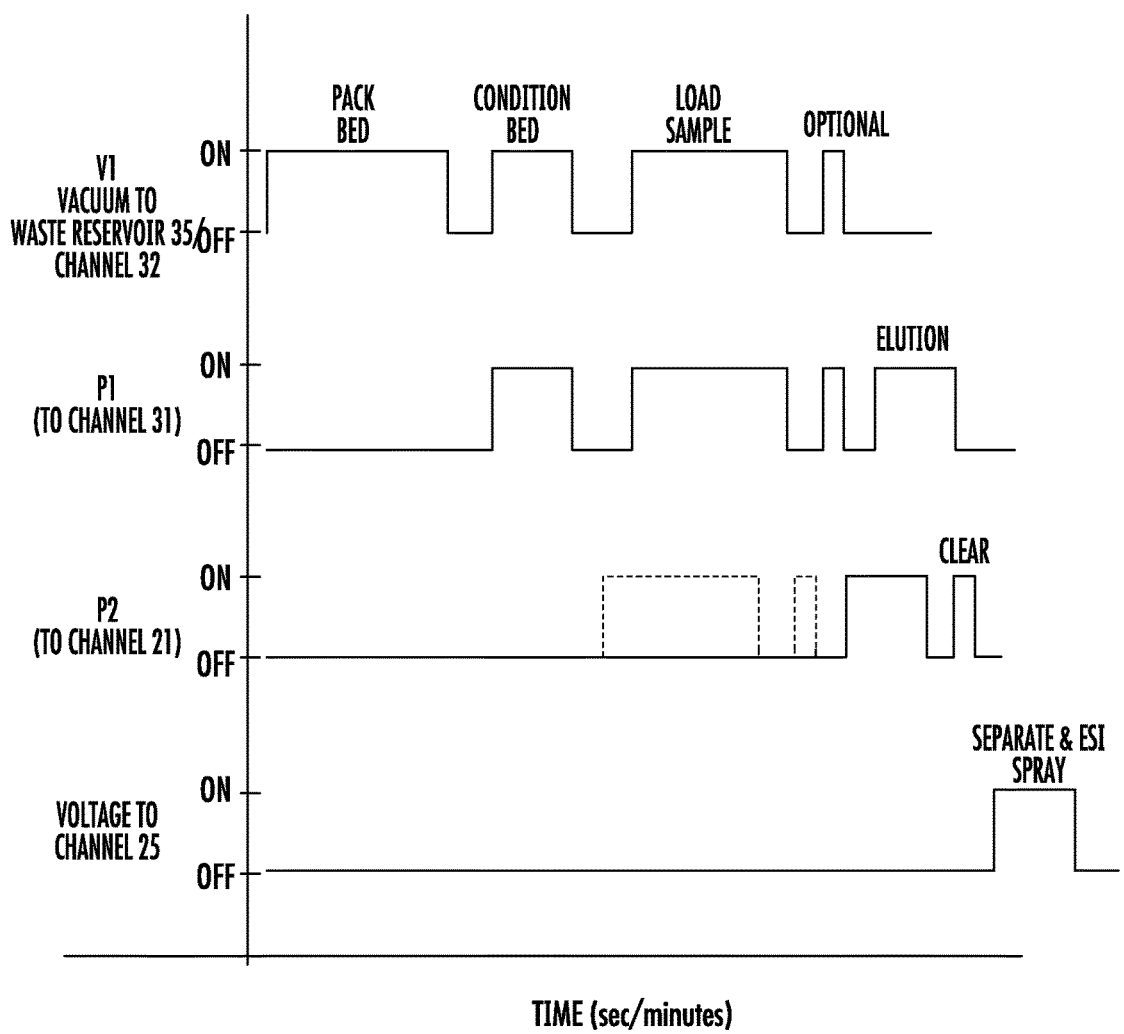
FIG. 8 is an example of a timing chart for the pressures applied to the sample reservoir, the waste reservoir and the BGE reservoir for loading/injecting a sample into a separation channel according to embodiments of the present invention.

The controller 100c can direct the valves 120, 130, 135 to open and close to carry out successive sample injections using a defined sequence, an example of which is shown in the timing chart of FIG. 8. In the example shown, the SPE can be packed before the sample is loaded. The packing can be carried out using a reduced pressure (relative to pressure applied to the other reservoirs) such as a vacuum V1 applied to the waste reservoir 35 with or without pressure applied to either the sample channel 31 or BGE channel 21, typically without such other pressures. The packing of the SPE bed can be carried out using a defined pressure for a defined time, typically between 1-10 minutes. Pressures P1, V1 can be applied for a defined time that is typically less than the packing duration. The sample can be loaded using the pressures P1, V1, typically for a duration that less than the packing time, such as between 30-50% of the packing time and/or between 1-8 minutes. Pressure P2 can then be applied concurrent with pressure P1 to inject the sample plug into the separation channel 25. Then, the electric field can be applied to separate the sample plug and spray the sample toward an inlet of an MS. The broken line shown for P2 illustrates that this pressure can be ON (typically at the same or a lesser amount as for the separation pressure).

The SPE bed can be pre-conditioned for a short time, typically between about 10 seconds to about 1 minute before the loading of the sample using V1 and P1 as shown. The elution can include applying a short duration (i.e., 0.1-1 second) of pressures V1, P1 followed by a longer duration of pressures P1 and P2 for the injection/sample plug delivery to the separation channel V1 may be OFF or ON during the elution delivery.

It is noted that the electrophoretic separation voltage can be applied concurrently with or just after pressure P2 is removed or decreased from the BGE reservoir 20. As shown, sample injection is carried out using only pressure P2 applied to the BGE reservoir and only pressure P1 applied to the sample reservoir from the first and second supply lines 70 (e.g., tubes or conduits) without any electrokinetic (EK) voltage. Voltage can be applied to the BGE reservoir 20 after the injection for the ESI emitter spray 50s.

The controller 100c can be configured to operate the fluidic device 10 using a defined timing sequence for applying defined pressures (headspace pressures) between 0.1 and 30 psi to a headspace 20h of the BGE reservoir 20 via the supply tube $70_2$ and to a headspace 30h of the sample reservoir 30 via the supply tube $70_1$ for defined durations, typically between 1 and 10 seconds, to inject a sample into the separation channel 25. The timing chart shown in FIG. 8 is by way of example and the noted "zero" pressures of P1 (for the sample reservoir 30) and P2 (for the BGE reservoir 20) may be atmospheric or ambient pressures or may alternatively be vacuum pressures. The applied voltage V from the power supply 95 to the input 75i in the BGE reservoir 20 (bottom line of the timing chart in FIG. 8) can have a shorter or longer duration than the concurrent injection pressures P1, P2 (FIG. 2F) or the subsequent "clearing" pressure P2 (FIG. 2G). The P2 pressure can remain constant or change, typically decreasing, from the concurrent pressure for injection to the "clearing" pressure when P1 is "OFF" or substantially decreased (FIG. 2G).

The fluidic device 10 can be a microfluidic chip that has a substrate 10s and/or ceiling 10c that is formed of hard or substantially rigid materials that include, but are not limited to, substrates comprising one or combinations of: glass, quartz, silicon, ceramic, silicon nitride, polycarbonate, and polymethylmethacrylate. In particular embodiments, the device 10 can include a glass substrate such as a borosilicate. In other embodiments, a rigid polymer material may be used to form the microfluidic device. The device 10 can also include one or more layers of a soft or flexible substrate. Soft substrate materials, where used, can have a low Young's Modulus value. For example, elastomers and harder plastics and/or polymers can have a range between about 0.1-3000 MPa. Examples of soft materials include, but are not limited to, polydimethylsiloxane (PDMS), polymethylmethacrylate (PMMA), and polyurethane. See, e.g., co-pending PCT/US2012/027662 filed Mar. 5, 2012 and PCT/US2011/052127 filed Sep. 19, 2011 for a description of examples of microfabricated fluidic devices. See, also, Mellors, J. S.; Gorbounov, V.; Ramsey, R. S.; Ramsey, J. M., Fully integrated glass microfluidic device for performing high-efficiency capillary electrophoresis and electrospray ionization mass spectrometry. Anal Chem 2008, 80 (18), 6881-6887. Additional aspects of such devices are disclosed, for example, in Xue Q, Foret F, Dunayevskiy Y M, Zavracky P M, McGruer N E & Karger B L (1997), Multichannel Microchip Electrospray Mass Spectrometry. Anal Chem 69, 426-430, Ramsey R S & Ramsey J M (1997), Generating Electrospray from Microchip Devices Using Electroosmotic Pumping. Anal Chem 69, 1174-1178, Chambers A G, Mellors J S, Henley W H & Ramsey J M (2011), Monolithic Integration of Two-Dimensional Liquid Chromatography—Capillary Electrophoresis and Electrospray Ionization on a Microfluidic Device. Analytical Chemistry 83, 842-849. The contents of these documents are hereby incorporated by reference as if recited in full herein.

EO pumps can be integrated on a microfluidic device 10 for electrospray ionization via implementations other than the examples shown in FIGS. 4A-4F. In general, two channels intersect at a junction, which may be a T-like junction (not restricted to a right angle intersection). A voltage is applied to two of the three resulting channel termini generating an axial electric field through the associated channel segments. To realize hydraulic transport through the third channel segment, the electroosmotic mobility in the two channel segments that contain the axial electric field is generally different in magnitude and/or sign. The difference in electroosmotic mobility can be achieved by chemically modifying one, or both, of the associated channel segments so as to produce different surface charge densities and hence different electroosmotic mobilities. Electroosmotic mobility can also be modified by coating a channel wall with electrically neutral polymer films, thereby increasing the effective fluid viscosity within the electrical double layer at the wall. Another way to modify electroosmotic mobility is reduce one of the channel lateral dimensions to distances similar in magnitude to the Debye length of the solution being electroosmotically pumped. The described methods for modifying electroosmotic mobility may also be used in combination where desired. Methods for electroosmotic pumping are further described in U.S. Pat. No. 6,110,343, the contents of which are hereby incorporated by reference.

While it is convenient to monolithically integrate EO pump functional elements on electrospray microfluidic devices, it is possible to hydraulically deliver sample materials to the emitter. See, e.g., Chambers A G, Mellors J S, Henley W H & Ramsey J M (2011) Monolithic Integration of Two-Dimensional Liquid Chromatography—Capillary Electrophoresis and Electrospray Ionization on a Microfluidic Device. *Analytical Chemistry* 83, 842-849. When utilizing hydraulic transport to supply analyte to the emitter, electrical connection for producing the electrospray, voltage can be achieved using a side channel similar to the EO pumping channel or by contacting the fluid using an electrode in a reservoir external to the microfluidic device, or in the case of using metal tubing between the device 10 and the pump, connection can be made to the tubing.

Figure 9A:
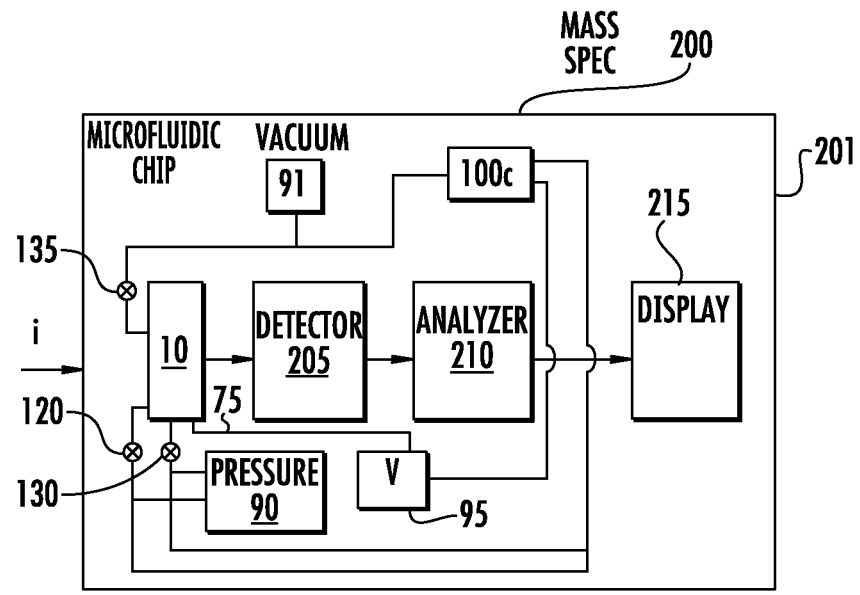
FIG. 9A is a schematic illustration of a portable MS device with an onboard microfluidic system that has pressure-driven injection according to embodiments of the present invention.
Figure 9B:
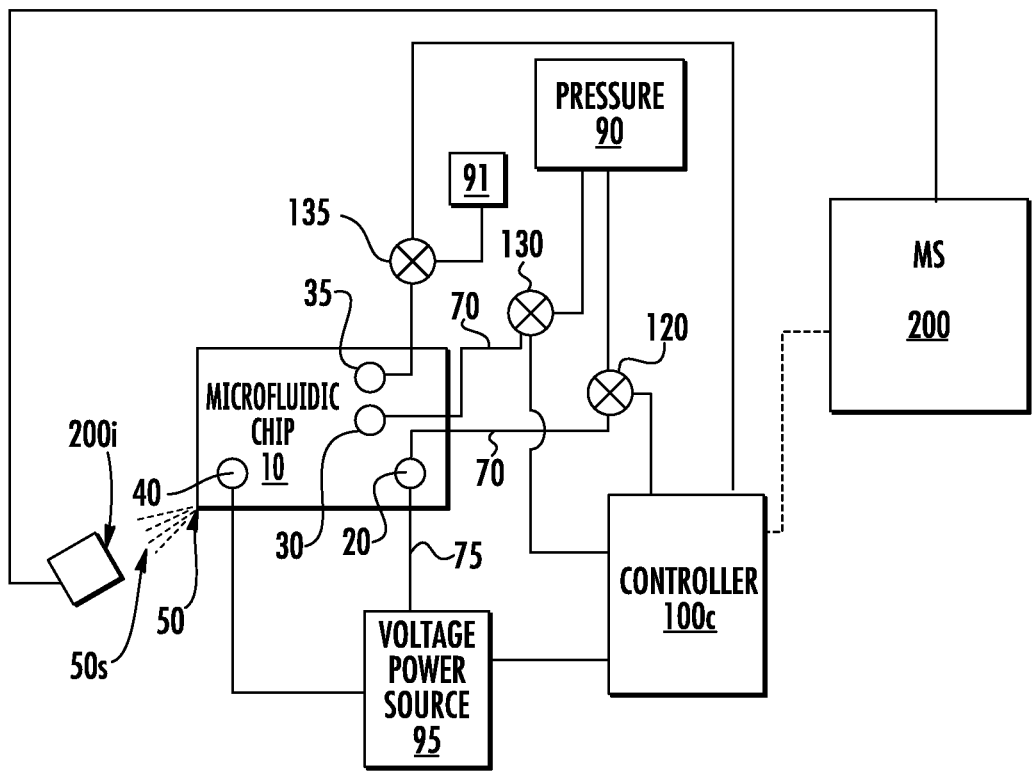
FIG. 9B is a schematic illustration of an external MS in communication with a microfluidic device according to embodiments of the present invention.

FIGS. 9A and 9B schematically illustrate embodiments of the invention. FIG. 9A illustrates a portable mass spectrometer 200 with a housing 201 holding at least one of the microfluidic devices 10 with an onboard controller 100c, a power supply for the voltage 95, a pressurized gas supply 90, a pressure reducing device 91, a detector 205, an analyzer 210 and an optional display 215 for providing output data.

FIG. 9B illustrates that the microfluidic device 10 can be in communication with a mass spectrometer 200 with an MS input 200i facing the ESI emitter 50 for receiving the spray 50s. The controller 100c can be separate or partially or totally onboard the mass spectrometer 200.

Figure 10A:
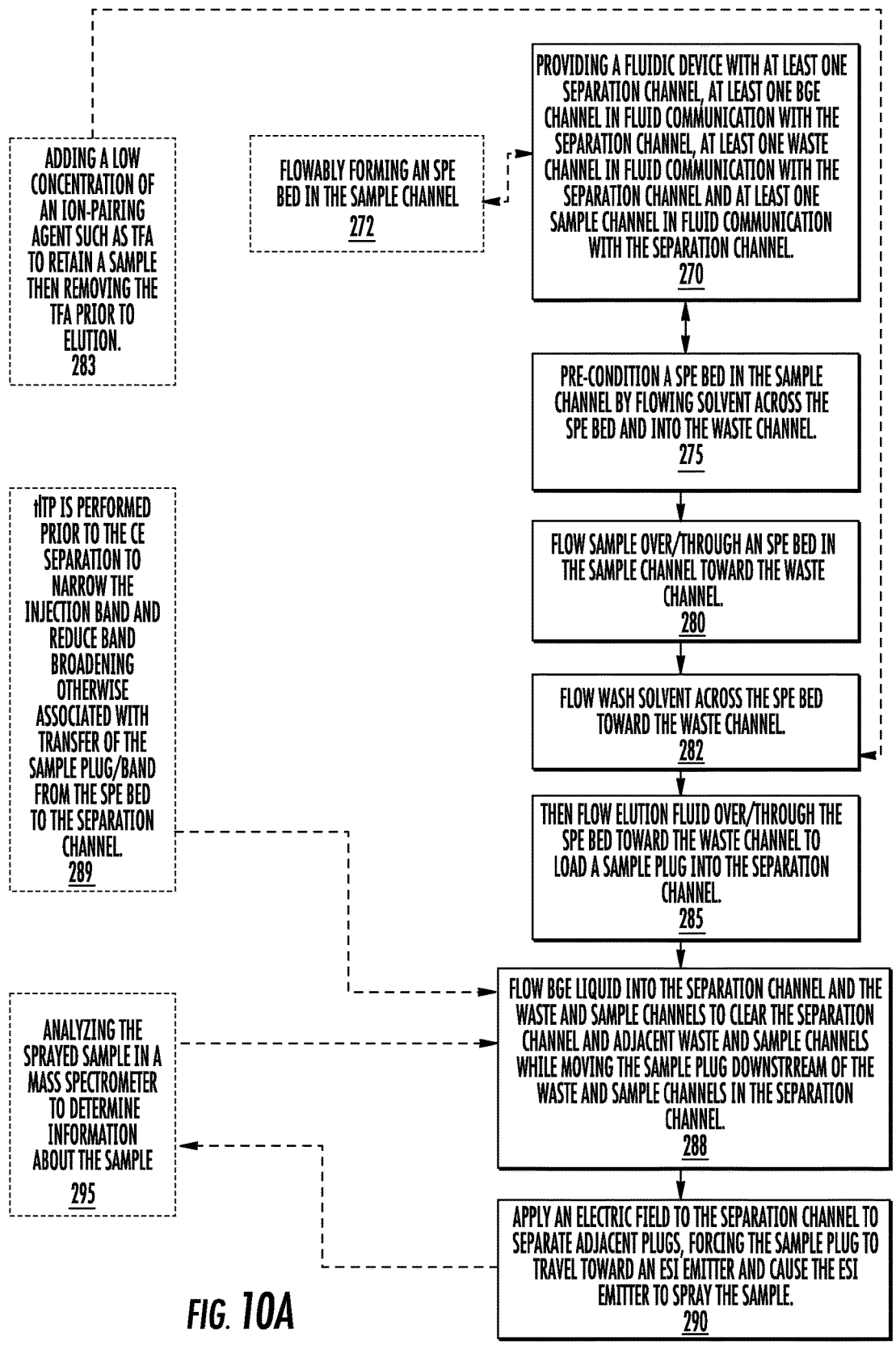
FIGS. 10A and 10B are flow charts of exemplary operations that can be used to carry out embodiments of the present invention.

FIG. 10A is a flow chart of exemplary operations that can be used to carry out a sample analysis. A fluidic device is provided (block 270). The fluidic device has at least one separation channel, at least one BGE channel in fluid communication with the separation channel, at least one waste channel in fluid communication with the separation channel and at least one sample channel in fluid communication with the separation channel.

The sample channel can have a pre-formed SPE bed therein.

The SPE bed can be flowably formed in the sample channel (block 272).

The SPE bed can be flowably formed by applying a reduced pressure via a pressure reducing device to the waste channel while applying a greater pressure to the sample channel to flow a slurry of SPE material into the sample channel until it hits at least one blocking member residing upstream of the separation channel to flowably form the SPE bed.

The SPE bed can be pre-conditioned by flowing solvent across the SPE bed and into the waste channel (block 275).

A low concentration of an ion-pairing agent such as TFA to retain a sample can be introduced before introducing the sample per block 280 and then the TFA can be removed prior to elution of block 285 (block 283).

The sample can be flowed over/through at least one SPE bed in the sample channel toward the waste channel (block 280).

Wash solvent can be flowed across the at least one SPE bed toward the waste channel after the same is flowed over the SPE bed (block 282).

Elution fluid can then be flowed over/through the at least one SPE bed toward the waste channel to load a sample plug into the separation channel (block 285).

BGE liquid can then be flowed into the separation channel a distance below/downstream of the waste and sample channels to clear the separation channel and adjacent waste and sample channels while moving the sample plug downstream of the waste and sample channels in the separation channel (block 288).

tITP can be performed (using the BGE reservoir) prior to the CE separation of block 288 to narrow the injection band and reduce band broadening otherwise associated with transfer of the sample plug/band from the SPE bed to the separation channel (block 289).

An electric field can be applied to the separation channel to separate adjacent plugs, forcing the sample plug to travel toward an ESI emitter and cause the ESI emitter to spray the sample (block 290).

The sprayed sample can be analyzed in a mass spectrometer to determine information about the sample (block 295). The analysis can include detecting analyte peak signals of the sample using a mass spectrometer and generating electropherograms of the sample, for example.

Electronic detection of signal of the separated sample in the separation channel can be obtained using a detector in communication with the separation channel (optically and/or electronically). This electronic detection can be carried out without the mass spectrometer detection or with the mass spectrometer detection. In some embodiments, the electronic detection by the detector is carried out simultaneously with detection by the mass spectrometer for a respective separated sample.

The pre-conditioning, flowing and loading steps can be carried out using only a sequence of defined pressure inputs to the BGE channel, the sample channel and the waste channel without requiring electric fields until the separation and spray.

Figure 10B:
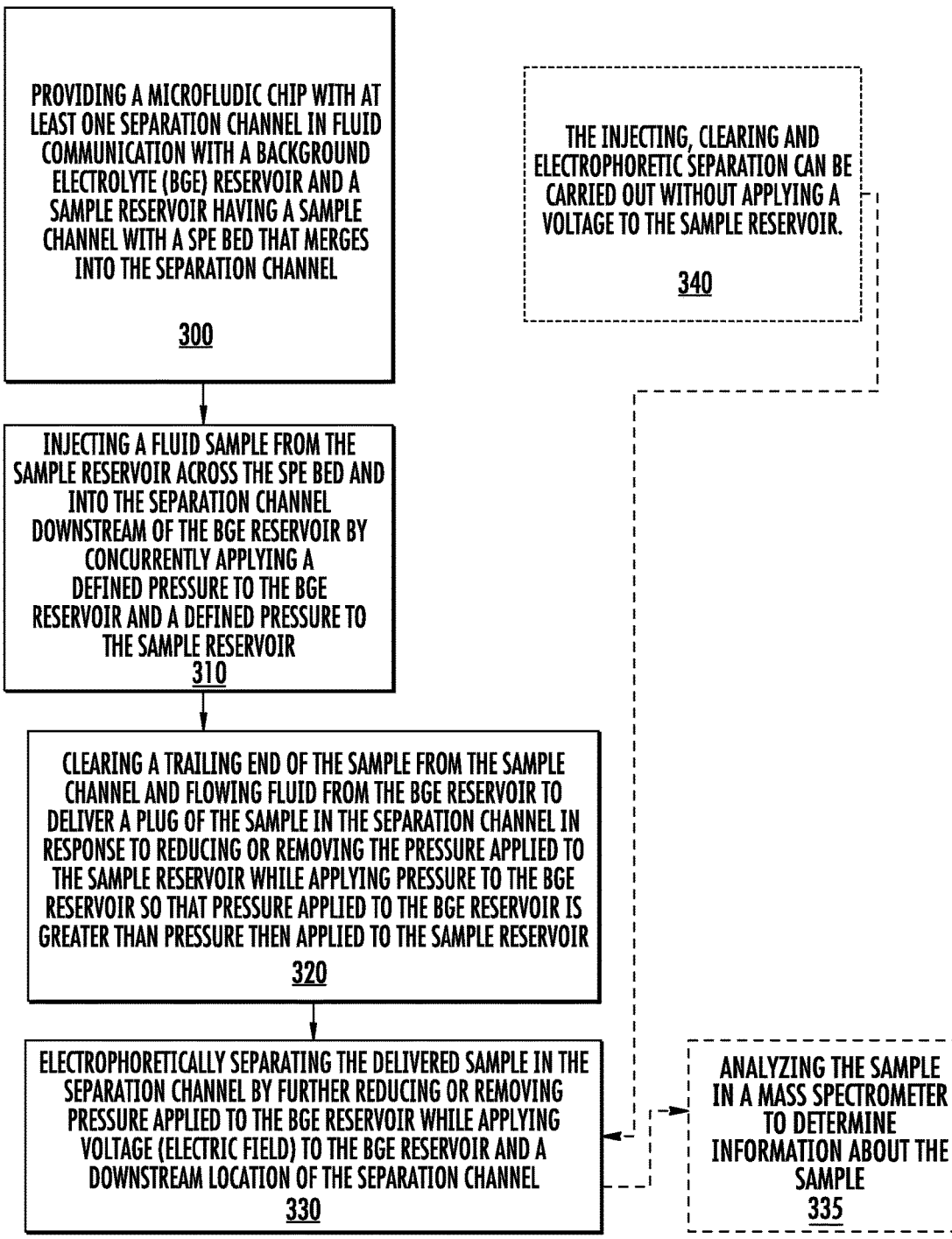

FIG. 10B is a flow chart of exemplary operations that can be used to carry out a sample analysis. A microfluidic device is provided with at least one separation channel in fluid communication with a background electrolyte (BGE) reservoir and a sample reservoir and having a sample channel with an SPE bed; the sample channel merges into the separation channel (block 300). A fluid sample is injected (flowably introduced) from the sample reservoir across the SPE bed into the separation channel downstream of the BGE reservoir by concurrently applying a defined pressure to the BGE reservoir and a defined pressure to the sample reservoir (block 310).

A reduced pressure (optionally a vacuum) can be applied to a waste reservoir residing across from the sample channel during the injecting step.

After the injection/introduction, a trailing end of the sample plug is cleared from the sample channel using fluid flowed from the BGE reservoir to deliver the sample plug in the separation channel in response to reducing or removing the pressure applied to the sample reservoir while applying pressure to the BGE reservoir so that pressure applied to the BGE reservoir is greater than pressure then applied to the sample reservoir (block 320). Then, the delivered sample is electrophoretically separated in the separation channel by applying an electric field to the separation channel, i.e., voltage to the BGE reservoir and a downstream location of the separation channel or proximate EO pump channel/input (block 330). The pressure in the BGE reservoir can be held constant, further reduced or removed while the voltage is applied.

The injecting, clearing and electrophoretic separation can be carried out without applying a voltage to the sample reservoir (block 340).

A duration of the pressure can be electronically adjusted or the pressure applied to the sample or BGE reservoir 20, 30 can be increased or decreased for the injecting and/or clearing to adjust a size of the plug of the sample delivered to the separation channel.

As the analyte bands elute from the distal end of the electrophoretic separation channel, the separated sample can be analyzed, optionally using a mass spectrometer to determine information about the sample (block 335). The analysis can include detecting analyte peak signals of the sample using a mass spectrometer and generating electropherograms of the sample, for example. The analysis can comprise electrical conductance detection and/or optical detection of the separated sample in the separation channel to obtain quantitative and/or qualitative data of the analytes in the sample.

It is noted that embodiments of the present invention may combine software, firmware and/or hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Embodiments of the present invention are described herein, in part, with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, or a block divided and performed separately, depending upon the functionality involved.

Figure 11:
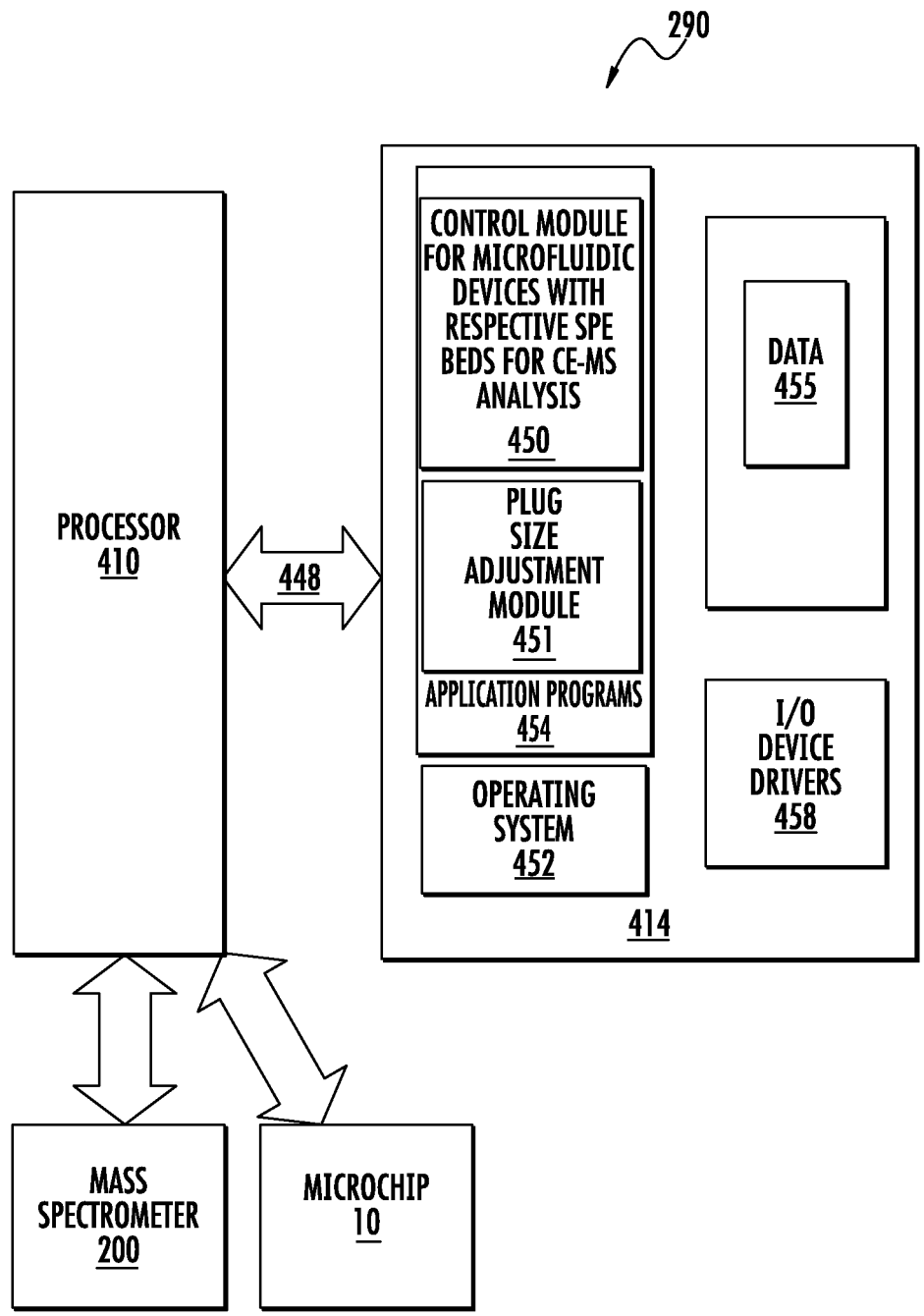
FIG. 11 is a block diagram of a data processing system according to embodiments of the present invention.

FIG. 11 is a schematic illustration of a circuit or data processing system 290. The system 290 can be used with microfluidic devices 10 and/or mass spectrometers 200. The circuits and/or data processing systems 290 may be incorporated in a digital signal processor in any suitable device or devices. As shown in FIG. 11, the processor 410 can communicate with a mass spectrometer 200 and/or microfluidic device 10 and with memory 414 via an address/data bus 448. The processor 410 can reside in a control circuit or controller that is separate from the spectrometer 200 or that is integrated wholly or partially therein. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 11 illustrates that the memory 414 may include several categories of software and data used in the data processing system: the operating system 452; the application programs 454; the input/output (I/O) device drivers 458; and data 455. The data 455 can include sample type, plug size adjustments for pressures, calibration data, time synchronization data (e.g., pressures/duration for loading/injection), and/or other detected or internal mass spectrometer data.

As will be appreciated by those of skill in the art, the operating systems 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000, WindowsXP or other Windows versions from Microsoft Corporation, Redmond, Wash., Unix or Linux or FreeBSD, Palm OS from Palm, Inc., Mac OS from Apple Computer, Lab- View, or proprietary operating systems. The I/O device drivers 458 typically include software routines accessed through the operating system 452 by the application programs 454 to communicate with devices such as I/O data port(s), data storage 455 and certain memory 414 components. The application programs 454 are illustrative of the programs that implement the various features of the data (image) processing system and can include at least one application, which supports operations according to embodiments of the present invention. Finally, the data 455 represents the static and dynamic data used by the application programs 454, the operating system 452, the I/O device drivers 458, and other software programs that may reside in the memory 414.

While the present invention is illustrated, for example, with reference to the Control Module for Microfluidic Devices with in-line SPE beds for CE-MS analysis of samples (typically with a Pressure Input Sequence) 450 and an optional Plug Size (pressure/duration) Adjustment Module 451 being application programs in FIG. 11, as will be appreciated by those of skill in the art, other configurations may also be utilized while still benefiting from the teachings of the present invention. The Module 451 can allow for a user to select a desired injection time (Pressure ON time, OFF time, pressure for a respective injection and/or clearing and the like, for each reservoir). The Modules 450 and/or 451 may also be incorporated into the operating system 452, the I/O device drivers 458 or other such logical division of the data processing system. Thus, the present invention should not be construed as limited to the configuration of FIG. 11, which is intended to encompass any configuration capable of carrying out the operations described herein. Further, Module 450 and/or 451 can communicate with or be incorporated totally or partially in other components, such as a mass spectrometer 200, power supply 95, an interface/gateway or a computer such as at a workstation that may be local or remote from the microfluidic device/spectrometer.

The I/O data port can be used to transfer information between the data processing system, the workstation, the spectrometer, the microfluidic device, the interface/gateway and another computer system or a network (e.g., the Internet) or to other devices or circuits controlled by the processor. These components may be conventional components such as those used in many conventional data processing systems, which may be configured in accordance with the present invention to operate as described herein.

The present invention is explained in greater detail in the following non-limiting Examples.

EXAMPLES

LC-MS grade acetonitrile, methanol, acetone, and formic acid (99.99%) were acquired from Fisher Chemical (Fairlawn, N.J.) as well as HPLC grade ammonium acetate and trifluoroacetic acid (TFA) (99.975%). Water was purified with a Nanopure Diamond water purifier (Barnstead International, Dubuque, Iowa). (3-Amino)di-isopropylethoxysilane (APDIPES) was acquired from Gelest (Morrisville, Pa.). Sodium phosphate dibasic, trichloro(1H,1H,2H,2H-perfluorooctyl)silane was acquired from Sigma-Aldrich (St. Louis, Mo.). N-hydroxylsuccinimide functionalized polyethylene glycol (NHS-PEG) reagent with 450 polymer units (MW=20 kDa) was purchased from Nanocs, Inc. (Boston, Mass.). Met-enkephalin, bradykinin, angiotensin II, thymopentin, and human glu-fibrionpeptide were purchased from American Peptide Company (Sunnyvale, Calif.). MassPREP Phosphorylase B and *E. coli* digest were procured from Waters Corporation (Milford, Mass.). A schematic for the SPE-CE-ESI microchip can be found in FIG. 1A. The microchip was fabricated out of 550 µm thick D263 glass using standard photolithography, wet chemical etching, and thermal bonding techniques. See, Mellors et al., *Anal Chem* 2008, 80, 6881-6887; and Mellors et al., *Anal Chem* 2010, 82, 967-973. All channels were 10 µm deep and 70 µm wide (full-width). The microchip was then coated with APDIPES and modified with an NHS-PEG reagent as described previously. See, e.g., Batz et al., *Anal Chem* 2014, 86, 3493-3500; and Redman et al., *Anal Chem* 2015, 87, 2264-2272. The contents of these documents are hereby incorporated by reference as if recited in full herein.

To perform integrated sample processing, SPE-CE-ESI microchips were packed with 5 µm diameter porous Oasis HLB particles provided by Waters Corporation (Milford, Mass.). The SPE bed was packed against a microfabricated weir by placing a slurry of 0.1 mg/mL Oasis HLB particles in acetone in reservoir 30 (FIG. 1A) and applying reduced pressure (optionally a vacuum) to reservoir 35 (FIG. 1A). The length of the packed bed was 600 µm long, while the channel depth and width were 10 µm and 70 µm, respectively. The volume of the packed bed was estimated to be 425 pL. The time required to pack the SPE bed on the microchip was 10 minutes.

To perform SPE-CE-ESI, the bed was first conditioned with low organic solvent. A 95:5 0.1% formic acid in water:methanol (v/v) solution was placed in reservoir 30 (FIG. 1A). Head pressure (+0.69 bar) from a tank of compressed nitrogen was applied to reservoir 30 while simultaneously applying a vacuum to reservoir 35 for 30 seconds. To load sample onto the SPE bed, the desired sample was placed in reservoir 30. Unless otherwise noted, the sample was dissolved in 2:98 methanol:0.5% TFA in water (v/v). The same pressure and vacuum were applied to the sample and waste reservoir, respectively, for 5 minutes. Finally, elution solvent replaced the sample in reservoir 2. For SPE-CE-ESI, the elution solvent was 80:20 acetonitrile: 2% formic acid in water (v/v).

For SPE-tITP-CE-ESI, the elution solvent was the same with the addition of 100 mM ammonium acetate. To perform an elution, the procedure was the same for both the SPE-CE-ESI and SPE-tITP-CE-ESI methods. First, +0.69 bar was applied to reservoir 30 for one second. Next, +0.69 bar was applied to both reservoirs 20 and 30 for four seconds. This resulted in the eluted analyte band entering the separation channel. Next, +0.69 bar was applied to reservoir one (20), which cleared the injection cross of excess sample prior to the application of voltage and creation of the injection plug. Finally, voltage was applied to reservoirs 20 (+22 kV) and 40 (+1.5 kV). The applied voltages resulted in a field strength of 760 V/cm. The application of the pressure and vacuum to the chip was controlled using a 3-way electronic valve (Clippard, Inc., Cincinnati, Ohio), which was operated by an SCB-68 breakout box connected to a PC via a PCI 6713 DAQ card (National Instruments, Austin, Tex.) and controlled by a Labview program. The BGE for all SPE-CE-ESI and SPE-tITP-CE-ESI separations was 50:50 acetonitrile:2% formic acid in water, pH 2.2.

Separation of a Four Peptide Mix

A four peptide mix (thymopentin, bradykinin, angiotensin II and met-enkephalin) was used to compare figures of merit for the three different methods investigated. A Waters Synapt G2 quadrupole time-of-flight (qTOF) mass spectrometer was used (Waters Corporation, Milford Mass.). The instrument was set to MS Sensitivity mode with a mass range of 300-600 m/z and a summed scan time of 0.09 seconds.

Electrokinetic and Hydrodynamic Injection Comparison

To compare differences in observed peak area between an electrokinetic gated injection and a hydrodynamic injection, microchip CE-ESI was used to separate a 5 µM four peptide mix (thymopentin, bradykinin, angiotensin II and met-enkephalin). A 23 cm CE-ESI microchip was utilized. The design is very similar to the microchip described in FIG. 1A, however, no weir was present in the channel 31 connected to reservoir 30, and no SPE bed was present. The depth and the width of the channels was the same as the SPE-CE-ESI microchip, as well as the surface coating. The BGE and MS settings were the same as those described earlier. For the electrokinetic injection, the applied voltages were 22, 22, 20, and 2 kV, respectively. The duration of the gated injection was 0.4 s. For the hydrodynamic injection, 0.165 bar of head pressure was applied to reservoirs 20 and 30 simultaneously for 3 seconds. This resulted in sample entering the separation channel. Next, 0.165 bar of pressure was applied to reservoir 20 for one second, which cleared the injection cross of excess sample creating the injection plug in the separation channel. Finally, applied voltages of 22 kV and 2 kV were applied to reservoirs 20 and 40, respectively. The analyte volumes for the injections were calculated by multiplying the volumetric flow rate (linear velocity x cross sectional area) and the injection time.

Sample Carry Over

Sample carry over was investigated for both the CE-ESI microchip and the SPE-CE-ESI microchip. For both techniques, a sample of the four peptide mix was separated at either 5 µM or 50 nM, respectively. Directly following the separation, the reservoir that contained the sample was rinsed by removing the sample and filling the reservoir with BGE. The solution was mixed by aspirating with a pipette. This process was repeated three times and then the reservoir was filled with a blank. For the CE-ESI microchip, the blank consisted of BGE. For the SPE-CE-ESI microchip, the blank consisted of 2% methanol, 0.5% trifluoracetic acid, and 97.5% water. For both techniques, the same sample loading and injection procedures that were used for the peptide mix was applied to the blank. The mass spectrometer settings were the same as those described for the separation of the 4-peptide mix.

Protein Digest Separations

A tryptic digest of Phosphorylase B was separated using both CE-ESI (5 µM) and SPE-tITP-CE-ESI (50 nM). Additionally, 0.5 mg/mL *E. coli* digest was analyzed using SPE-tITP-CE-ESI. A Waters Synapt G2 qTOF was used to perform $MS^E$. The term "$MS^E$" refers to a single analytical technique for Mass Spectrometers from Waters Corporation (Milford, Mass., USA) that can separate components of a complex sample and interrogate quantitative and qualitative information for review. See, White Paper, An Overview of the Principles of $MS^E$, the Engine that Drives MS Performance, Copyright 2011, Waters Corporation. To be clear, this White Paper and the noted analytical technique are provided by way of example only and the invention is not limited to this analysis protocol or this equipment. The instrument was set to MS/MS Sensitivity mode with a mass range of 50-1200 m/z and a summed scan time of 0.05 seconds. Human Glu-fibrinopeptide precursor was used as a lockmass compound, as described earlier.

Data Processing

To determine peak width and area, extracted ion electropherograms were exported into the program Igor Pro (Wavemetrics, Lake Oswego, Oreg.) and the analysis package "multi-peak fit 2" was used. To determine the peak capacity, base peak index (BPI) electropherograms were exported to the program PeakFinder (Pacific Northwest National Laboratory), which measured the separation window and median 4σ peak width.

The Phosphorylase B digest electropherograms were analyzed using the software Biopharmalynx (Waters Corporation) to determine the number of peptides observed. The method was based on a trypsin enzyme digest with up to two missed cleavages permitted. The MS and $MS^E$ mass tolerances were both set to 30.0 ppm. The MS ion intensity threshold was set to 25 counts, while the $MS^E$ ion intensity threshold was set to 10 counts. Only peptides with an intensity value greater than or equal to 1% of the most intense peptide were counted.

Results and Discussion

Separation and Pre-Concentration Performance

Figure 12A:
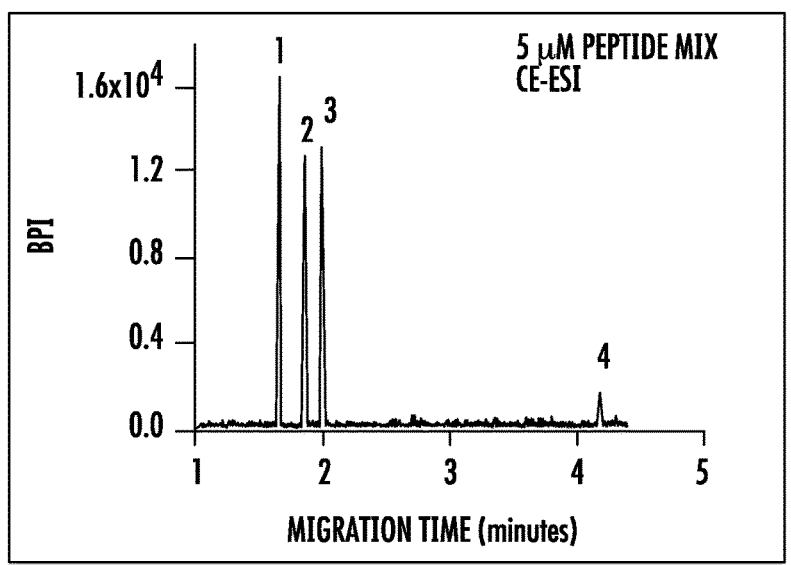
FIGS. 12A-12C are electropherograms (BPI versus migration time in minutes) of a 4-peptide mix.
Figure 12B:
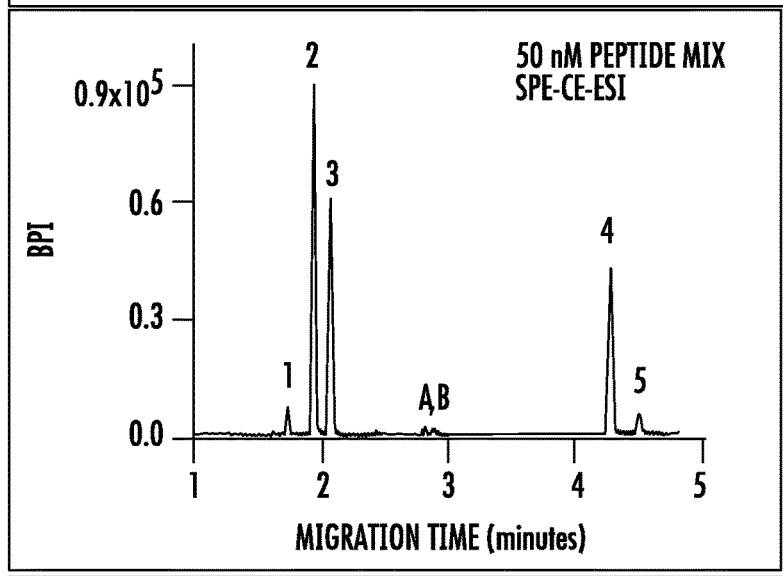
Figure 12C:
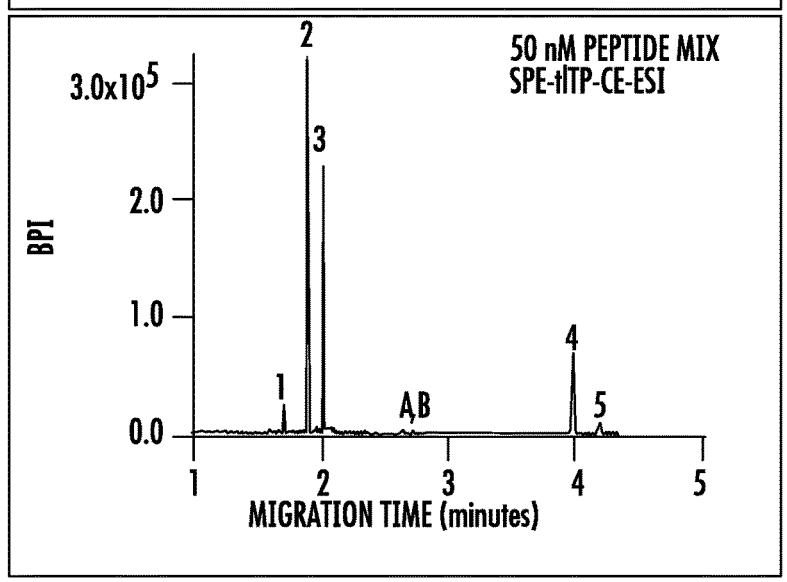
Figures 15A, 15B, 15C, 15D:
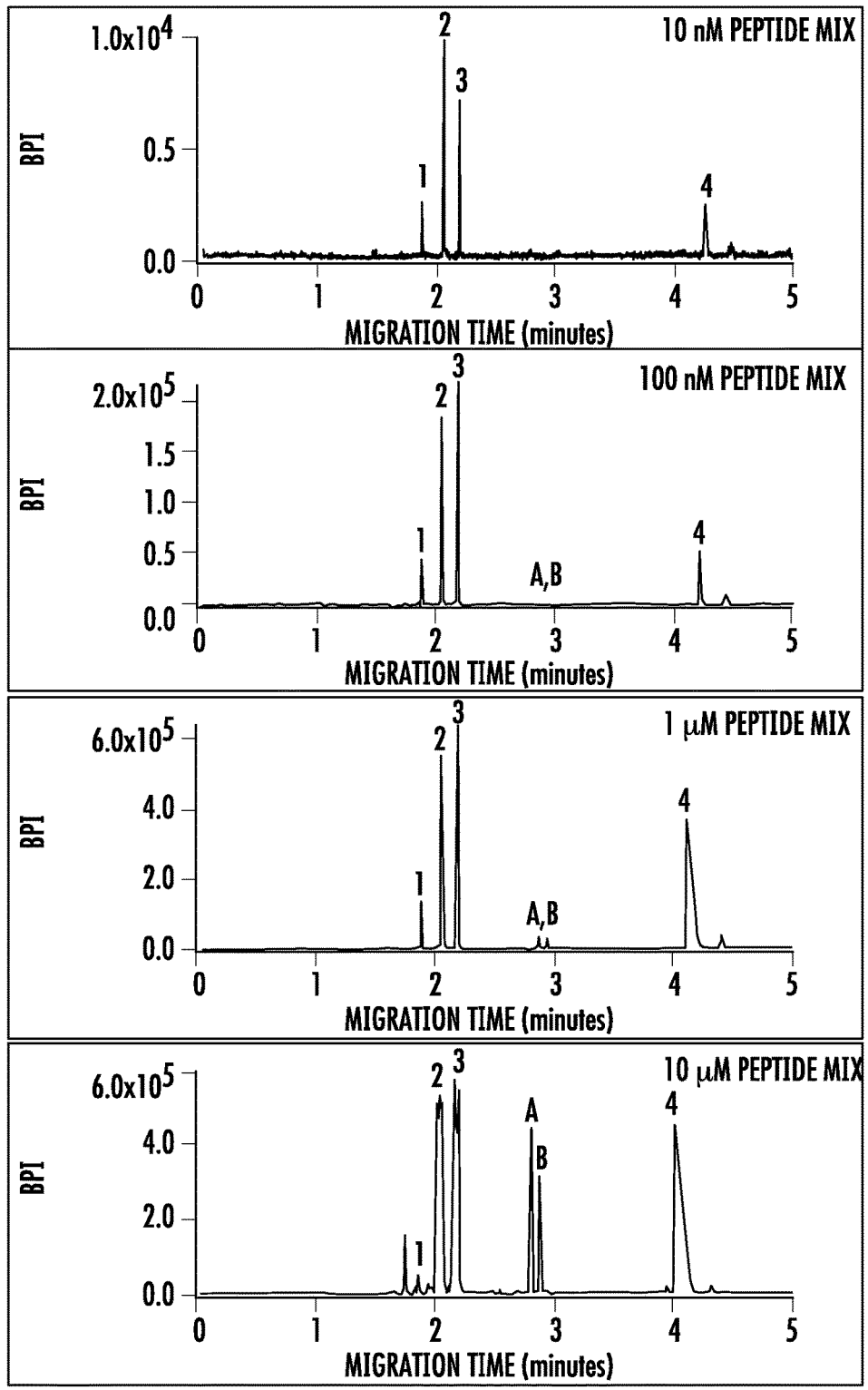
FIGS. 15A-15D are SPE-tITP-CE-ESI (for MS analysis) electropherograms of increasing concentrations of a four peptide mix according to embodiments of the present invention.

To investigate the concentration and separation performance of the integrated sample processing microchip three different approaches were compared; conventional CE-ESI, SPE-CE-ESI, and SPE-tITP-CE-ESI. All microchips were coupled directly with MS for detection. To ensure the separation conditions were identical for all methods, the CE separations were performed using the SPE-CE-ESI device without any stationary phase. Microchip CE-ESI separations were performed using a gated electrokinetic injection, while the SPE-CE-ESI and SPE-tITP-CE-ESI methods used a hydrodynamic injection. As long as the injection volume is sufficiently low to prevent injection broadening, the injection method will not have any influence on the separation performance. The affect of the injection method on the sensitivity of the methods is explored later. FIGS. 12A-12C compare the electropherograms for the three techniques while Table 1 compares the figures of merit. Theoretical plates are not an accurate measure of separation efficiency when tITP is coupled with CE, as the field strength is not linear across the channel for the duration of the separation. Since peak capacity does not require a linear electric field, it was therefore employed as a more accurate performance metric.

FIGS. 12A-12C show representative electropherograms from the three techniques. The peaks are labeled 1 through 4, and correspond to thymopentin, bradykinin, angiotensin II, and met-enkephalin, respectively. Peaks A (1087.5 Da) and B (1073.5 Da) correspond to unidentified trace peptides that were observed in the SPE-CE-ESI and SPE-tITP-CE-ESI electropherograms. The top electropherogram (FIG. 12A) corresponds to the CE-ESI analysis of a 5 µM peptide mix. The observed migration times for the four peptides were 1.64, 1.84, 1.98, and 4.19 min, respectively with a total separation time of just over four minutes long. The efficiency values for the CE-ESI approach were between 90,000 and 133,000 theoretical plates. The average peak capacity observed was 105.5, with a median 4σ peak width of 1.45 seconds and a separation window of 152.95 s (n=3). By using these figures of merit as a baseline, we can compare the separation performance of the SPE-CE-ESI and SPE-tITP-CE-ESI methods.

The middle electropherogram (FIG. 12B) corresponds to the SPE-CE-ESI analysis of 50 nM peptide mix, 100 times more dilute than the sample used for the CE-ESI separation. The migration time of the four peptides was 1.72, 1.92, 2.07 and 4.27 min respectively, very similar to the migration times for the CE-ESI electropherogram. Peak 5, at 4.50 min corresponds to oxidized met-enkephalin, which was not visible in the CE-ESI electropherogram, indicating the concentration enhancement of the SPE-CE-ESI approach. The theoretical plate counts of the four peptides using the SPE-CE-ESI method were between 39,000 and 92,000 theoretical plates and the observed peak capacity for the SPE-CE-ESI method was decreased to 66.5, with a median 4σ peak width of 2.30 s and a separation window of 152.95 s (n=3) (Table 1). These values did not take the oxidized met-enkephalin peak (peak 5) into account. FIG. 12C is a SPE-tITP-CE-ESI of a 50 nM sample.

TABLE 1

Calculated peak capacity and efficiency values for 4-peptide mix

| | Peak Capacity | Thymopentin | Bradykinin | Angiotensin II | Met-Enkephalin |
|---|---|---|---|---|---|
| CE-MS | 105.5 | 107,526 | 90,583 | 109,349 | 132,782 |
| SPE-CE-MS | 66.5 | 39,061 | 41,945 | 45,731 | 91,979 |
| SPE-tITP-CE-MS | 174.5 | 407,571* | 311,383* | 300,563* | 153,868* |

*Apparent efficiency values calculated based on peak width and migration time

To investigate the amount of pre-concentration observed, an enrichment factor was calculated for each of the four peptides. To characterize the effect of the different injection methods (hydrodynamic versus electrokinetic), microchip CE-ESI of the same four peptides was performed using both injection methods. The volume of analyte injected into the separation channel for an electrokinetic gated injection depends on the electrophoretic mobility of the analyte. For a hydrodynamic injection, the volume should be constant for all analytes. When comparing the pre-concentration performance of the SPE-CE-ESI and SPE-tITP-CE-ESI methods, it may be important to distinguish if any increase in observed sensitivity is due to pre-concentration of analyte on the bed or due to the removal of electrokinetic bias. FIGS. 13A and 13B illustrate the electropherograms for the electrokinetic (top, FIG. 13A) and hydrodynamic (bottom, FIG. 13B) injections for the four peptide mix. The peptides are labeled 1 through 4, corresponding to thymopentin, bradykinin, angiotensin II, and met-enkephalin. For the electrokinetic injection, the injection volumes of peaks 1 through 4 were calculated to be 585, 522, 482, and 215 pL, respectively. For the hydrodynamic injection separation, the injection volume was matched to the largest volume from the electrokinetic injection, and was calculated to be 600 pL. As illustrated by the figure as well as the injection volumes, the electrokinetic bias increases as the analyte migration time increases, corresponding to peptides with lower electrophoretic mobilities. The observed bias is especially prevalent for met-enkephalin (peak 4), while the average (n=3) peak heights for peaks 1 through 3 are within 20% of each other for each pair.

From the electropherograms in FIGS. 13A and 13B, the average (n=3 replicate injections) peak areas were calculated and compared between the two methods. FIG. 14 plots the calculated peak areas versus migration time for each of the four peptides. As illustrated by FIG. 14, no significant difference in peak area was observed for the first three peptides (peaks 1 through 3). However, a significant difference was observed for the met-enkephalin peak, the peptide with the lowest electrophoretic mobility, and therefore the highest electrokinetic bias. To account for this difference in sensitivity, a correction factor can be calculated by using a ratio of the electrokinetic injection peak area to the hydrodynamic injection. For met-enkephalin, this value was calculated to be 0.31, which is similar to the calculated difference in injection volume (215 v. 600 pL).

For the SPE-CE-ESI method, the enrichment values were 78, 712, 713, and 799 for peaks 1-4, respectively (FIG. 12C).

The enrichment factor was calculated by multiplying the difference in initial analyte concentration (100) by a ratio of the SPE-CE-ESI peak area compared to the CE-ESI peak area. For the met-enkephalin peak, the correction factor (0.31) was also used to account for the difference in peak area due to the differences in injection method.

The enrichment factor will vary due to differences in retention on the SPE bed as well. Thymopentin (Peak 1), a small (679.76 Da), hydrophilic peptide was not well retained on the hydrophobic stationary phase and thus had a much lower enrichment factor compared to the other peptides. Without the addition of TFA (0.5%) to the sample, thymopentin was not retained at all on the stationary phase (data not shown). Therefore, the lower observed enrichment factor of thymopentin compared to the other peptides was expected. TFA is an ion-pairing agent commonly used in chromatography, however, it is typically incompatible with ESI due to ion-suppression effects. The SPE-CE-ESI approach does not suffer this limitation, as TFA can be employed to retain the sample but can then be removed prior to elution. The ability to utilize TFA to improve retention of analytes on the SPE bed without compromising ESI performance represents a significant advantage of the SPE-CE-ESI microchip compared to LC-MS instruments where the TFA content is introduced directly into the mobile phase. The enrichment factors for bradykinin and angiotensin II were approximately 700, while the calculated value for met-enkephalin was 799. Overall, a significant amount of pre-concentration was observed using the SPE-CE method for the peptide mix. However, the resulting separation performance was reduced to roughly half that of the CE-ESI method, highlighting the challenge of coupling sample processing with CE-ESI while maintaining separation performance.

In order to regain the separation performance lost using the SPE-CE-ESI method while maintaining the observed pre-concentration, tITP was used prior to the CE-ESI separation. As tITP is a focusing technique, it produced a narrow injection band, eliminating any band broadening introduced by the transfer of the analyte band from the SPE bed to the CE channel. The electropherogram in FIG. 12C corresponds to the analysis of 50 nM peptide mix using the SPE-tITP-CE-ESI method. The procedure for this method is identical to the SPE-CE-ESI technique, except that 100 mM ammonium acetate was added to the elution solvent. The ammonium acts as the leading electrolyte and the formic acid in the BGE acts as the trailing electrolyte. Directly after the application of voltage to the microchip, the sample undergoes tITP focusing. Following the focusing step, the sample transitions to a CE separation. The migration times for the peptides are 1.68, 1.86, 1.98, and 3.98 min, respectively. Compared to both the CE-ESI and SPE-CE-ESI electropherograms, the separation window was compressed in the SPE-tITP-CE-ESI electropherogram due to the tITP focusing step. The average peak capacity observed was 174.5, with a median 4σ peak width of 0.81 s and a separation window of 141.33 s (n=3). This is nearly double compared to the CE-ESI separation, and nearly triple that for the SPE-CE-ESI method. The enrichment values for the four peptides were calculated to be 72, 614, 660, and 783, respectively. As evident by both the calculated peak capacity and enrichment values, the separation performance for the SPE-tITP-CE method is greatly improved compared to the CE and SPE-CE methods while providing a significant amount of sample pre-concentration.

Finally, to demonstrate the robustness of the developed methods the migration time reproducibility, peak area reproducibility, sample carryover, and limits of detection were investigated. For three replicate injections of the peptide mix, the average migration time RSD values were 0.23% for CE-ESI, 0.49% for SPE-CE-ESI, and 0.94% for SPE-tITP-CE-ESI. The average peak area RSD values were 7.08%, 5.26%, and 8.66%, respectively. These values indicate that both the SPE-CE-ESI and SPE-tITP-CE-ESI methods are reproducible, with migration time and peak area RSDs below 1 and 10%, respectively. To determine the limit of detection (LOD), the signal to noise (S/N) ratio of each peptide was calculated and then extrapolated to a S/N of 3. For the CE-MS method, the LOD of peaks 1 through 4 were calculated to be 800, 700, 400, and 700 nM, respectively. For the SPE-tITP-CE-MS method, the values were 3.0, 2.2, 2.6, and 1.7 nM, respectively, indicating more than two orders of magnitude lower LOD for the method with integrated sample processing. Sample carryover was compared for the SPE-CE and compared to the CE method. Following the separation of a four peptide mix (CE—5 μM, SPE-CE—50 nM), a blank was analyzed. Sample carryover was characterized by observing detection of any peptides in the blank electropherogram. For the CE electropherograms, no sample carryover was detected. For the SPE-CE electropherogram, carryover was only observed for bradykinin, the peptide with the most intense signal, yielding a peak area value of only 0.04% of the initial peak. This sample carryover is considered negligible and further optimization of wash steps between samples will likely eliminate it completely. The sample carryover performance of the SPE-CE-ESI method can be extrapolated to the SPE-tITP-CE-ESI method. The presence of salt in the elution solvent is the only difference between the two methods with all other steps identical, including the sample loading step and a wash step of the SPE bed following elution. Therefore, any residual material left on the SPE bed should be identical between the two methods. The high enrichment factors, low RSD values, low sample carryover and improvement in separation performance demonstrate the viability of this method for analyte pre-concentration for CE-ESI.

Dynamic Range and Overloading

When employing a stationary phase to pre-concentrate samples it can be important to ensure that the SPE bed does not become saturated in the desired concentration range. The integrated SPE-tITP-CE-MS method possesses three dimensions that are subject to sample overloading; the CE separation, the MS detector, and the adsorbent bed. As the sample can be continually loaded onto the adsorbent (SPE) bed, both volume and mass overloading must be considered. Volume overload occurs when a large volume (orders of magnitude larger than the volume of the stationary phase bed) of sample is injected onto the bed. Even under solvent conditions designed for sample adsorption (low organic), the large volume can cause weakly retained analytes to partition into the mobile phase and be eluted from the bed. Mass overload occurs when the amount of analyte injected exceeds the capacity of the stationary phase, saturating the bed with sample. It can be difficult to assign the effects of overloading to the saturation of the stationary phase alone and experiments must be carefully designed to ensure that it is characterized appropriately.

In order to determine the applicable dynamic range for the SPE-tITP-CE method the four peptide mix was investigated. The concentration range explored was 1, 10, 100, 1000 and 10000 nM. FIGS. 15A-15D illustrate BPI electropherograms for the peptide mix between 10 nM and 10 μM. The peptides were not visible in the BPI electropherogram of the 1 nM sample, but were observed in the extracted ion electropherogram. As demonstrated by FIGS. 15A-15D, the peak height and area for the four peptides increased as the concentration increased. The peak shape became distorted at high concentrations, and it appears that the detector becomes saturated. Furthermore, trace impurities were also present in the four peptide mix, and were observed at higher concentrations. Two of these impurities were labeled peptide A and B. The concentration of peptide A and B in the mixture were unknown, but it's estimated that they were at least an order of magnitude less concentrated than the four sample peptides.

FIGS. 16A-16C, 17A-17C and 18A-18C illustrate the peak area, width, and height of bradykinin, thymopentin, and peptide A, respectively, over the range of concentrations tested. These plots illustrate peak area, width, and height for SPE-tITP-CE-ESI analysis of bradykinin, thymopentin, and an unidentified trace component labeled peptide A. The concentration of the peptide mix loaded ranged from 1 nM to 10 μM. Sample concentration reflects the concentration of the 4 peptides in the mixture (thymopentin, bradykinin, angiotensin II, and met-enkephalin) and does not represent the concentration of the trace components A and B.

To determine overloading in the CE domain the peak width of bradykinin and peptide A were compared. The peak width of bradykinin remains unchanged from 1 nM to 100 nM. Above 100 nM, the peak width sharply increases. On the other hand, the peak width of the peptide A remains similar over the range of concentrations. This suggests that the CE separation has been saturated for the well-retained, highly abundant analyte. FIGS. 15A-15D visually support this conclusion. Monitoring the peak heights of the three peptides assesses the saturation of the MS detector. The peak height of bradykinin increased linearly ($R^2$=0.999) from 1 nM to 100 nM. However, at concentrations of 1 and 10 μM, the peak height deviated from the linear behavior and plateaued. The peak height of the weakly retained thymopentin increased linearly ($R^2$=0.999) between 1 nM and 100 nM. At 1 μM, the height began to deviate from linear and subsequently decreased. Comparatively, the peak height of the low abundant peptide A is linear ($R^2$=0.998) for all four concentrations of sample detected. This indicates that the MS detector had been saturated for the highly abundant species.

The values for peak area and height of the thymopentin suggest that volume overloading of the stationary phase is occurring. This is not surprising as the volume of sample is continually being introduced to the short bed (600 μm) for 5 minutes. In addition, the capacity of the bed for weakly retained analytes may decrease as the presence of other compounds with higher retention increases. Finally, to determine mass overload bradykinin and peptide A were compared. The peak area of bradykinin is linear through the first four orders of magnitude ($R^2$=0.998), while there is a deviation from linear behavior at 10 μM. The peak area of peptide A is linear ($R^2=0.999$) through the four concentrations that it was observed suggesting that the lower abundant analyte is still retained as the stationary phase has not yet been saturated. Based on these data, we conclude that the capacity of the 600 µm integrated SPE bed was sufficient to investigate samples that exist over a wide range of concentrations. The MS detector and the CE separation become saturated prior to saturation of the SPE bed. Even at a very large concentration of the four peptide mix, the peak height and area of the trace component A continued to increase linearly, indicating that the SPE bed still had capacity to hold more analyte. These conclusions are further supported by the behavior of angiotensin II and met-enkephalin, two additional abundant and well-retained peptides, as well as peptide B, an additional trace component in the four peptide mixture (FIGS. 19A-19C, 20A-20C, 21A-21C).

FIGS. 19A-19C, 20A-20C, 21A-21C show peak area, peak width, and peak height for angiotensin II, met-enkephalin, and unidentified peptide B, respectively. The concentration of the sample loaded ranged from 1 nM to 10 µM.

Complex Mixture Separations

Figure 22:
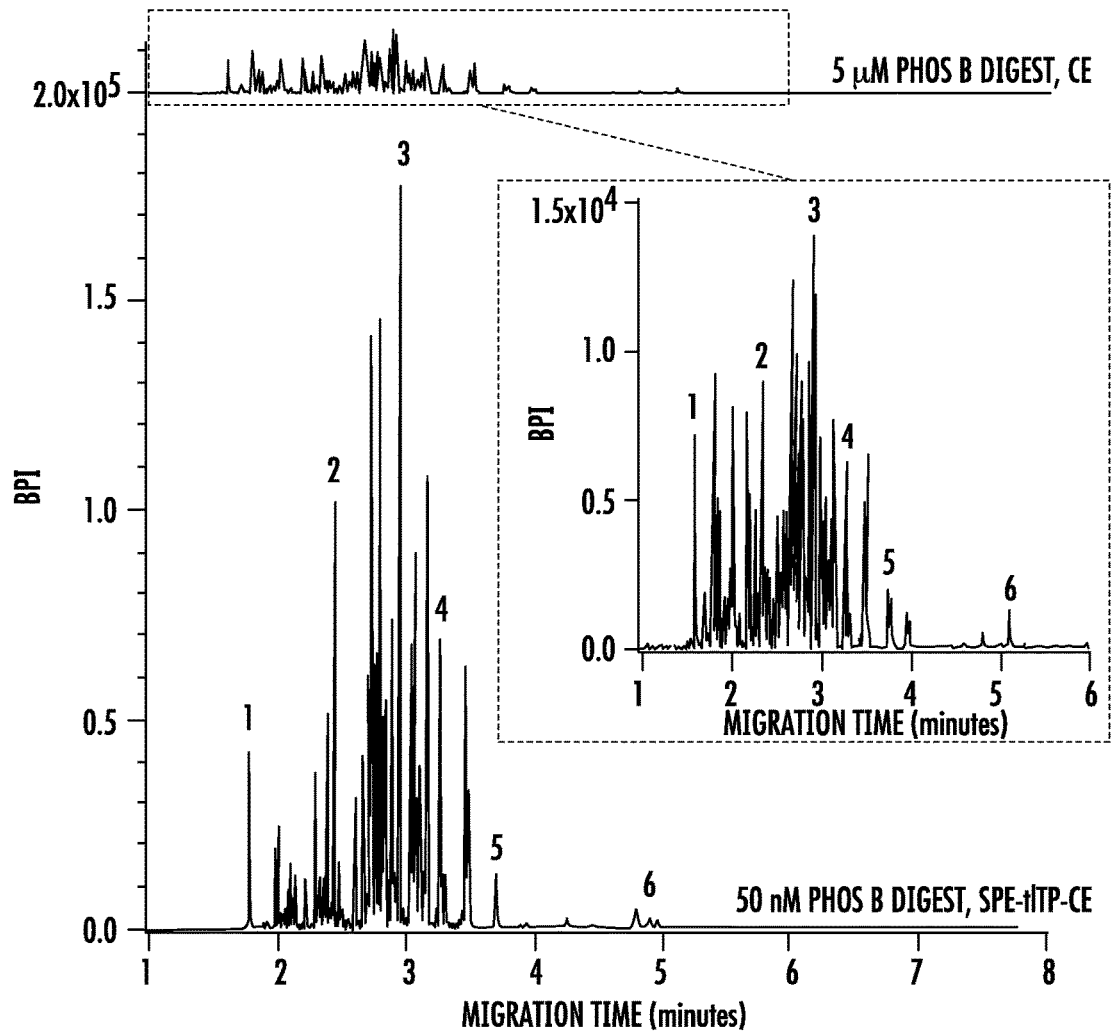
FIG. 22 are electropherograms (BPI versus migration time (minutes)) of phosphorylase B tryptic digests separated using CE-ESI (top and enlarged inset) and SPE-tITP-CE-ESI (bottom).

In order to investigate the performance of the microchip with integrated sample processing for complex mixtures, a Phosphorylase B (Phos B) tryptic digest was analyzed using both CE-ESI-MS/MS and SPE-tITP-CE-ESI-MS/MS. Peptide identification via tandem MS is typically employed in many applications, such as protein mapping, proteomics, or hydrogen/deuterium exchange mass spectrometry. Therefore, tandem MS was used to demonstrate the compatibility of the SPE-tITP-CE-ESI method with MS/MS. The concentration of the sample for CE was 5 µM, while the concentration of the sample for SPE-tITP-CE was 50 nM. FIG. 22 illustrates a comparison of the electropherograms for each separation. Both methods are contained on the same plot, with the CE electropherogram offset for visualization. The inset shows an expanded view of the CE electropherogram. Six peptides were selected and are labeled in each of the electropherograms for comparison. As illustrated by the figure, the BPI signal intensity for the SPE-tITP-CE electropherogram is more than an order of magnitude greater than the CE electropherogram, despite having a 100-fold lower sample concentration. By comparing the average peak area of the six labeled peptides, enrichment factors of 270, 550, 541, 712, 426, and 418 were calculated (ignoring any electrokinetic bias) for peaks 1 through 6, respectively. Furthermore, the appearance of each electropherogram was very similar. For the CE separation, the average (n=3) peak capacity was 128, with a median 4σ peak width of 1.68 seconds and a separation window of 214.8 seconds. For the SPE-tITP-CE separation, the average (n=3) peak capacity was 147, with a median 4σ peak width of 1.267 seconds, a separation window of 186.4 seconds.

It is well known that SPE is biased towards analytes that are retained well on the chromatographic material, and that the method is less effective at analyzing species that are poorly retained. For reversed-phase SPE, analytes that are very polar are typically not retained, resulting in a loss of these analytes. In order to determine if a similar number of peptides were observed between the CE-MS and SPE-tITP-CE-MS Phos B samples, the electropherograms were analyzed using the software Biopharmalynx. For the CE-MS analysis, the average (n=3) number of peptides observed in the Phos B digest was 151. Comparatively, the average (n=3) number of peptides observed for the SPE-tITP-CE-MS method was 97, which corresponds to a 35% decrease. While completely eliminating the bias of SPE towards well retained analytes is challenging, reducing the number of peptides lost could be accomplished by further optimizing the stationary phase, such as selecting a more retentive reversed-phase material or selecting a mixed mode stationary phase, such as combining reversed-phase retention with ion exchange retention.

FIG. 22 are electropherograms of Phosphorylase B tryptic digests separated using CE-ESI (5 µM) (top and top inset) and SPE-tITP-CE-ESI (50 nM) (bottom). The inset shows an expanded view of the CE-ESI electropherogram.

Figure 23:
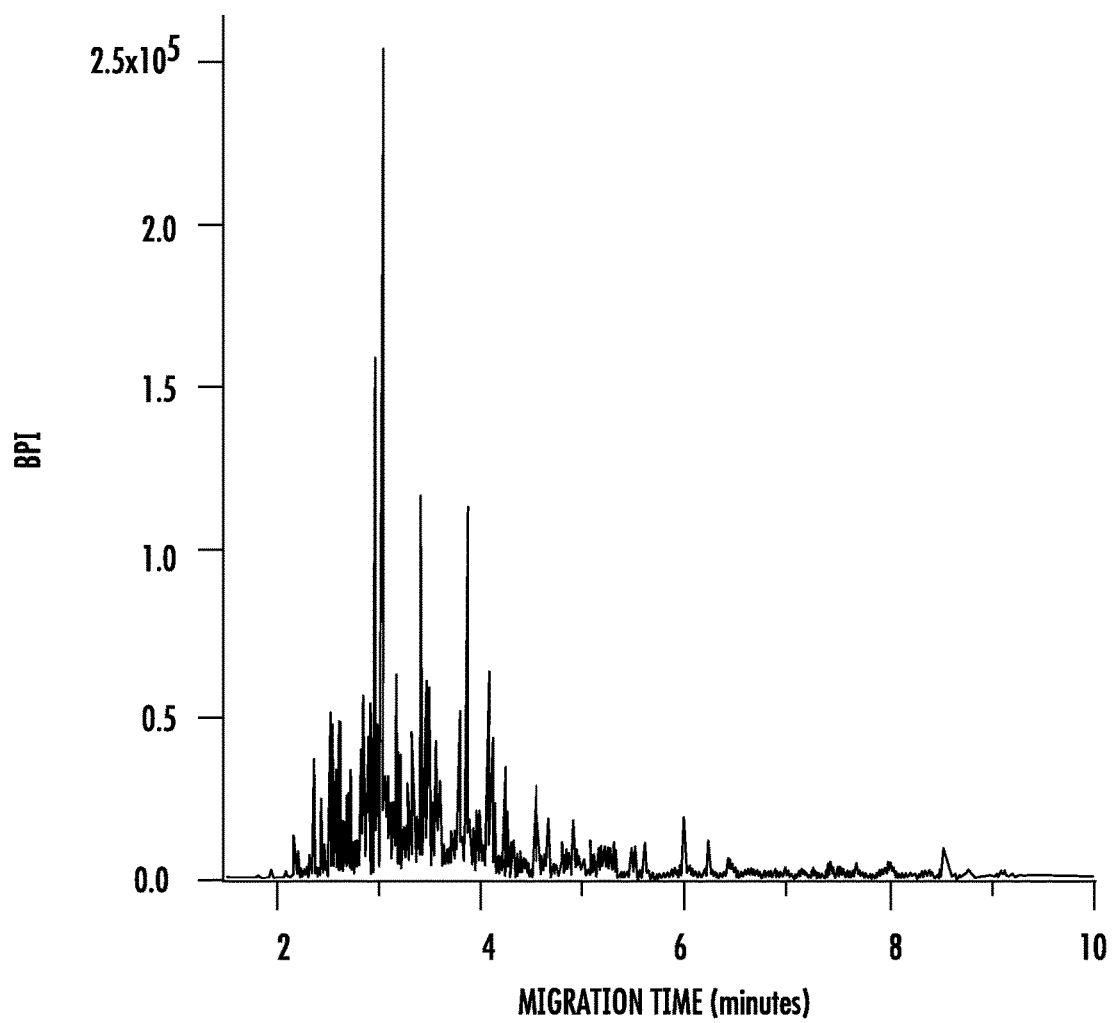
FIG. 23 is an electropherogram of SPE-tITP-CE-ESI separation of 0.5 mg/mL *E. coli* digest (BPI versus migration time, minutes) according to embodiments of the present invention.

FIG. 23 illustrates the separation of 0.5 mg/mL E. coli tryptic digest using the integrated microchip. The separation run time is just under 10 minutes long. The calculated peak capacity for the separation was 241.5, with a median 4σ peak width of 1.85 s, a separation window of 447.6 s, and 155 peaks counted. Busnel et al. coupled tITP-CE with a porous tip emitter to perform a similar separation of 0.5 mg/mL E. coli tryptic digest. See, e.g., Busnel, et al., Anal Chem 2010, 82, 9476-9483, the contents of which are hereby incorporated by reference as if recited in full herein.

The authors reported an observed peak capacity (4σ peak width) of 192 in 80 min. The metric of peak capacity/min can be used to compare the rate at which different separations techniques can generate resolving power. The separation described in the Busnel manuscript has a peak capacity/min of 2.4 based on the reported peak capacity and a separation run time of 80 min. The calculated value for the electropherogram in FIG. 23 corresponds to a peak capacity/min of 24.1, based on a peak capacity of 241.5 and a run time of 10 min. If one includes the 5 minutes of loading prior to the separation, the value of peak capacity/minute drops to 16.1, which is still over 6 times faster than the work reported by Busnel et al. Further optimization of the loading step prior to the separation will likely reduce the total analysis time of an individual sample. FIG. 23 is an electropherogram of SPE-tITP-CE-ESI separation of 0.5 mg/mL E. coli digest.

Figure 24A:
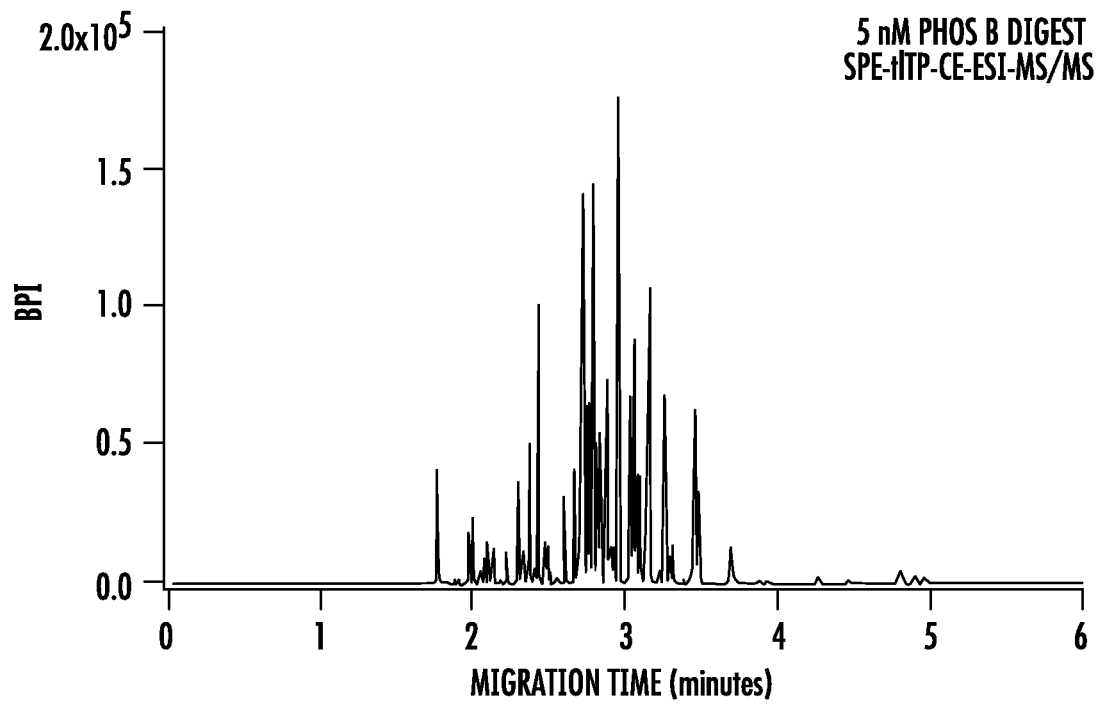
FIGS. 24A and 24B are electropherograms of SPE-tITP-CE-ESI MS illustrating desalting capability of the integrated SPE-tITP-CE-ESI microfluidic devices contemplated by embodiments of the present invention.
Figure 24B:
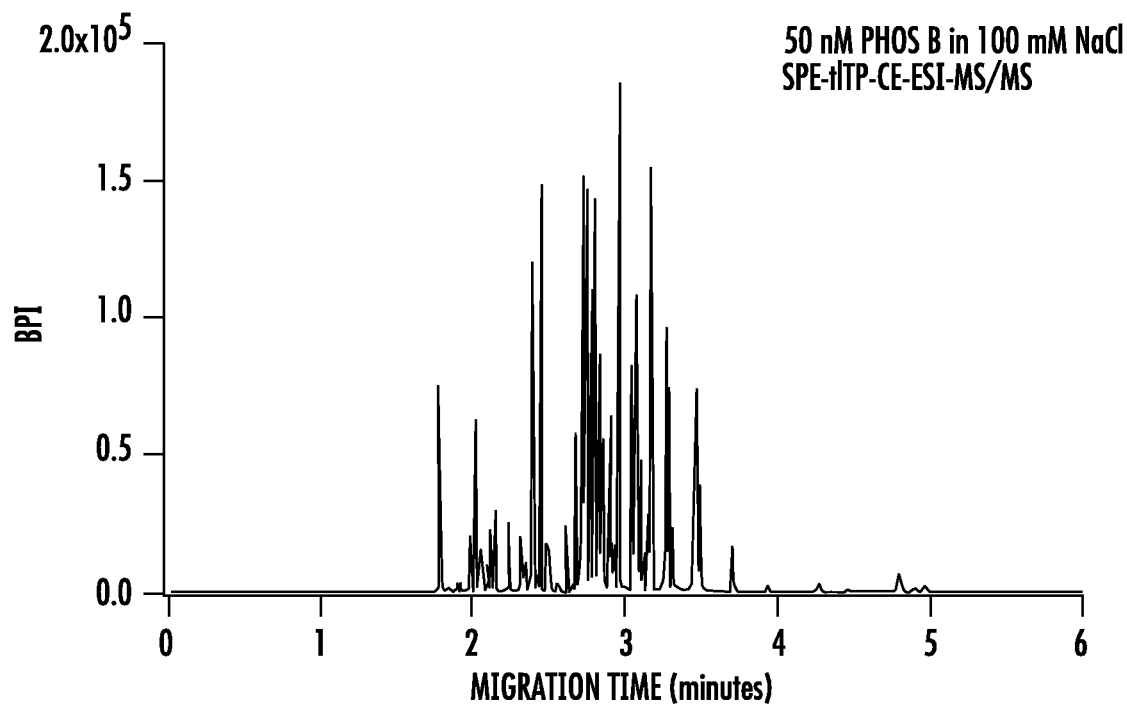

FIGS. 24A and 24B illustrate results of a preliminary experiment carried out to assess desalting capabilities of an integrated SPE-tITP-CE-ESI microfluidic device. The electropherograms correspond to the same sample dissolved in two different formulations prior to analysis by SPE-tITP-CE-ESI-MS/MS. Both are 50 nM Phosphorylase B digest, with the top electropherogram (FIG. 24A) corresponding to the sample dissolved in loading buffer (2% methanol, 0.5% TFA, remainder water). The bottom electropherogram (FIG. 24B) is the same sample, except dissolved in (2% methanol, 0.5% TFA, remainder water+100 mM NaCl). This simulates the ability of the SPE-tITP-CE-ESI device to desalt or clean up a sample prior to separation and mass spectrometer detection. A short wash step was used in between sample loading and sample elution (see, e.g., FIGS. 2E, 3C discussed above). The wash step was 10 seconds long and the sample was washed with 5% methanol, 0.1% formic acid, remainder water. As illustrated, the signal intensity of each electropherogram was very similar, indicating that the amount of pre-concentration was not affected by the presence of salt in the sample. For three replicate injections, the average peak capacity of the top electropherogram was 150, while the average peak capacity of the bottom electropherogram was 157. Therefore, the separation performance was also not affected by the presence of salt in the sample. This preliminary experiment indicates that in addition to pre-concentration, the SPE-tITP-CE-ESI device can desalt and clean up samples prior to analysis.

The foregoing is illustrative of the present invention and is not to be construed as limiting thereof. Although a few exemplary embodiments of this invention have been That which is claimed:

1. A mass spectrometry system, comprising:
a mass spectrometer;
a microfluidic device onboard or in communication with the mass spectrometer, the microfluidic device comprising at least one separation channel in fluid communication with a background electrolyte (BGE) reservoir, a sample channel in fluid communication with the separation channel, a sample reservoir in fluid communication with the sample channel, a waste channel in fluid communication with the separation channel, a waste reservoir in fluid communication with the waste channel, and at least one electrospray ionization (ESI) emitter in fluid communication with the separation channel, wherein the sample channel comprises at least one solid phase extraction (SPE) bed;
a first conduit in communication with a first valve coupled to the BGE reservoir;
an electrode extending into the BGE reservoir so that when fluid is present in the BGE reservoir, the electrode is in electrical communication with the fluid;
a second conduit in communication with a second valve coupled to the sample reservoir;
a third conduit in communication with a third valve coupled to the waste reservoir;
at least one voltage source electrically connected to the electrode;
a first gas source in fluid communication with the first and second conduits;
a second gas source or a pressure-reducing device in fluid communication with the third conduit; and
a controller in electrical communication with the first gas source, the second gas source or pressure-reducing device, and the at least one voltage source, and configured so that during operation of the system, the controller:
(i) applies a pressure to a headspace of the waste reservoir through the third conduit and concurrently applies a pressure to a headspace of the sample reservoir through the second conduit such that the pressure applied to the headspace of the waste reservoir is less than the pressure applied to the headspace of the sample reservoir;
(ii) concurrently applies pressures to the headspaces of the sample reservoir and the BGE reservoir without applying a voltage to fluid in the sample reservoir or to fluid in the BGE reservoir; then
(iii) reduces the pressure applied to the headspace of the sample reservoir so that the pressure then applied to the BGE reservoir is greater than the pressure applied to the sample reservoir to transport a sample and fluid from the BGE reservoir into the at least one separation channel; then
(iv) applies an electric field along the separation channel using the at least one voltage source to electrophoretically separate an analyte component from the sample; and then
(v) performs electrospray ionization of the analyte component using the at least one ESI emitter to direct ions of the analyte component toward a collection device or an inlet of the mass spectrometer.

2. The system of claim 1, wherein the sample channel comprises at least one blocking member positioned adjacent to an end portion of the at least one SPE bed that is closest to the separation channel.

3. The system of claim 1, wherein the SPE bed comprises a length, measured along a flow direction of the sample channel toward the separation channel, of between 100 μm and 1000 μm, and a volume of between about 50 pL and about 10 n.

4. The system of claim 1, wherein the SPE bed has a leading end positioned a distance of between 10 μm and 5 cm upstream from the separation channel.

5. The system of claim 1, wherein the sample channel is valveless so that the SPE bed is in uninterrupted fluid communication with the separation channel.

6. The system of claim 1, wherein a leading end of the at least one SPE bed is positioned at a distance of between 50 μm and 500 μm from the separation channel.

7. The system of claim 1, wherein the sample channel has a branched segment of first and second branches that merge into a single channel segment that holds the SPE bed.

8. The system of claim 7, wherein the first branch is in fluid communication with a first reservoir and the second branch is in fluid communication with the sample reservoir.

9. The system of claim 1, further comprising a detector in communication with the ESI emitter that detects a signal corresponding to the analyte component.

10. The system of claim 1, wherein the electric field is applied to the microfluidic device so that at least a component of the electric field is parallel to an axial direction of at least a portion of the separation channel.

11. The system of claim 1, wherein the applied electric field applies an electrical potential difference between a first position in the BGE reservoir and a second position downstream from the first position, wherein the second position is located in the separation channel or in a pump channel or in a reservoir in fluid communication with one or both of the separation or the pump channel of the microfluidic device.

12. The system of claim 1, wherein, in operation, the sample is flowed through the sample channel without applying a voltage to the sample reservoir, to the BGE reservoir, or to the waste reservoir and/or with no electric potential gradient in any of the sample channel, the BGE channel and the waste channel.

13. The system of claim 1, wherein the pressure applied concurrently to the headspace of the waste reservoir and the headspace of the sample reservoir is in a range of 0.1 pounds per square inch (psi) and 30 psi.

14. The system of claim 1, wherein at (iii) the reduced pressure applied to the headspace of the sample reservoir is in a range of 0.1 psi and 30 psi with the pressure then applied to the BGE reservoir being greater than the pressure applied to the sample reservoir to transport the sample from the BGE reservoir into the separation channel.

15. The system of claim 14, wherein in (i) the concurrent pressures applied to the sealed headspaces of the BGE reservoir and the sample reservoir are each between 0.5 psi and 50 psi, and wherein in (iii) no pressure is applied to the sealed headspace of the sample reservoir and the pressure applied to the sealed headspace of the BGE reservoir to transport the sample is between 0.1 psi and 10 psi.

16. The system of claim 1, wherein one or more of the at least one separation channel, the sample channel, or the waste channel is a nanofluidic channel.

17. The system of claim 1, wherein the sample channel is configured as a plurality of separate sample channels that merge into one of the at least one separation channel.

18. The system of claim 17, wherein each of the plurality of separate sample channels comprises a respective SPE bed.

19. The system of claim 17, wherein the sample channel has a plurality of branches upstream of the SPE bed that merge into a portion of the sample channel that holds the SPE bed.

20. The system of claim 1, wherein the at least one SPE bed of the sample channel is a plurality of spaced apart SPE beds.

* * * * *